United States Patent [19]

Jonczyk et al.

[11] Patent Number: 5,747,457
[45] Date of Patent: May 5, 1998

[54] LINEAR ADHESION INHIBITORS

[75] Inventors: Alfred Jonczyk, Darmstadt, Germany; Brunhilde Felding-Habermann, La Jolla, Calif.; Beate Diefenbach, Darmstadt; Friedrich Rippmann, Heidelberg, both of Germany

[73] Assignee: Merck Patent Gesellschaft Mit Beschrankter Haftung, Darmstadt, Germany

[21] Appl. No.: 329,820

[22] Filed: Oct. 27, 1994

[30] Foreign Application Priority Data

Oct. 28, 1993 [DE] Germany ............ 43 36 758.5

[51] Int. Cl.⁶ .................. A61K 38/00; A61K 38/04; C07K 5/00; C07K 16/00
[52] U.S. Cl. .................. 514/13; 530/326; 530/327; 530/328; 530/329; 530/330; 514/13; 514/14; 514/15; 514/16; 17/18
[58] Field of Search .................. 530/326–300; 514/13–18

[56] References Cited

U.S. PATENT DOCUMENTS 2,799,670  7/1957  Laufer et al. .................. 260/112
4,177,277  12/1979  Ondetti et al. .................. 424/263

FOREIGN PATENT DOCUMENTS 0 382 538  8/1990  European Pat. Off.
0406428    1/1991  European Pat. Off.
WO 90/15072  12/1990  WIPO

OTHER PUBLICATIONS

Edington, Biotechnology, vol. 10, pp. 383–386, 388–389, 1992.

Paulson, Adhesion. Selectin/Carbohydrate—Mediated Adhesion of Leukocytes, pp. 19–41, 1990.

"Echistatin", Zhong-Ru Ghan et al., Journal of Biological Chemistry, vol. 263 (36), Dec. 25, 1988, pp. 19827–19832.

*Primary Examiner*—Cecilia J. Tsang
*Assistant Examiner*—Sandia Marshall
*Attorney, Agent, or Firm*—Millen, White, Zelano, & Branigan, P.C.

[57] ABSTRACT

Linear peptides of the formula I $$X\text{-}A\text{-}Cys(R^1)\text{-}B\text{-}Z \qquad \qquad I$$

in which

A, B, $R^1$, X and Z are as defined, are highly active inhibitors of the binding of the blood platelet integrin GP IIbIIIa ($a_{IIb}\beta_3$) to natural ligands and are suitable, inter alia, for the prophylaxis and for the treatment of circulatory disorders, thrombosis, myocardial infarction, coronary heart disease, arteriosclerosis, atherosclerosis, tumors and osteolytic diseases, and have a supporting effect in wound healing processes.

22 Claims, No Drawings

LINEAR ADHESION INHIBITORS

SUMMARY OF THE INVENTION

The invention relates to novel linear peptides of the formula I

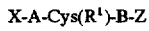

X-A-Cys($R^1$)-B-Z      I, which have been derived from the C-terminal sequence of echistatin and in which x is H or Ac, A is absent or is Asp or a peptide fragment selected from a group consisting of Ala-Asp, Thr-Ala-Asp, Lys-Thr-Ala-Asp (SEQ ID NO:1), Lys-Thr-Ala-Asn (SEQ ID NO:2), Lys-Thr-Gly-Asp (SEQ ID NO:3), Lys-Ala-Ala-Asp (SEQ ID NO:4), Arg-Thr-Ala-Asp (SEQ ID NO:5), Ser-Ala-Asp, Gln-Ser-Ala-Asp (SEQ ID NO:6), Gly-Lys-Thr-Ala-Asp (SEQ ID NO:7), Asn-Gly-Lys-Thr-Ala-Asp (SEQ ID NO:8), Ile-Ser-Ala-Gly (SEQ ID NO:9), Arg-Ser-Ala-Gly (SEQ ID NO:10), Cys-Asn-Gly-Lys-Thr-Ala-Asp (SEQ ID NO:11), Tyr-Cys-Asn-Gly-Lys-Thr-Ala-Asp (SEQ ID NO:12), Asp-Tyr-Cys-Asn-Gly-Lys-Thr-Ala-Asp (SEQ ID NO:13), Gly-Lys-Thr-Cys-Asp (SEQ ID NO:14), Asp-Asp-Tyr-Cys-Asn-Gly-Lys-Thr-Ala-Asp (SEQ ID NO:15), Gly-Lys-Thr-Cys(Trt)-Asp (SEQ ID NO:16), Met-Asp-Asp-Tyr-Cys-Asn-Gly-Lys-Thr-Ala-Asp (SEQ ID NO:17) and Asp-Met-Asp-Asp-Tyr-Cys-Asn-Gly-Lys-Thr-Ala-Asp (SEQ ID NO:18);

B is absent or is Ala, Arg, Asn, Asp, Cys, Gln, Glu, Gly, His, Ile, Leu, Lys, Met, Orn, Phe, 4-Hal-Phe, Pro, Ser, Thr, Trp, Tyr or Val or is an N-methylated derivative of the amino acid residues mentioned, or is a peptide fragment selected from the group consisting of Pro-Arg, Pro-Arg-Asn, Pro-Arg-Asn-Pro (SEQ ID NO:19), Pro-Arg-Asn-Pro-His (SEQ ID NO:20), Pro-Arg-Asn-Pro-His-Lys (SEQ ID NO:21), Pro-Arg-Asn-Pro-His-Lys-Gly (SEQ ID NO:22), Pro-Arg-Asn-Pro-His-Lys-Gly-Pro (SEQ ID NO:23), Pro-Arg-Asn-Pro-His-Lys-Gly-Pro-Ala (SEQ ID NO:24), and Pro-Arg-Asn-Pro-His-Lys-Gly-Pro-Ala-Thr (SEQ ID NO:25), in which only one of the residues A or B can be absent;

Z is OH, $OR^2$, $NH_2$, $NHR^2$ or $N(R^2)_2$;

$R^1$ is H, $R^2$, Trt, Dpm or Bzl;

$R^2$ is alkyl of 1–6 carbon atoms;

Hal is F, Cl, Br or I; and

Ac is alkanoyl of 1–10 carbon atoms, aralkanoyl of 8–10 carbon atoms or aroyl of 7–11 carbon atoms, and to their physiologically acceptable salts.

It is preferred that the peptides contain 4–17 amino acids.

Similar compounds are known from, for example, European Patent Application EP 0 406 428.

An object of the invention was to provide new compounds having valuable properties, especially those which can be used for the preparation of medicaments.

Upon further study of the specification and appended claims, further objects and advantages of this invention will become apparent to those skilled in the art.

It has been found that the compounds of the formula I and their salts possess highly valuable properties. They act in particular as integrin inhibitors, in which context they particularly inhibit the interactions of $\beta_3$-integrin receptors with ligands, in particular by inhibiting the binding of blood platelet integrin GP IIbIIIa ($a_{IIb}\beta_3$) to natural ligands. This action can be demonstrated by, for example, the method described by J.W. Smith et al. in J. Biol. Chem., 265:12267–12271 (1990). In addition to this, there are anti-inflammatory effects. This action can also be demonstrated using methods known from the literature.

It is known that compounds which inhibit or block the $\beta_3$-integrin receptor ligand interactions, such as the binding of fibrinogen to $\beta_3$-integrin receptors (adhesion receptor antagonist or ARA), can be used as therapeutic agents. Furthermore, such compounds also inhibit cell adhesion in the case of the formation of osteoclasts.

The compounds can be employed as active substances of medicaments in human and veterinary medicine, especially for the prophylaxis and for the treatment of circulatory disorders, thrombosis, myocardial infarction, coronary heart disease, arteriosclerosis, atherosclerosis, inflammation, apoplexy, angina-pectoris, tumors (e.g., melanoma, sarcoma and epithelioma), osteolytic diseases, especially osteoporosis, angiogenesis and restenosis after angioplasty. In addition, they may have a supportive action in wound healing processes.

There is evidence that tumor cells spreading from a solid tumor into the vasculature are carried by microthrombi and thus are protected from being detected by cells of the immune system. The second step of attachment to the vessel wall seems to be facilitated by microthrombi as well. Since the formation of thrombi is mediated by fibrinogen binding to the fibrinogen receptor (glycoprotein IIb/IIIa) on activated platelets, fibrinogen-binding inhibitors are expected to be effective as antimetastatics.

Also, since fibrinogen-binding inhibitors are ligands with fibrinogen receptor on platelets, they can be used as diagnostic tools for detection and localization of thrombi in the vascular in vivo. Thus, for example, in accordance with known procedures, the fibrinogen-binding inhibitors can be labeled with a signal generating or detectable moiety whereby, once the labeled fibrinogen-binding inhibitor is bound to a fibrinogen receptor on platelets, it is possible to detect and locate thrombi.

Fibrinogen-binding inhibitors are also very effective as research tools for studying the metabolism of platelets in the different activation states or intracellular signalling mechanisms of the fibrinogen receptor. For example, as described above, fibrinogen-binding inhibitor can be labeled with a signal generating or detectable moiety. The fibrinogen-binding inhibitor-signal generating/detectable moiety conjugate can then be employed in vitro as a research tool. By binding the conjugate to fibrinogen receptors, it is possible to monitor and study the metabolism of platelets, as well as the activation states and signalling mechanisms of the fibrinogen receptors.

The compounds are also suitable as antimicrobial agents which avoid or prevent infections as caused, for example, by bacteria, fungi or yeasts. The substances are useful as accompanying antimicrobial agents in cases where operations are effected in order to insert non-corporal materials, for example, such as biomaterials, implants, catheters or heart-pacemakers. They act as antiseptics. Antimicrobial activity of the compounds can be demonstrated by the procedure described by P. Valentin-Weigund et al., Infection and Immunity, pp.2851–2855 (1988).

The abbreviations of amino acid residues given above and below denote the residues of the following amino acids:

| | |
|---|---|
| Ala | alanine |
| Arg | arginine |
| Asn | asparagine |

| Asp | aspartic acid |
| --- | --- |
| Cys | cysteine |
| Gln | glutamine |
| Glp | pyroglutamine |
| Glu | glutaminic acid |
| Gly | glycine |
| His | histidine |
| Ile | isoleucine |
| Leu | leucine |
| Lys | lysine |
| Met | methionine |
| Orn | ornithine |
| Phe | phenylalanine |
| Pro | proline |
| Ser | serine |
| Thr | threonine |
| Trp | tryptophan |
| Tyr | tyrosine |
| Val | valine. |

Furthermore, the abbreviations used below have the following definitions:

| BOC | tert-butoxycarbonyl |
| --- | --- |
| Bzl | benzyl |
| CBZ | benzyloxycarbonyl |
| DCCI | dicyclohexylcarbodiimide |
| Dpm | diphenylmethyl |
| DMF | dimethylformamide |
| EDCI | N-ethyl-N'-(3-dimethylaminopropyl)carbodiimide hydrochloride |
| Et | ethyl |
| Et$_2$O | diethyl ether |
| Fmoc | 9-fluorenylmethoxycarbonyl |
| HOBt | 1-hydroxybenzotriazole |
| Me | methyl |
| MBHA | 4-methyl-benzhydrylamine |
| Mtr | 4-methoxy-2,3,6-trimethylphenyl-sulfonyl |
| OBut | tert-butyl ester |
| OMe | methyl ester |
| OEt | ethyl ester |
| POA | phenoxyacetyl |
| TFA | trifluoroacetic acid |
| Trt | trityl (triphenylmethyl). |

Where the above-mentioned amino acids have a chiral center and may occur in two or more enantiomeric forms, then above and below, for example as a component of the compounds of the formula I, all of these forms and their mixtures too (e.g., the DL forms) are included, the three-letter code being the respective L form if the stereochemistry is not indicated.

The invention relates furthermore to a process for the preparation of a compound of the formula I according to claim 1 or one of its salts, characterized in that it is liberated from one of its functional derivatives by treatment with a solvolyzing or hydrogenolyzing agent or in that a peptide of formula II

X-M-OH            II, in which

M is an amino acid residue or peptide radical selected from a group consisting of A, A-Cys(R$^1$), Ala, Thr, Thr-Ala, Lys, Lys-Thr, Lys-Thr-Ala, Lys-Thr-Ala-Gly (SEQ ID NO:26), Gly, Gly-Lys, Gly-Lys-Thr, Gly-Lys-Thr-Ala (SEQ ID NO:27), Gly-Lys-Thr-Cys(R$^1$) (SEQ ID NO:192), Asn, Asn-Gly, Asn-Gly-Lys, Lys-Ala, Lys-Ala-Ala, Asn-Gly-Lys-Thr (SEQ ID NO:28), Asn-Gly-Lys-Thr-Ala (SEQ ID NO:29), Cys, Cys-Asn, Cys-Asn-Gly, Arg, Arg-Thr, Arg-Thr-Ala, Ser, Cys-Asn-Gly-Lys (SEQ ID NO:30), Cys-Asn-Gly-Lys-Thr (SEQ ID NO:31), Cys-Asn-Gly-Lys-Thr-Ala (SEQ ID NO:32), Ser-Ala, Tyr, Tyr-Cys, Tyr-Cys-Asn, Tyr-Cys-Asn-Gly (SEQ ID NO:33), Tyr-Cys-Asn-Gly-Lys (SEQ ID NO:34), Gln, Gln-Ser, Gln-Ser-Ala, Tyr-Cys-Asn-Gly-Lys-Thr (SEQ ID NO:35), Tyr-Cys-Asn-Gly-Lys-Thr-Ala (SEQ ID NO:36), Asp, Asp-Tyr, Asp-Tyr-Cys, Asp-Tyr-Cys-Asn (SEQ ID NO:37), Asp-Tyr-Cys-Asn-Gly (SEQ ID NO:38), Asp-Tyr-Cys-Asn-Gly-Lys (SEQ ID NO:39), Ile, Ile-Ser, Ile-Ser-Ala, Asp-Tyr-Cys-Asn-Gly-Lys-Thr (SEQ ID NO:40), Arg-Ser, Arg-Ser-Ala, Asp-Tyr-Cys-Asn-Gly-Lys-Thr-Ala (SEQ ID NO:41), Asp-Asp, Asp-Asp-Tyr, Asp-Asp-Tyr-Cys (SEQ ID NO:42), Asp-Asp-Tyr-Cys-Asn (SEQ ID NO:43), Asp-Asp-Tyr-Cys-Asn-Gly (SEQ ID NO:44), Asp-Asp-Tyr-Cys-Asn-Gly-Lys (SEQ ID NO:45), Asp-Asp-Tyr-Cys-Asn-Gly-Lys-Thr (SEQ ID NO:46), Asp-Asp-Tyr-Cys-Asn-Gly-Lys-Thr-Ala (SEQ ID NO:47), Met, Met-Asp, Met-Asp-Asp, Met-Asp-Asp-Tyr (SEQ ID NO:48), Met-Asp-Asp-Tyr-Cys (SEQ ID NO:49), Met-Asp-Asp-Tyr-Cys-Asn (SEQ ID NO:50), Met-Asp-Asp-Tyr-Cys-Asn-Gly (SEQ ID NO:51), Met-Asp-Asp-Tyr-Cys-Asn-Gly-Lys (SEQ ID NO:52), Met-Asp-Asp-Tyr-Cys-Asn-Gly-Lys-Thr (SEQ ID NO:53), Met-Asp-Asp-Tyr-Cys-Asn-Gly-Lys-Thr-Ala (SEQ ID NO:54), Asp-Met, Asp-Met-Asp, Asp-Met-Asp-Asp (SEQ ID NO:55), Asp-Met-Asp-Asp-Tyr (SEQ ID NO:56), Asp-Met-Asp-Asp-Tyr-Cys (SEQ ID NO:57), Asp-Met-Asp-Asp-Tyr-Cys-Asn (SEQ ID NO:58), Asp-Met-Asp-Asp-Tyr-Cys-Asn-Gly (SEQ ID NO:59), Asp-Met-Asp-Asp-Tyr-Cys-Asn-Gly-Lys (SEQ ID NO:60), Asp-Met-Asp-Asp-Tyr-Cys-Asn-Gly-Lys-Thr (SEQ ID NO:61), Asp-Met-Asp-Asp-Tyr-Cys-Asn-Gly-Lys-Thr-Ala (SEQ ID NO:62), A-Cys(R$^1$)-Pro, A-Cys(R$^1$)-Pro-Arg, A-Cys(R$^1$)-Pro-Arg-Asn (SEQ ID NO:193), A-Cys(R$^1$)-Pro-Arg-Asn-Pro (SEQ ID NO:194), A-Cys(R$^1$)-Pro-Arg-Asn-Pro-His (SEQ ID NO:195), A-Cys(R$^1$)-Pro-Arg-Asn-Pro-His-Lys (SEQ ID NO:196), A-Cys(R$^1$)-Pro-Arg-Asn-Pro-His-Lys-Gly (SEQ ID NO:197), A-Cys(R$^1$)-Pro-Arg-Asn-Pro-His-Lys-Gly-Pro (SEQ ID NO:198), A-Cys(R$^1$)-Pro-Arg-Asn-Pro-His-Lys-Gly-Pro-Ala (SEQ ID NO:199), in which A and R$^1$ are as defined above; and X is as defined but is not hydrogen if A and therefore M are absent, is reacted with an amino compound of the formula III

H-Q-Z            III, in which

Z is as defined; and

Q is an amino acid residue or peptide radical selected from a group consisting of B, Cys(R$^1$)-B, Arg-Asn, Arg-Asn-Pro, Asn-Pro, Arg-Asn-Pro-His (SEQ ID NO:63), Asn-Pro-His, Pro-His, Arg-Asn-Pro-His-Lys (SEQ ID NO:65), Asn-Pro-His-Lys (SEQ ID NO:65), Pro-His-Lys, His-Lys, Arg-Asn-Pro-His-Lys-Gly (SEQ ID NO:66), Asn-Pro-His-Lys-Gly (SEQ ID NO:67), Pro-His-Lys-Gly (SEQ ID NO:68), His-Lys-Gly, Lys-Gly, Arg-Asn-Pro-His-Lys-Gly-Pro (SEQ ID NO:69), Asn-Pro-His-Lys-Gly-Pro (SEQ ID NO:70), Pro-His-Lys-Gly-Pro (SEQ ID NO:71), His-Lys-Gly-Pro (SEQ ID NO:72), Lys-Gly-Pro, Gly-Pro, Arg-Asn-Pro-His-Lys-Gly-Pro-Ala (SEQ ID NO:73), Asn-Pro-His-Lys-Gly-Pro-Ala (SEQ ID NO:74), Pro-His-Lys-Gly-Pro-Ala (SEQ ID NO:75), His-Lys-Gly-Pro-Ala (SEQ ID NO:76), Lys-Gly-Pro-Ala (SEQ ID NO:77), Gly-Pro-Ala, Pro-Ala, Arg-Asn-Pro-His-Lys-Gly-Pro-Ala-Thr (SEQ ID NO:78), Asn-Pro-His-Lys-Gly-Pro-Ala-Thr (SEQ ID NO:79), Pro-His-Lys-Gly-Pro-Ala-Thr (SEQ ID NO:80), His-Lys-Gly-Pro-Ala-Thr (SEQ ID NO:81), Lys-Gly-Pro-Ala-Thr (SEQ ID NO:82), Gly-Pro-Ala-Thr (SEQ ID NO:83), Pro-Ala-Thr, Ala-Thr, Gly-Asp-Cys($R^1$)-B, Thr-Gly-Asp-Cys($R^1$)-B (SEQ ID NO:221), Asp-Cys($R^1$)-B, Ala-Asp-Cys($R^1$)-B, Thr-Ala-Asp-Cys($R^1$)-B (SEQ ID NO:200), Lys-Thr-Ala-Asp-Cys($R^1$)-B (SEQ ID NO:201), Gly-Lys-Thr-Ala-Asp-Cys($R^1$)-B (SEQ ID NO:202), Asn-Gly-Lys-Thr-Ala-Asp-Cys($R^1$)-B (SEQ ID NO:203), Asn-Cys($R^1$)-B, Ala-Asn-Cys($R^1$)-B, Thr-Ala-Asn-Cys($R^1$)-B (SEQ ID NO:204), Cys-Asn-Gly-Lys-Thr-Ala-Asp-Cys($R^1$)-B (SEQ ID NO:205), Ala-Ala-Asp-Cys($R^1$)-B (SEQ ID NO:206), Ser-Ala-Asp-Cys($R^1$)-B (SEQ ID NO:207), Tyr-Cys-Asn-Gly-Lys-Thr-Ala-Asp-Cys($R^1$)-B (SEQ ID NO:208), Gly-Cys($R^1$)-B, Ala-Gly-Cys($R^1$)-B, Ser-Ala-Gly-Cys($R^1$)-B (SEQ ID NO:209), Cys(Trt)-Asp-Cys($R^1$)-B, Thr-Cys(Trt)-Asp-Cys($R^1$)-B (SEQ ID NO:210), Lys-Thr-Cys(Trt)-Asp-Cys($R^1$)-B (SEQ ID NO:211), Asp-Tyr-Cys-Asn-Gly-Lys-Thr-Ala-Asp-Cys(Trt)-B (SEQ ID NO:212),Asp-Asp-Tyr-Cys-Asn-Gly-Lys-Thr-Ala-Asp-Cys($R^1$)-B (SEQ ID NO:213) or Met-Asp-Asp-Tyr-Cys-Asn-Gly-Lys-Thr-Ala-Asp-Cys(Trt)-B (SEQ ID NO:214), in which $R^1$ is as defined, and/or in that a free mercapto, hydroxyl or amino group is alkylated and/or a compound of the formula I is converted into one of its salts by treatment with an acid or base.

The residue A is preferably Ac-Asp, Ala-Asp, Thr-Ala-Asp, Lys-Thr-Ala-Asp (SEQ ID NO:1), Ac-Lys-Thr-Ala-Asp (SEQ ID NO:84), Gly-Lys-Thr-Cys-Asp (SEQ ID NO:14), Gly-Lys-Thr-Cys(Trt)-Asp (SEQ ID NO:16), Gly-Lys-Thr-Ala-Asp (SEQ ID NO:7), Lys-Thr-Ala-Asn (SEQ ID NO:2), Lys-Thr-Gly-Asp (SEQ ID NO:3), Lys-Ala-Ala-Asp (SEQ ID NO:4), Arg-Thr-Ala-Asp (SEQ ID NO:5), Gly-Ser-Ala-Asp (SEQ ID NO:222), Ac-Gln-Ser-Ala-Asp (SEQ ID NO:85), le-Ser-Ala-Gly (SEQ ID NO:9) or Arg-Ser-Ala-Gly (SEQ ID NO:10).

B is preferably not present or is, particularly preferably, Ala which may if desired by methylated, Pro, Pro-Arg, Pro-Arg-Asn, Pro-Arg-Asn-Pro (SEQ ID NO:19), Pro-Arg-Asn-Pro-His (SEQ ID NO:20), Pro-Arg-Asn-Pro-His-Lys (SEQ ID NO:21), Pro-Arg-Asn-Pro-His-Lys-Gly (SEQ ID NO:22) or Pro-Arg-Asn-Pro-His-Lys-Gly-Pro-Ala-Thr (SEQ ID NO:23), whereas X is preferably H or acetyl and Z is particularly preferably OH or $NH_2$.

$R^1$ is particularly preferably a triphenylmethyl radical, whereas $R^2$ is preferably methyl but is also preferably, in addition, ethyl, propyl, butyl or tert-butyl.

The radical Ac is preferably acetyl but may also be formyl, propionyl, butyryl, isobutyryl, valeryl, isovaleryl or pivaloyl (trimethylacetyl), or furthermore is preferably aroyl of 7–11 carbon atoms which is optionally substituted by one to three substituents, suitable substituents preferably being one of the following groups: alkyl, alkoxy, alkylthio, alkylsulfinyl or alkylsulfonyl having in each case 1–3, preferably 1 or 2, carbon atoms, methylenedioxy, and also OH, F, Cl, Br, I, $NO_2$, $NH_2$, alkylamino or dialkylamino having in each case 1–3, preferably 1 or 2, carbon atoms in the alkyl group. Individual preferred aroyl radicals are benzoyl, o-, m- or p-tolyl, o-, m- or p-methoxybenzoyl, 2,3-, 2,4-, 2,5-, 2,6-, 3,4- or 3,5-dimethoxybenzoyl, 2,3,4-, 2,3,5-, 2,3,6-, 2,4,5-, 2,4,6- or 3,4,5-trimethoxybenzoyl, o-, m- or p-methylsulfonylbenzoyl, 2,3- or 3,4-methylenedioxybenzoyl, or 1- or 2-naphthoyl. Ac may also be aralkanoyl of 1–10 carbon atoms, for example, phenylacetyl, 2- or 3-phenylpropionyl, 2-, 3- or 4-phenylbutyryl or 2- or 3-phenylisobutyryl.

Accordingly, the invention relates in particular to those compounds of the formula I in which at least one of the radicals or residues mentioned has one of the given meanings, in particular one of the meanings given as preferred.

Some preferred groups of compounds can be represented by the following subformulae Ia to Id, which conform to the formula I and in which the radicals, residues and parameters have the meaning given for formula I unless more closely specified, but in which in Ia Cys($R^1$) is Cys(Trt) and B is Pro;

in Ib Cys($R^1$) is Cys(Trt) and B is Pro-Arg-Asn-Pro-His-Lys-Gly-Pro-Ala-Thr (SEQ ID NO:25);

in Ic Cys($R^1$) is Cys(Trt) and B is Pro-Arg, Pro-Arg-Asn-Pro (SEQ ID NO:19), Pro-Arg-Asn-Pro-His (SEQ ID NO:20), Pro-Arg-Asn-Pro-His-Lys (SEQ ID NO:21) or Pro-Arg-Asn-Pro-His-Lys-Gly (SEQ ID NO:1);

in Id Cys($R^1$) is Cys(Trt) and A is Ala-Asp or Lys-Thr-Ala-Asp.

A further group of preferred compounds can be represented by sub-formulae Iaa to Ida, which otherwise conform to the formula I and to the sub-formulae Ia to Id, but in which additionally X is hydrogen and Z is OH or $NH_2$.

The compounds of the formula I, and also the starting materials for their preparation, are otherwise prepared by known methods, as described in the literature (for example in the standard works such as Houben-Weyl, Methoden der organischen Chemie [Methods of Organic Chemistry], Georg-Thieme-Verlag, Stuttgart), under the reaction conditions which are known and suitable for the reactions mentioned. In this context, use can also be made of known variants which are not mentioned here in any more detail.

If desired, the starting materials can also be formed in situ, so that they are not isolated from the reaction mixture but are reacted further straight away to give the compounds of the formula I.

The compounds of the formula I can be obtained by liberating them from their functional derivatives by solvolysis, in particular hydrolysis, or by hydrogenolysis.

Functional derivatives of amino acids in the compounds of formula I preferably are amino acids which are protected by one of the hydroxy or amino protecting groups discussed below. Preferred protecting groups are, for example, Boc and Fmoc for the N-terminus and OMe and OEt for the C-terminus. Furthermore, if an amino acid residue has a functional group in its side chain, this group could be derivatized, too. The following are examples of derivatized amino acids: Arg(Mtr), Asn(Trt) Asp(OBut), Cys(Trt), Cys(SBut), Gln(Trt), His(Trt), Lys(BOC), Ser(But), Thr(But), Tyr(But), Lys($AcNH_2$), and Lys(AcSH), wherein Ac is —CO—$C_nH_{2n}$— (n=2–12). Furthermore, Asp and Glu can be esterified in their side chains by anchors, as described below.

Preferred starting materials for the solvolysis or hydrogenolysis are those which contain, instead of one or more free amino and/or hydroxyl groups, corresponding, protected amino and/or hydroxyl groups, preferably those which contain, instead of a hydrogen atom attached to a nitrogen atom, an amino-protective group, for example, those which conform to the formula I but contain, instead of an $NH_2$ group, an NHR' group (in which R' is an amino-protective group, e.g., Fmoc, BOC or CBZ).

Further preferred starting materials are those which, instead of the hydrogen atom of a hydroxyl group, carry a hydroxy-protective group, for example, those which conform to the formula I but which contain instead of a hydroxyphenyl group a R"O-phenyl group (in which R" is a hydroxy-protective group).

It is also possible for two or more—identical or different—protected amino and/or hydroxyl groups to be present in the molecule of the starting material. If the protective groups present are different from one another, then in many cases they can be removed selectively. The term "amino-protective group" is generally known and relates to groups which are capable of protecting (blocking) an amino group against chemical reactions, but which are easily removable after the desired chemical reaction has been carried out at other sites of the molecule. In particular, such groups are typically unsubstituted or substituted acyl, aryl, aralkoxymethyl or aralkyl groups. Since the amino-protective groups are removed after the desired reaction (or reaction sequence), their nature and size is incidentally not critical; however, those of 1–20, in particular 1–8, carbon atoms are preferred. The term "acyl group" in the context of the present invention and the present compounds is to be understood in the widest sense. It includes acyl groups derived from aliphatic, araliphatic, aromatic or heterocyclic carboxylic acids or sulfonic acids, and also, in particular, alkoxycarbonyl, aryloxycarbonyl and—in particular— aralkoxycarbonyl groups. Examples of such acyl groups are alkanoyls such as acetyl, propionyl and butyryl; aralkanoyl such as phenylacetyl; aroyl such as benzoyl or tolyl; aryloxyalkanoyl such as POA; alkoxycarbonyl such as methoxycarbonyl, ethoxycarbonyl, 2,2,2-trichloroethoxycarbonyl, BOC, and 2-iodoethoxy-carbonyl; aralkyloxycarbonyl such as CBZ ("carbobenzoxy"), 4-methoxybenzyloxycarbonyl and Fmoc; and arylsulfonyl such as Mtr. Preferred amino-protective groups are BOC and Mtr, and also CBZ, Fmoc, benzyl and acetyl.

The term "hydroxy-protective group" is likewise generally known and relates to groups which are capable of protecting a hydroxyl group against chemical reactions, but which are easily removable after the desired chemical reaction has been carried out at other sites of the molecule. Such groups are typically the above-mentioned unsubstituted or substituted aryl, aralkyl or acyl groups, and also alkyl groups. The nature and size of the hydroxy-protective groups is not critical since they are removed again after the desired chemical reaction or reaction sequence; groups of 1–20, in particular 1–10, carbon atoms are preferred. Examples of hydroxy-protective groups include benzyl, p-nitrobenzoyl, p-toluenesulfonyl and acetyl, with benzyl and acetyl being particularly preferred. The COOH groups in aspartic acid and glutamic acid are preferably protected in the form of their tert-butyl esters (e.g., Asp (OBut)).

The functional derivatives of the compounds of the formula I, to be used as starting materials, can be prepared by conventional methods of amino acid and peptide synthesis, as described in, for example, the standard works and patent applications mentioned, for example, by the solid phase method of Merrifield (B.F. Gysin and R.B. Merrifield, J. Am. Chem. Soc., 94:3102 et seq. (1972)) or more recent, modern variants which are derived therefrom and are known per se.

The liberation of the compounds of the formula I from their functional derivatives is carried out, depending on the protective group used, for example, with strong acids, advantageously with TFA or perchloric acid, or else with other strong inorganic acids such as hydrochloric acid or sulfuric acid, strong organic carboxylic acids, such as trichloroacetic acid, or sulfonic acid such as benzene- or p-toluenesulfonic acid. The presence of an additional inert solvent is possible but not always necessary. Suitable inert solvents are preferably organic acids, for example, carboxylic acids such as acetic acid, ethers such as tetrahydrofuran or dioxane, amides such as DMF, halogenated hydrocarbons such as dichloromethane, and also alcohols such as isopropanol, sec- or tert-butanol, and, in individual cases, methanol or ethanol, and also water. Mixtures of the above-mentioned solvents are also suitable. TFA is preferably used in excess without the addition of a further solvent, while perchloric acid is preferably used in the form of a mixture of acetic acid and 70% strength perchloric acid in the ratio of 9:1. The reaction temperatures for the cleavage are advantageously about 0°–50°, preferably 15°–30° (room temperature).

For example, the groups BOC, But, OBut, Trt and Mtr can be removed preferably with TFA in dichloromethane or with about 3 to 5 n HCl in dioxane at 0°–30°, in which context auxiliary reagents such as anisole, thiophenol or thioanisole may have a favorable effect on the reaction. The removal of the Fmoc group is carried out, for example, using an about 5 to 50% strength solution of dimethylamine, diethylamine, morpholine or piperidine in DMF at 0–300. It is possible here to remove the Trt group selectively from amino acid residues to which it is attached via oxygen, while leaving a Trt group attached via sulfur in the molecule. Likewise, a Trt residue can be introduced subsequently by attaching it preferably to nucleophilic sulfur, while OH groups in the side chain are not substituted.

Protective groups which can be removed by hydrogenolysis (e.g., CBZ or benzyl) can be removed, for example, by treatment with hydrogen in the presence of a catalyst (e.g., a noble metal catalyst such as palladium, advantageously on a support such as charcoal). In this context, suitable solvents are those given above, particular examples being alcohols such as methanol or ethanol, ethers such as THF, carboxylic acids such as acetic acid, water, or amides such as DMF. The hydrogenolysis is generally carried out at temperatures between about 0° and 100° and pressures of between about 1 and 200 bar, preferably at 20–30° and 1–10 bar. For example, hydrogenolysis of the CBZ group is favorably achieved over 5 to 10% Pd-C in methanol or with ammonium formate (instead of $H_2$) over Pd-C in water/DMF at 20–30°.

Compounds of the formula I can also be obtained by reacting a compound of the formula II with an amino compound of the formula III under condensing conditions which are known per se for peptide syntheses, and are described, for example, in Houben-Weyl, loc. cit., Vol. 15/II, pp. 1–806 (1974).

The reaction occurs preferably in the presence of a dehydrating agent, for example, a carbodiimide such as DCCI or EDCI, and also propanephosphonic anhydride (cf. Angew. Chem., 92:129 (1980)), diphenylphosphoryl azide or 2-ethoxy-N-ethoxycarbonyl-1,2-dihydroquinoline in an inert solvent, for example, a halogenated hydrocarbon such as dichloromethane, an ether such as tetrahydrofuran or dioxane, an amide such as DMF or dimethylacetamide, a nitrile such as acetonitrile, or in mixtures of these solvents, at temperatures of about −10–40°, preferably 0°–30°.

Instead of II it is also possible to employ suitable reactive derivatives of these substances in the reaction, for example, those in which reactive groups are blocked intermediately by protective groups. The amino acid derivatives II can be used, for example, in the form of their activated esters which, advantageously, are formed in situ by, for example, addition of HOBt or N-hydroxysuccinimide. However, they can also be employed in the form of their mixed anhydrides, which can be prepared using carboxylic acid halides such as pivaloyl chloride or isobutyloxycarbonyl chloride.

The starting substances of the formula II are generally novel. They can be prepared by known methods, for example, by the methods given above for peptide synthesis and for the removal of protective groups.

In general, synthesis proceeds by first preparing protected peptide esters of the formula R'-M'-OR", e.g., BOC-M-OMe or Fmoc-M-OBut. These are hydrolyzed to give acids of the formula R'-M-OH, for example, BOC-M-OH or Fmoc-M-OH, which are then condensed with a compound of the formula III which, if desired is likewise provided with appropriate protective groups at positions in which reaction is not to take place.

In the case of compounds of the formula IIII, peptide esters of the formula R'-Q-Z'-R", such as BOC-Q-Z'-OMe or Fmoc-Q-Z'-OMe, where Z' is —NH— or —O—, are likewise synthesized and then, before carrying out the condensation for the preparation of compounds of the formula I, the protective group R' is removed in a known manner, Fmoc being removed, for example, by treatment with a piperidine/DMF solution.

It is particularly advantageous to use the more recent methods of peptide synthesis according to modified Merrifield techniques and using peptide synthesis instruments, as are described, for example, in Peptides, Proc. 8th Am. Pept. Symp., Eds. V. Hruby and D.H. Rich, Pierce Comp. III, pp. 73–77 (1983) by A. Jonczyk and J. Meinenhofer (Fmoc strategy), or the techniques given in Angew. Chem., 104:375–391 (1992). Such methods are known per se.

A base of formula I can be converted into the relevant acid addition salt using an acid. Acids which are particularly suitable for this reaction are those which give physiologically acceptable salts. For instance, examples of inorganic acids which can be used are sulfuric acid, nitric acid, hydrohalic acids such as hydrochloric acid or hydrobromic acid, phosphoric acids such as orthophosphoric acid, sulfamic acid, and also organic acids, in particular aliphatic, alicyclic, araliphatic, aromatic or heterocyclic mono- or polybasic carboxylic, sulfonic or sulfuric acids, for example, formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2- or 3-phenylpropionic acid, citric acid, gluconic acid, ascorbic acid, nicotinic acid, isonicotinic acid, methane- or ethanesulfonic acid, ethanedisulfonic acid, 2-hydroxyethanesulfonic acid, naphthalene-mono- and -disulfonic acids, and laurylsulfuric acid. Salts with acids which are not physiologically acceptable, for example, picrates, can be used to isolate and/or purify the compounds of the formula I.

Alternatively, an acid of the formula I can be converted into its physiologically acceptable metal salts or ammonium salts by reaction with a base. In this case, particularly suitable salts are the sodium, potassium, magnesium, calcium and ammonium salts, and also substituted ammonium salts, for example, the dimethyl-, diethyl- or diisopropylammonium salts, monoethanol-, diethanol- or triethanolammonium salts, cyclohexyl- and dicyclohexylammonium salts, dibenzylethylenediammonium salts, and also salts with, for example, N-methyl-D-glucamine or with arginine or lysine.

The novel compounds of the formula I can be used, furthermore, as integrin ligands for the preparation of columns for affinity chromatography, for the isolation of integrins.

In this context, the ligand, i.e., a peptide derivative of the formula I, is coupled covalently to a polymer support via anchor functions.

Suitable polymer support materials are the solid, polymeric phases which are known per se in peptide chemistry and preferably have hydrophilic properties, examples being crosslinked polysugars such as cellulose, Sepharose or SEPHADEX®, acrylamides, polymers based on polyethylene glycol or TENTAKEL® polymers.

Suitable anchor functions which are attached to the polymer supports are preferably linear alkylene chains of 2–12 carbon atoms, in which one end is attached directly to the polymer and the other end carries a functional group such as, for example, hydroxyl, amino, mercapto, maleimido or —COOH, and which are suitable for linking with the C- or N-terminal section of the respective peptide.

In this context it is possible for the peptide to be attached directly or, if desired, via a second anchor function to the anchor of the polymer. It is also possible for peptides containing amino acid residues having functionalized side chains to be attached via the latter to the anchor function of the polymer.

Moreover, it is possible for certain amino acid residues which are a component of the peptides of the formula I to have their side chains modified such that they are available for anchoring, via SH, OH, $NH_2$ or COOH groups, for example, with the anchor of the polymer.

It is possible in this case to use amino acids which are not customary, for example, phenylalanine derivatives which carry a mercapto, hydroxyl, amino or carboxyalkyl chain in position 4 of the phenyl ring, the functional group being at the end of the chain.

Examples of amino acid residues whose side chain can be used directly as an anchor function are Lys, Orn, Arg, Asp, Asn, Glu, Gln, Ser, Thr, Cys or Tyr.

Examples of N-terminal anchors are radicals such as, for example, —CO—$C_nH_{2n}$—$NH_2$, —CO—$C_nH_{2n}$—OH, —CO—$C_nH_{2n}$—SH or —CO—$C_nH_{2n}$—COOH where n=2–12, the length of the alkylene chain not being critical; it is also possible, if desired, for this chain to be replaced in whole or in part by, for example, appropriate aryl or alkylaryl radicals.

Examples of possible C-terminal anchors are —O—$C_nH_{2n}$—SH, —O—$C_nH_{2n}$—OH, —O—$C_nH_{2n}$—$NH_2$, —O—$C_nH_{2n}$—COOH, —NH—$C_nH_{2n}$—SH, —NH—$C_nH_{2n}$—OH, —NH—$C_nH_{2n}$—$NH_2$ or —NH—$C_nH_{2n}$—COOH, n and the alkylene chain both being subject to what was stated in the previous paragraph.

The N- and C-terminal anchors can also be used as the anchor component for an amino acid residue side chain which is already functionalized. Examples of suitable amino acid residues in this case are Lys(CO-$C_5H_{10}$-$NH_2$), Asp(NH-$C_3H_6$-COOH) or Cys($C_3H_6$-$NH_2$), the anchor always being attached to the functional group of the side chain.

The preparation of the materials for affinity chromatography is carried out under conditions as are conventional and known per se for the condensation of amino acids and which have already been described in the section relating to the preparation of the compounds of the formula I, and which are described in Pierce, Immuno Technology Catalog & Handbook (1990).

The novel compounds of the formula I, and their physiologically acceptable salts, may be used for preparing pharmaceutical preparations by bringing them into a suitable dosage form together with at least one excipient or auxiliary and, if desired, together with one or more additional active substances. The formulations thus obtained can be employed as medicaments in human or veterinary medicine. Suitable substances as excipients are organic or inorganic substances which are suitable for enteral (e.g., oral or rectal), parenteral (e.g., intravenous injection) or local (e.g., topical, dermal, ophthalmic or nasal) administration or for administration in the form of an inhalation spray and which do not react with the novel compounds, examples being water or aqueous isotonic saline solution, lower alcohols, vegetable oils, benzyl alcohols, polyethylene glycols, glycerol triacetate and other fatty acid glycerides, gelatin, soya lecithin, carbohydrates such as lactose or starch, magnesium stearate, talc, cellulose and petroleum jelly.

Oral administration forms are, in particular, tablets, film-coated tablets, capsules, syrups, juices or drops; coated tablets and capsules with gastric juice-resistant coatings or capsule casings are of special interest. Suppositories can be used for rectal administration, while parenteral administration employs solutions, preferably oily or aqueous solutions, and also suspensions, emulsions or implants. Examples of forms suitable for topical administration are solutions, which may be used in the form of eye drops, and further examples are suspensions, emulsions, creams, ointments or compresses. For administration as an inhalation spray, sprays can be used which contain the active substance either dissolved or suspended in a propellant gas or propellant gas mixture (e.g., $CO_2$ or fluorochlorohydrocarbons or appropriate substitutes). In this case, the active substance is expediently used in micronized form, it being possible for one or more additional, physiologically tolerated solvents to be present, e.g., ethanol. Inhalation solutions can be administered using customary inhalers. The novel compounds may also be lyophilized and the resulting lyophilizates can be used, for example, for producing injection preparations. In this context, the injections may be given as a bolus or as a continuous infusion (e.g., intravenous, intramuscular, subcutaneous or intrathecal). The given formulations can be sterilized and/or may contain auxiliaries, such as preservatives, stabilizers and/or wetting agents, emulsifiers, salts for influencing the osmotic pressure, buffer substances, colorants and/or fragrances. They may, if desired, also contain one or more further active substances, for example, one or more vitamins.

The substances according to the invention can generally be administered in analogy to other known and commercially available peptides, but in particular in analogy to the compounds described in U.S. Pat. No. 4,472,305, preferably in dosages of about 0.05–500 mg, in particular 0.5–100 mg, per dosage unit. The daily dose is preferably about 0.01–2 mg/kg of body weight. The specific dose for each particular patient depends, however, on a wide variety of factors, for example, on the effectiveness of the specific compound employed, on the age, body weight, general state of health, gender, on the diet, on the time and route of administration, on the rate of excretion, on the combination of medicaments and the severity of the respective disease to which the therapy is applied. Parenteral administration is preferred.

Suitable preparations for using the compounds as antimicrobial agents are, for example, injection vials, ampoules, solutions, and capsules. Carriers, excipients, and further additives are mentioned in Examples A–H. The amount of the inventive compounds in the antimicrobial agents is preferably about 0.05–500 mg per dosage unit.

All temperatures above and below are given in °C. In the examples which follow, "customary work-up" means: water is added if necessary, the mixture is neutralized, extracted with dichloromethane, the phases are separated, the organic phase is dried over sodium sulfate, filtered, concentrated by evaporation and purified by chromatography on silica gel and/or crystallization. "Customary purification" denotes that the peptide is precipitated from $TFA/CH_2Cl_2$ using diethyl ether, after which gel filtration is carried out in aqueous buffers and/or ion exchange chromatography is carried out. Rt=retention time (minutes) for HPLC on LICHROSORB RP® select B (250–4.7 mm) column, eluent: 0.3% TFA in water; isopropanol gradient of 0–80 vol. % in 50 min. at a flow rate of 1 ml/min, and detection at 215 nm. $M^+$=molecular peak in the mass spectrum obtained by the "fast atom bombardment" (FAB) method, generally representing $M^++H$, in other words the mass of the respective compound increased by 1 mass unit.

DMPP resin is 4-(2',4'-dimethoxyphenylhydroxymethyl) phenoxy resin, a super-acid-labile resin which permits the synthesis of peptides with protected side chains.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, and of corresponding German application P 43 36 758.5, filed Oct. 28, 1994, are hereby incorporated by reference.

EXAMPLES

Example 1

0.6 g of Fmoc-Pro-OH is dissolved in 100 ml of dichloromethane, 1.2 equivalents of Wang resin (p-benzyloxybenzyl alcohol resin) are added, and the mixture is stirred at room temperature for 12 hours. After removal of the solvent Fmoc-Pro-Wang resin is obtained. In a peptide synthesizer Fmoc-Cys(Trt)-OH is condensed with H-Pro-Wang resin [liberation from Fmoc-Pro-Wang resin using piperidine/DMF (20% strength)], using a three-fold excess of the protected cysteine. The coupling is carried out at room temperature in DCCI/HOBt, to give Fmoc-Cys(Trt)-Pro-Wang resin. Subsequent treatment with piperidine/DMF (20% strength) again gives H-Cys(Trt)-Pro-Wang resin.

Example 2

In analogy to Example 1 and starting from Fmoc-Gly-DMPP resin, by condensation with Fmoc-Ala-OH, Fmoc-Ser(But)-OH and Fmoc-Ile-OH in the sequence given in a peptide synthesizer (continuous flow principle), after carrying out the following steps:

liberation of H-Gly-DMPP resin using piperidine/DMF (20%)

washing with dimethylacetamide (DMA)

reaction with Fmoc-Ala-OH in DCCI/HOBt at room temperature washing and treatment with piperidine/DMF (20%)

coupling of the resulting H-Ala-Gly-DMPP resin with Fmoc-Ser(But)-OH washing and treatment of the resulting Fmoc-Ser(But)-Ala-Gly-DMPP resin with $CF_3SO_3H/CH_2Cl_2/H_2O$, Fmoc-Ser(But)-Ala-Gly-OH is obtained.

Example 3

By analogy with Example 2, starting from Fmoc-Asn(Trt)-DMPP resin and after carrying out the appropriate reaction steps, Fmoc-Lys(Boc)-Thr(But)-Ala-Asn(Trt)-OH (SEQ ID NO:87)

is obtained by coupling with Fmoc-Ala-OH, Fmoc-Thr(But)-OH and Fmoc-Lys(Boc)-OH in the specified sequence. By analogy with Example 2, starting from Fmoc-Asp(OBut)-DMPP resin and after carrying out the appropriate reaction steps, the following are obtained:

Fmoc-Lys(Boc)-Thr(But)-Gly-Asp(OBut)-OH (SEQ ID NO:86)

by coupling with Fmoc-Gly-OH, Fmoc-Thr(But)-OH and Fmoc-Lys(Boc)-OH in the specified sequence;

Fmoc-Lys(Boc)-Ala-Ala-Asp(OBut)-OH (SEQ ID NO:88)

by coupling with Fmoc-Ala-OH, Fmoc-Ala-OH and Fmoc-Lys(Boc)-OH in the specified sequence;

Fmoc-Arg(Mtr)-Thr(But)-Ala-Asp(OBut)-OH (SEQ ID NO:89)

by coupling with Fmoc-Ala-OH, Fmoc-Thr(But)-OH and Fmoc-Arg(Mtr)-OH in the specified sequence;

Fmoc-Ser(But)-Ala-Asp(OBut)-OH by coupling with Fmoc-Ala-OH and Fmoc-Ser(But)-OH in the specified sequence;

Fmoc-Lys(Boc)-Thr(But)-Ala-Asp(OBut)-OH (SEQ ID NO:90)

by coupling with Fmoc-Ala-OH, Fmoc-Thr(But)-OH and Fmoc-Lys(Boc)-OH in the specified sequence;

Fmoc-Gln(Trt)-Ser(But)-Ala-Asp(OBut)-OH (SEQ ID NO:91)

by coupling with Fmoc-Ala-OH, Fmoc-Ser(But)-OH and Fmoc-Gln(Trt)-OH in the specified sequence.

Example 5

0.4 g of H-Cys(Trt)-Pro-Wang resin are condensed in a peptide synthesizer (continuous flow principle) with Fmoc-Lys(Boc)-Thr(But)-Ala-Asn(Trt)-OH (SEQ ID NO:87), using a three-fold excess of the Fmoc peptide. The coupling is carried out at room temperature in DCCI/HOBt, to give Fmoc-Lys(Boc)-Thr(But)-Ala-Asn(Trt)-Cys(Trt)-Pro-Wang (SEQ ID NO:223) resin. Subsequent treatment with TFA/$CH_2Cl_2$ followed by removal of the Fmoc group with piperidine/DMF (20%) gives H-Lys-Thr-Ala-Asn-Cys(Trt)-Pro-OH (SEQ ID NO:92).

The following are obtained analogously by condensation of H-Cys(Trt)-Pro-Wang resin with Fmoc-Lys(Boc)-Thr(But)-Ala-Asp(Trt)-OH (SEQ ID NO:90):

H-Lys-Thr-Ala-Asp-Cys(Trt)-Pro-OH (SEQ ID NO:93); Rt=28.9; $M^+$=876;

with Fmoc-Lys(Boc)-Ala-Ala-Asp(Trt)-OH (SEQ ID NO:88):

H-Lys-Ala-Ala-Asp-Cys(Trt)-Pro-OH (SEQ ID NO:94);

with Fmoc-Arg(Mtr)-Thr(But)-Ala-Asp(Trt)-OH (SEQ ID NO:89):

H-Arg-Thr-Ala-Asp-Cys(Trt)-Pro-OH (SEQ ID NO:95);

with Fmoc-Ser(But)-Ala-Asp(Trt)-OH:

H-Ser-Ala-Asp-Cys(Trt)-Pro-OH (SEQ ID NO:96);

with Fmoc-Gln(Trt)-Ser(But)-Ala-Asp(Trt)-OH (SEQ ID NO:91):

H-Gln-Ser-Ala-Asp-Cys(Trt)-Pro-OH (SEQ ID NO:97);

with Fmoc-Glp-Ser(But)-Ala-Asp(Trt)-OH (SEQ ID NO:224):

H-Glp-Ser-Ala-Asp-Cys(Trt)-Pro-OH (SEQ ID NO:98);

with Fmoc-Lys(Boc)-Thr(But)-Ala-Asp(Trt)-OH (SEQ ID NO:90):

H-Lys-Thr-Ala-Asp-Cys(Trt)-Pro-OH (SEQ ID NO:93);

with Fmoc-Ile-Ser(But)-Ala-Gly-OH (SEQ ID NO:225):

H-Ile-Ser-Ala-Gly-Cys(Trt)-Pro-OH (SEQ ID NO:99);

with Fmoc-Arg(Mtr)-Ser(But)-Ala-Gly-OH (SEQ ID NO:226):

H-Arg-Ser-Ala-Gly-Cys(Trt)-Pro-OH (SEQ ID NO:100);

with Fmoc-Lys(Boc)-Gly-Gly-Asp(Trt)-OH (SEQ ID NO:227):

H-Lys-Gly-Gly-Asp-Cys(Trt)-Pro-OH (SEQ ID NO:101).

Example 6

By a nalogy wi th Example 5, starting from H-Cys(Trt)-Wang resin and by condensation with Fmoc-Lys(Boc)-Thr(But)-Ala-Asp(OBut)-OH (SEQ ID NO:96) in a peptide synthesizer, Fmoc-Lys(Boc)-Thr(But)-Ala-Asp(OBut)-Cys(Trt)-Wang (SEQ ID NO:102) resin is obtained which, after treatment with TFA/$CH_2Cl_2$ followed by removal of the Fmoc group using piperidine/DMF (20%) and conventional purification gives H-Lys-Thr-Ala-Asp-Cys(Trt)-OH (SEQ ID NO:103); Rt=28.8; $M^+$=779.

Example 7

1.2 g of Boc-Thr(But)-Ala-Asp(OBut)-Cys-Pro-Arg(Mtr)-OH (SEQ ID NO:123) are dissolved in a mixture of 150 ml of dichloromethane and 20 ml of DMF, the mixture is cooled to 0°, and then 0.5 g of DCCl, 0.3 g of HOBt, 0.23 ml of N-methylmorpholine and one equivalent of H-Asn(Trt)-Pro-His(Trt)-Lys(Boc)-Gly-Pro-Ala-Thr(But)-OMe (SEQ ID NO:104) [both peptides can be obtained by methods of the modified Merrifield technique] are added. The mixture is stirred at 0° C. for 20 hours and at room temperature for 6 hours. The reaction mixture is concentrated, treated with an ion exchanger and placed in an aqueous $NaHCO_3$ solution. The product which precipitates is filtered off with suction and washed with water. After crystallization from ethylacetate/petroleumether, BOC-Thr(But)-Ala-Asp(OBut)-Cys-Pro-Arg(Mtr)-Asn(Trt)-Pro-His(Trt)-Lys(Boc)-Gly-Pro-Ala-Thr(But)-OMe (SEQ ID NO:112) is obtained.

The following are obtained analogously by condensation:
of BOC-Gly-Lys(Boc)-Thr(But)-Cys(Trt)-Asp(OBut)-OH (SEQ ID NO:105) with H-Cys(Trt)-Pro-Arg(Mtr)-Asn (Trt)-Pro-His(Trt)-Lys(Boc)-Gly-Pro-Ala-Thr(But)-OMe (SEQ ID NO:106):

BOC-Gly-Lys(Boc)-Thr(But)-Cys(Trt)-Asp(OBut)-Cys(Trt)-Pro-Arg(Mtr)-Asn(Trt)-Pro-His(Trt)-Lys(Boc)-Gly-Pro-Ala-Thr-(But)-OMe (SEQ ID NO:107);

of BOC-Lys(Boc)-Thr(But)-Ala-Asp(OBut)-Cys(Trt)-OH (SEQ ID NO:108)with H-Pro-Arg(Mtr)-Asn(Trt)-Pro-His(Trt)-Lys(Boc)-Gly-OMe (SEQ ID NO:109):

BOC-Lys(Boc)-Thr(But)-Ala-Asp(OBut)-Cys(Trt)-Pro-Arg (Mtr)-Asn(Trt)-Pro-His(Trt)-Lys(Boc)-Gly-OMe (SEQ ID NO:110).

Example 8

0.3 g of BOC-Thr(But)-Ala-Asp(OBut)-Cys-Pro-Arg (Mtr)-Asn(Trt)-Pro-His(Trt)-Lys(Boc)-Gly-Pro-Ala-Thr (But)-OMe (SEQ ID NO:111) is dissolved in 30 ml of methanol; 1.5 ml of 2N NaOH solution are added and the mixture is stirred at 250 for 4 hours. After removal of the solvent, the residue is taken up in water, the pH is adjusted to 3 by adding diluted HCL and the product is extracted with ethyl acetate. The extract is dried over $Na_2SO_4$. After removal of the solvent, BOC-Thr(But)-Ala-Asp(OBut)-Cys-Pro-Arg(Mtr)-Asn(Trt)-Pro-His(Trt)-Lys(Boc)-Gly-Pro-Ala-Thr(But)-OH (SEQ ID NO:112) is obtained, which is taken up in 20 ml of 2N Hcl in dioxane and stirred at room temperature for 2 hours. The reaction mixture is concentrated to dryness and the residue is taken up in $TFA/CH_2Cl_2$, precipitated with $Et_2O$ and purified by RP-H PLC, to give H-Thr-Ala-Asp-Cys-Pro-Arg-Asn-Pro-His-Lys-Gly-Pro-Ala-Thr-OH (SEQ ID NO:113); Rt=12.6; $M^+$=1465.

The following are obtained analogously by removal of the protective groups, starting from the compounds of Example 7:

H-Gly-Lys-Thr-Cys-Asp-Cys-Pro-Arg-Asn-Pro-His-Lys-Gly-Pro-Ala-Thr-OH (SEQ ID NO:114); Rt=13.1; M+=1681;

H-Lys-Thr-Ala-Asp-Cys-Pro-Arg-Asn-Pro-His-Lys-Gly-OH (SEQ ID NO:115).

Example 9

By analogy with Example 1, starting from H-Thr(But)-Wang resin and by condensation with Fmoc-Ala-OH, Fmoc-Pro-OH, Fmoc-Gly-OH, Fmoc-Lys(Boc)-OH, Fmoc-His(Trt)-OH and Fmoc-Pro-OH in the specified sequence in a peptide synthesizer (continuous flow principle) after repeating the steps indicated above, Fmoc-Pro-His(Trt)-Lys(Boc)-Gly-Pro-Ala-Thr(But)-Wang (SEQ ID NO:116) resin is obtained, which is treated again with piperidine/DMF (20%) to give H-Pro-His(Trt)-Lys(Boc)-Gly-Pro-Ala-Thr(But)-Wang (SEQ ID NO:117) resin.

Example 10

By analogy with Example 1, starting from H-Gly-Wang resin and by condensation with Fmoc-Lys(Boc)-OH, Fmoc-His(Trt)-OH and Fmoc-Pro-OH, in the specified sequence in a peptide synthesizer (continuous flow principle) after repeating the steps indicated above, Fmoc-Pro-His(Trt)-Lys(Boc)-Gly-Wang (SEQ ID NO:118) resin is obtained, which is then treated again with piperidine/DMF (20%) to give H-Pro-His(Trt)-Lys(Boc)-Gly-Wang (SEQ ID NO:119) resin.

Example 11

By analogy with Example 2, starting from Fmoc-Asn(Trt)-Wang resin and after carrying out the appropriate reaction steps:

Fmoc-Ala-Asp(OBut)-Cys(Trt)-Pro-Arg(Mtr)-Asn(Trt)-OH (SEQ ID NO:120)

is obtained by coupling with Fmoc-Arg(Mtr)-OH, Fmoc-Pro-OH, Fmoc-Cys(Trt)-OH, Fmoc-Asp(OBut)-OH and Fmoc-Ala-OH in the specified sequence.

Analogously, starting from Fmoc-Asn(Trt)-Wang resin,

Fmoc-Lys(Boc)-Thr(But)-Ala-Asp(OBut)-Cys(Trt)-Pro-Arg(Mtr)-Asn(Trt)-OH (SEQ ID NO:138)

is obtained by coupling with Fmoc-Arg(Mtr)-OH, Fmoc-Pro-OH, Fmoc-Cys(Trt)-OH, Fmoc-Asp(OBut)-OH, Fmoc-Ala-OH, Fmoc-Thr(But)-OH and Fmoc-Lys(Boc)-OH in the specified sequence;

Fmoc-Gly-Lys(Boc)-Thr(But)-Cys(Trt)-Asp(OBut)-Cys(Trt)-Pro-Arg(Mtr)-Asn(Trt)-OH (SEQ ID NO:141)

is obtained by coupling with Fmoc-Arg(Mtr)-OH, Fmoc-Pro-OH, Fmoc-Cys(Trt)-OH, Fmoc-Asp(OBut)-OH, Fmoc-Cys(Trt)-OH, Fmoc-Thr(But)-OH, Fmoc-Lys(Boc)-OH and Fmoc-Gly-OH in the specified sequence;

Fmoc-Ala-Asp(OBut)-Cys(Trt)-Pro-Arg(Mtr)-Asn(Trt)-OH (SEQ ID NO:134)

is obtained by coupling with Fmoc-Arg(Mtr)-OH, Fmoc-Pro-OH, Fmoc-Cys(Trt)-OH, Fmoc-Asp(OBut)-OH and Fmoc-Ala-OH in the specified sequence;

Fmoc-Gly-Lys(Boc)-Thr(But)-Ala-Asp(OBut)-Cys(Trt)-Pro-Arg-(Mtr)-Asn(Trt)-OH (SEQ ID NO:144)

is obtained by coupling with Fmoc-Arg(Mtr)-OH, Fmoc-Pro-OH, Fmoc-Cys(Trt)-OH, Fmoc-Asp(OBut)-OH, Fmoc-Ala-OH, Fmoc-Thr(But)-OH, Fmoc-Lys(Boc)-OH and Fmoc-Gly-OH in the specified sequence; and Fmoc-Thr(But)-Ala-Asp(OBut)-Cys(Trt)-Pro-Arg(Mtr)-Asn-(Trt)-OH (SEQ ID NO:125)

is obtained by coupling with Fmoc-Arg(Mtr)-OH, Fmoc-Pro-OH, Fmoc-Cys(Trt)-OH, Fmoc-Asp(OBut)-OH, Fmoc-Ala-OH and Fmoc-Thr(But)-OH in the specified sequence.

Example 12

By analogy with Example 5, by condensation of H-Pro-His(Trt)-Lys(Boc)-Gly-Pro-Ala-Thr(But)-Wang (SEQ ID NO:126) resin with Fmoc-Ala-Asp(OBut)-Cys(Trt)-Pro-Arg(Mtr)-Asn(Trt)-OH (SEQ ID NO:127), Fmoc-Ala-Asp(OBut)-Cys(Trt)-Pro-Arg(Mtr)-Asn(Trt)-Pro-His(Trt)-Lys(Boc)-Gly-Pro-Ala-Thr(But)-Wang (SEQ ID NO:135) resin is obtained. Subsequent treatment with $TFA/CH_2Cl_2$ followed by removal of the Fmoc group with piperidine/DMF (20%) gives:

H-Ala-Asp-Cys(Trt)-Pro-Arg-Asn-Pro-His-Lys-Gly-Pro-Ala-Thr-OH (SEQ ID NO:136); Rt=25.6; $M^+$=1606.

The following are obtained analogously by condensation:

of H-Pro-His(Trt)-Lys(Boc)-Gly-Pro-Ala-Thr(But)-Wang (SEQ ID NO:137) resin with Fmoc-Lys(Boc)-Thr(But)-Ala-Asp(OBut)-Cys(Trt)-Pro-Arg(Mtr)-Asn(Trt)-OH (SEQ ID NO:138):

H-Lys-Th r-Ala-Asp-Cys(Trt)-Pro-Arg-Asn-Pro-His-Lys-Gy-Pro-Ala-Thr-OH (SEQ ID NO:139); Rt=24.6; $M^+$=1835;

of H-Pro-His(Trt)-Lys(Boc)-Gly-Pro-Ala-Thr(But)-Wang (SEQ ID NO:140) resin with Fmoc-Gly-Lys(Boc)-Thr (But)-Cys(Trt)-Asp (O But)-Cys(Trt)-Pro-Arg(Mtr)-Asn(Trt)-OH (SEQ ID NO:141):

H-Gly-Lys-Thr-Cys(Trt)-Asp-Cys(Trt)-Pro-Arg-Asn-Pro-His-Lys-Gly-Pro-Ala-Thr-OH (SEQ ID NO:142); Rt=30.8; $M^+$=2167;

of H-Pro-His(Trt)-Lys-(Boc)-Gly-Wang (SEQ ID NO:143) resin with Fmoc-Gly-Lys (Boc)-Thr(But)-Ala-Asp(OBut)-Cys(Trt)-Pro-Arg(Mtr)-Asn (Trt)-OH (SEQ ID NO:144):

H-Gly-Lys-Thr-Ala-Asp-Cys(Trt)-Pro-Arg-Asn-Pro-His-Lys-Gly-OH (SEQ ID NO:145); Rt=24.5; M⁺=1623;

of H-Pro-His(Trt)-Lys(Boc)-Gly-Pro-Ala-Thr(But)-Wang (SEQ ID NO:117) resin with Fmoc-Thr(But)-Ala-Asp (OBut)-Cys(Trt)-Pro-Arg(Mtr)-Asn(Trt)-OH (SEQ ID NO:147):

H-Thr-Ala-Asp-Cys-Pro-Arg-Asn-Pro-His-Lys-Gly-Pro-Ala-Thr-OH (SEQ ID NO:148); Rt=24.9; M⁺=1707.

Example 13

By analogy with Examples 7 and 8, the following are obtained by condensation and subsequent hydrolysis and removal of the BOC protective group, starting from H-Pro-His(Trt)-Lys(Boc)-Gly-Pro-Ala-Thr(But)-OMe (SEQ ID NO:149) with Boc-Ala-Asp(OBut)-Cys (Trt)-Pro-Arg(Mtr)-Asn(Trt)-OH (SEQ ID NO:150):

H-Ala-Asp-Cys-Pro-Arg-Asn-Pro-His-Lys-Gly-Pro-Ala-Thr-OH (SEQ ID NO:151); Rt=13.1; M⁺=1362;

from H-Pro-His(Trt)-Lys(Boc)-Gly-OMe (SEQ ID NO:152) with Boc-Ala-Asp(OBut)-Cys(Trt)-Pro-Arg (Mtr)-Asn(Trt)-OH (SEQ ID NO:153):

H-Ala-Asp-Cys-Pro-Arg-Asn-Pro-His-Lys-Gly-OH (SEQ ID NO:154); Rt=10.6; M⁺=1094;

from H-Pro-His(Trt)-Lys(Boc)-Gly-OMe (SEQ ID NO:155) with Boc-Gly-Lys(Boc)-Thr(But)-Ala-Asp (OBut)-Cys(Trt)-Pro-Arg(Mtr)-Asn(Trt)-OH (SEQ ID NO:156):

H-Gly-Lys-Thr-Ala-Asp-Cys-Pro-Arg-Asn-Pro-His-Lys-Gly-OH (SEQ ID NO:157); Rt=11.4; M⁺=1380;

from H-Pro-His(Trt)-Lys(Boc)-Gly-Pro-Ala-Thr(But)-OMe (SEQ ID NO:158) with Boc-Lys(Boc)-Thr(But)-Ala-Asp(OBut)-Cys(Trt)-Pro-Arg(Mtr)-Asn(Trt)-OH (SEQ ID NO:228):

H-Lys-Thr-Ala-Asp-Cys-Pro-A rg-Asn-Pro-H is-Lys-Gly-Pro-Ala-Thr-OH (SEQ ID NO:159); Rt=12.7; M⁺=1592.

Example 14

By analogy with Example 2, the following are obtained starting from Fmoc-Asp(OBut)-DMPP resin, after carrying out the appropriate reaction steps:

by coupling with Fmoc-Ala-OH, Fmoc-Thr(But)-OH and Fmoc-Lys(Boc)-OH in the specified sequence:

Fmoc-Lys(Boc)-Thr(But)-Ala-Asp(OBut)-OH (SEQ ID NO:90).

The following are obtained analogously, starting from Fmoc-Cys(Trt)-DMPP resin:

by coupling with Fmoc-Asp(OBut)-OH in the specified sequence:

Fmoc-Asp(OBut)-Cys(Trt)-OH;

by coupling with Fmoc-Asp(OBut)-OH and Fmoc-Ala-OH in the specified sequence:

Fmoc-Ala-Asp(OBut)-Cys(Trt)-OH;

by coupling with Fmoc-Asp(OBut)-OH, Fmoc-Ala-OH and Fmoc-Thr(But)-OH in the specified sequence:

Fmoc-Thr(But)-Ala-Asp(OBut)-Cys(Trt)-OH (SEQ ID NO:128).

Example 15

By analogy with Example 1, starting from H-Pro-Wang resin and by condensation with Fmoc-Asn(Trt)-OH, Fmoc-Arg(Mtr)-OH, Fmoc-Pro-OH and Fmoc-Cys(Trt)-OH in the specified sequence in a peptide synthesizer (continuous flow principle), after repeating the steps indicated above, Fmoc-Cys(Trt)-Pro-Arg(Mtr)-Asn(Trt)-Pro-Wang (SEQ ID NO:129) resin is obtained, which is retreated with piperidine/DMF (20%) to give H-Cys(Trt)-Pro-Arg(Mtr)-Asn(Trt)-Pro-Wang (SEQ ID NO:130) resin.

The following are obtained analogously starting from Fmoc-Lys(Boc)-Wang resin by coupling with Fmoc-His (Trt)-OH, Fmoc-Pro-OH, Fmoc-Asn(Trt)-OH, Fmoc-Arg (Mtr)-OH, Fmoc-Pro-OH, and Fmoc-Cys(Trt)-OH in the specified sequence:

H-Cys(Trt)-Pro-Arg(Mtr)-Asn(Trt)-Pro-His(Trt)-Lys(Boc)-Wang (SEQ ID NO:131) resin;

from Fmoc-His(Trt)-Wang resin by coupling with Fmoc-Pro-OH, Fmoc-Asn(Trt)-OH, Fmoc-Arg(Mtr)-OH, Fmoc-Pro-OH and Fmoc-Cys(Trt)-OH in the specified sequence:

H-Cys(Trt)-Pro-Arg(Mtr)-Asn(Trt)-Pro-His(Trt)-Wang (SEQ ID NO:132) resin;

from Fmoc-Gly-Wang resin by coupling with Fmoc-Lys (Boc)-OH, Fmoc-His(Trt)-OH, Fmoc-Pro-OH, Fmoc-Asn(Trt)-OH, Fmoc-Arg(Mtr)-OH, Fmoc-Pro-OH and Fmoc-Cys(Trt)-OH in the specified sequence:

H-Cys(Trt)-Pro-Arg(Mtr)-Asn(Trt)-Pro-His(Trt)-Lys(Boc)-Gly-Wang (SEQ ID NO:133) resin;

from Fmoc-Arg(Mtr)-Wang resin by coupling with Fmoc-Pro-OH and Fmoc-Cys(Trt)-OH in the specified sequence:

H-Cys(Trt)-Pro-Arg(Mtr)-Wang resin;

from Fmoc-Ala-Wang resin by coupling with Fmoc-Cys (Trt)-OH:

H-Cys(Trt)-Ala-Wang resin.

Example 16

By analogy with Example 5, by condensation of Fmoc-Lys(Boc)-Thr(But)-Ala-Asp(OBut)-OH (SEQ ID NO:90) with H-Cys(Trt)-Pro-Arg(Mtr)-Asn(Trt)-Pro-Wang (SEQ ID NO:130) resin, Fmoc-Lys(Boc)-Thr(But)-Ala-Asp (OBut)-Cys(Trt)-Pro-Arg(Mtr)-Asn(Trt)-Pro-Wang (SEQ ID NO:121) resin is obtained. Subsequent treatment with TFA/CH$_2$Cl$_2$ followed by removal of the Fmoc group with piperidine/DMF (20%) gives:

H-Lys-Thr-Ala-Asp-Cys(Trt)-Pro-Arg-Asn-Pro-OH (SEQ ID NO:160); Rt=25.4; M⁺=1243.

The following are obtained by condensation of Fmoc-Lys(Boc)-Thr(But)-Ala-Asp(OBut)-OH (SEQ ID NO:90) with H-Cys(Trt)-Pro-Arg(Mtr)-Asn(Trt)-Pro-His(Trt)-Lys(Boc)-Wang (SEQ ID NO:131) resin:

H-Lys-Thr-Ala-Asp-Cys(Trt)-Pro-Arg-Asn-Pro-His-Lys-OH (SEQ ID NO:161); Rt=23.6; M⁺=1509;

of Fmoc-Lys(Boc)-Thr(But)-Ala-Asp(OBut)-OH (SEQ ID NO:90) with H-Cys(Trt)-Pro-Arg(Mtr)-Asn(Trt)-Pro-His(Trt)-Wang (SEQ ID NO:132) resin:

H-Lys-Thr-Ala-Asp-Cys(Trt)-Pro-Arg-Asn-Pro-His-OH (SEQ ID NO:215); Rt=24.3; M⁺=1380;

of Fmoc-Lys(Boc)-Thr(But)-Ala-Asp(OBut)-OH (SEQ ID NO:90) with H-Cys(Trt)-Pro-Arg(Mtr)-Asn(Trt)-Pro-H is(Trt)-Lys(Boc)-Gly-Wang (SEQ ID NO:133) resin:

H-Lys-Thr-Ala-Asp-Cys(Trt)-Pro-Arg-Asn-Pro-His-Lys-Gly-OH (SEQ ID NO:185); Rt 23.7; M⁺=1565;

of Fmoc-Lys(Boc)-Thr(But)-Ala-Asp(OBut)-OH (SEQ ID NO:90) with H-Cys(Trt)-Pro-Arg(Mtr)-Wang resin:

H-Lys-Thr-Ala-Asp-Cys(Trt)-Pro-Arg-OH (SEQ ID NO:162); Rt=25.7; M⁺=1032;

of Fmoc-Asp(OBut)-Cys(Trt)-OH with H-Pro-Arg(Mtr)-Asn(Trt)-Pro-His(Trt)-Lys(Boc)-Wang (SEQ ID NO:216) resin:

H-Asp-Cys(Trt)-Pro-Arg-Asn-Pro-His-Lys-OH (SEQ ID NO:163);

of Fmoc-Ala-Asp(OBut)-Cys(Trt)-OH with H-Pro-Arg (Mtr)-Wang resin:

H-Ala-Asp-Cys(Trt)-Pro-Arg-OH (SEQ ID NO:164); Rt=27.4; M⁺=803;

of Fmoc-Thr(But)-Ala-Asp(OBut)-Cys(Trt)-OH (SEQ ID NO:128) with H-Pro-Arg(Mtr)-Wang resin:

H-Thr-Ala-Asp-Cys(Trt)-Pro-Arg-OH (SEQ ID NO:165); Rt=27.3; M⁺=904;

of Fmoc-Lys(Boc)-Thr(But)-Ala-Asp(OBut)-OH (SEQ ID NO:90) with H-Cys(Trt)-Pro-Wang resin:

H-Lys-Thr-Ala-Asp-Cys(Trt)-Pro-OH (SEQ ID NO:93).

Example 17

0.9 g of H-Cys(Trt)-Pro-Arg-Asn-Pro-His-Lys(BOC)-DMPP (SEQ ID NO:217) resin [prepared as in Example 1] is dissolved in 100 ml of dichloromethane, condensed with H₃-CO-Asp-OH by analogy with Example 2, and worked up. Reintroduction of the Trt group using triphenylmethanol gives H₃C-CO-Asp-Cys(Trt)-Pro-Arg-Asn-Pro-His-Lys-OH (SEQ ID NO:166); Rt=26.0; M⁺=1250.

The following are obtained analogously, starting from H-Thr-Ala-Asp-Cys(Trt)-Pro-OH (SEQ ID NO:167) with H₃C-CO-Lys(BOC)-OH:

H₃C-CO-Lys-Thr-Ala-Asp-Cys(Trt)-Pro-OH (SEQ ID NO:168);

from H-Ser-Ala-Asp-Cys(Trt)-Pro-OH (SEQ ID NO:96) with H₃CO-Gln(Trt)-OH:

H₃C-CO-Gln-Ser-Ala-Asp-Cys(Trt)-Pro-OH (SEQ ID NO:169).

Example 18

0.7 g of Fmoc-Cys(Trt)-Pro-OH is dissolved in 100 ml of dichloromethane; 1.4 equivalents of MBHA resin, 1.4 equivalents of HOBt and 1.4 equivalents of DCC are added, and the mixture is stirred at room temperature for 24 hours. After removal of the solvent, Fmoc-Cys(Trt)-Pro-MBHA resin is obtained. By treatment (at room temperature for 1 hour) with piperidine/DMF (20%) this gives H-Cys(Trt)-Pro-MBHA resin, which is subsequently coupled with Fmoc-Lys(Boc)-Thr(But)-Ala-Asp(OBut)-OH (SEQ ID NO:90) by adding the three-fold excess of this compound. The coupling is carried out at room temperature in DCCI/HOBt, to give Fmoc-Lys(Boc)-Thr(But)-Ala-Asp(OBut)-Cys(Trt)-Pro-MBHA (SEQ ID NO:218) resin. Subsequent retreatment with piperidine/DMF (20%) gives H-Lys(Boc)-Thr(But)-Ala-Asp(OBut)-Cys(Trt)-Pro-MBHA (SEQ ID NO:219) resin.

The resulting compound is taken up in 20 ml of TFA and stirred at room temperature for 2 hours. Conventional purification gives H-Lys-Thr-Ala-Asp-Cys(Trt)-Pro-NH₂ (SEQ ID NO:178).

The following peptide amides are obtained analogously, by reacting the free peptides with MBHA resin and then removing the resin:

H-Lys-Thr-Ala-Asp-Cys(Trt)-Pro-Arg-Asn-Pro-His-Lys-NH₂ (SEQ ID NO:172);

H-Lys-Thr-Ala-Asp-Cys(Trt)-Pro-Arg-Asn-Pro-His-N H₂ (SEQ ID NO:170);

H-Lys-Thr-Ala-Asp-Cys(Trt)-Pro-Arg-Asn-Pro-His-Lys-Gly-N H₂ (SEQ ID NO:173);

H-Lys-Thr-Ala-Asp-Cys(Trt)-Pro-Arg-NH₂ (SEQ ID NO:174);

H-Asp-Cys(Trt)-Pro-Arg-Asn-Pro-His-Lys-NH₂ (SEQ ID NO:175);

H-Ala-Asp-Cys(Trt)-Pro-Arg-NH₂ (SEQ ID NO:176);

H-Thr-Ala-Asp-Cys(Trt)-Pro-Arg-NH₂ (SEQ ID NO:177);

H-Lys-Thr-Ala-Asp-Cys(Trt)-Pro-NH₂ (SEQ ID NO:171).

Example 19

By analogy with Example 17, by condensation of H-Thr-Ala-Asp-Cys(Trt)-Pro-NH₂ (SEQ ID NO:179) with H₃C-CO-Lys(BOC)-OH followed by removal of the BOC group, H₃C-CO-Lys-Thr-Ala-Asp-Cys(Trt)-Pro-NH₂ (SEQ ID NO:180) is obtained.

The following are obtained analogously:

H₃C-CO-Lys-Thr-Ala-Asp-Cys(Trt)-Pro-Arg-Asn-Pro-His-Lys-NH₂ (SEQ ID NO:181);

H₃C-CO-Lys-Thr-Ala-Asp-Cys(Trt)-Pro-Arg-Asn-Pro-His-Lys-Gly-NH₂ (SEQ ID NO:220);

H₃C-CO-Lys-Thr-Ala-Asp-Cys(Trt)-Pro-Arg-NH₂ (SEQ ID NO:182);

H₃C-CO-Thr-Ala-Asp-Cys(Trt)-Pro-Arg-NH₂ (SEQ ID NO:183);

H₃C-CO-Lys-Thr-Ala-Asp-Cys(Trt)-Pro-NH₂ (SEQ ID NO:180).

Example 20

By analogy with Example 5, by condensation of Fmoc-Lys(Boc)-Thr(But)-Ala-Asp(OBut)-OH (SEQ ID NO:90) with H-Cys(Trt)-NMeAla-Wang resin, Fmoc-Lys(Boc)-Thr(But)-NMeAla-Wang resin is obtained. Subsequent treatment with TFA/CH₂Cl₂ followed by removal of the Fmoc group with piperidine/DMF (20%) gives:

H-Lys-Thr-Ala-Thr-Cys(Trt)-NMeAla-OH (SEQ ID NO:184).

Example 21

0.2 g of H-Lys-Thr-Ala-Asp-Cys-Pro-Arg-Asn-Pro-His-Lys-Gly-OH (SEQ ID NO:115) is dissolved in 30 ml of $CH_2Cl_2$ and 30 ml of TFA, and 1.2 equivalents of triphenylmethyl alcohol are added thereto at room temperature. The mixture is subsequently stirred for an hour and the peptide formed is precipitated, after concentration, by addition of diethyl ether. Conventional purification gives H-Lys-Thr-Ala-Asp-Cys(Trt)-Pro-Arg-Asn-Pro-His-Lys-Gly-OH (SEQ ID NO:186); Rt=23.7; $M^+$=1565.

The following are obtained analogously by alkylation of H-Lys-Thr-Ala-Asp-Cys-Pro-Arg-Asn-Pro-His-Lys-Gly-OH (SEQ ID NO:115):

- with methyl iodide: H-Lys-Thr-Ala-Asp-Cys(Me)-Pro-Arg-Asn-Pro-His-Lys-Gly-OH (SEQ ID NO:187); Rt=9.8; $M^+$=1338;
- with ethyl iodide: H-Lys-Thr-Ala-Asp-Cys(Et)-Pro-Arg-Asn-Pro-His-Lys-Gly-OH (SEQ ID NO:188); Rt=10.4; $M^+$=1352;
- with benzyl chloride: H-Lys-Thr-Ala-Asp-Cys(Bzl)-Pro-Arg-Asn-Pro-His-Lys-Gly-OH (SEQ ID NO:189); Rt=13.8; $M^+$=1415;
- with tert-butyl chloride: H-Lys-Thr-Ala-Asp-Cys(tBu)-Pro-Arg-Asn-Pro-His-Lys-Gly-OH (SEQ ID NO:190); Rt=12.3; $M^+$=1379;
- with diphenylmethyl chloride: H-Lys-Thr-Ala-Asp-Cys(Dpm)-Pro-Arg-Asn-Pro-His-Lys-Gly-OH (SEQ ID NO:191); Rt=17.8; $M^+$=1489.

The examples below related to pharmaceutical formulations.

Example A: Injection Vials

A solution of 100 g of an active substance of the formula I and 5 g of disodium hydrogen phosphate in 3 l of double-distilled water is adjusted to a pH of 6.5 using 2N hydrochloric acid, sterilized by filtration, used to fill injection vials and then lyophilized under sterile conditions, and the vials are sealed under sterile conditions. Each injection vial contains 5 mg of active substance.

Example B: Suppositories

A mixture of 20 g of an active substance of the formula I together with 100 g of soya lecithin and 1400 g of cocoa butter is melted, poured into molds and left to cool. Each suppository contains 20 mg of active substance.

Example C: Solution

A solution is prepared from 1 g of an active substance of the formula I, 9.38 g of $NaH_2PO_4 \times 2H_2O$, 28.48 g of $Na_2HPO_4 \times 12\ H_2O$ and 0.1 g of benzalconium chloride in 940 ml of double-distilled water. The solution is adjusted to a pH of 6.8, made up to 1 l and sterilized by irradiation. This solution can be used in the form of eye drops.

Example D: Ointment 500 mg of an active substance of the formula I is mixed with 99.5 g of petroleum jelly under aseptic conditions.

Example E: Tablets

A mixture of 1 kg of active substance of formula 1, 4 kg of lactose, 1.2 kg of potato starch, 0.2 kg of talc and 0.1 kg of magnesium stearate is compressed in a customary manner to form tablets such that each tablet contains 10 mg of active substance.

Example F: Coated Tablets

By analogy with Example E, tablets are molded, and are then coated in a conventional manner with a coating comprising saccharose, potato starch, talc, tragacanth and colorant.

Example G: Capsules

Hard gelatin capsules are filled, in a customary manner, with 2 kg of active substance of the formula I, so that each capsule contains 20 mg of the active substance.

Example H: Ampoules

A solution of 1 kg of active substance of the formula I in 60 l of double-distilled water is filtered sterile, dispensed into ampoules and lyophilized under sterile conditions, and the ampoules are sealed under sterile conditions. Each ampoule contains 10 mg of active substance.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

---

What is claimed is:

1. A linear peptide of formula I

X-A-Cys(R$^1$)-B-Z     I, wherein

X is H or Ac, wherein Ac is $C_{1-10}$-alkanoyl, $C_{8-10}$-aralkanoyl or $C_{7-11}$-aroyl;

A is absent or is Asp or a peptide fragment selected from a group consisting of Ala-Asp, Thr-Ala-Asp, Lys-Thr-Ala-Asp (SEQ ID NO:1), Lys-Thr-Ala-Asn(SEQ ID NO:2), Lys-Thr-Gly-Asp (SEQ ID NO:3), Lys-Ala-Ala-Asp (SEQ ID NO:4), Arg-Thr-Ala-Asp (SEQ ID NO:5), Ser-Ala-Asp, Gln-Ser-Ala-Asp (SEQ ID NO:6), Gly-Lys-Thr-Ala-Asp (SEQ ID NO:7), Asn-Gly-Lys-Thr-Ala-Asp (SEQ ID NO:8), Ile-Ser-Ala-Gly (SEQ ID NO:9), Arg-Ser-Ala-Gly (SEQ ID NO:10), Cys-Asn-Gly-Lys-Thr-Ala-Asp (SEQ ID NO:11), Tyr-Cys-Asn-Gly-Lys-Thr-Ala-Asp (SEQ ID NO:12), Asp-Tyr-Cys-Asn-Gly-Lys-Thr-Ala-Asp (SEQ ID NO:13), Gly-Lys-Thr-Cys-Asp (SEQ ID NO:14), Asp-Asp-Tyr-Cys-Asn-Gly-Lys-Thr-Ala-Asp (SEQ ID NO:15), Gly-Lys-Thr-Cys(Trt)-Asp (SEQ ID NO:16), Met-Asp-Asp-Tyr-Cys-Asn-Gly-Lys-Thr-Ala-Asp (SEQ ID NO:17) and Asp-Met-Asp-Asp-Tyr-Cys-Asn-Gly-Lys-Thr-Ala-Asp (SEQ ID NO:18);

B is absent or is Ala, Arg, Asn, Asp, Cys, Gln, Glu, Gly, His, Ile, Leu, Lys, Met, Orn, Phe, 4-Hal-Phe, Pro, Ser, Thr, Trp, Tyr or Val or is an N-methylated derivative of the amino acid residues mentioned, or is a peptide fragment selected from the group consisting of Pro-Arg, Pro-Arg-Asn, Pro-Arg-Asn-Pro (SEQ ID NO:19), Pro-Arg-Asn-Pro-His (SEQ ID NO:20), Pro-Arg-Asn-Pro-His-Lys (SEQ ID NO:21), Pro-Arg-Asn-Pro-His-Lys-Gly (SEQ ID NO:22), Pro-Arg-Asn-Pro-His-Lys-Gly-Pro (SEQ ID NO:23), Pro-Arg-Asn-Pro-His-Lys-Gly-Pro-Ala (SEQ ID NO:24) and Pro-Arg-Asn-Pro-His-Lys-Gly-Pro-Ala-Thr (SEQ ID NO:25), in which only one of the residues A or B can be absent;

Z is OH, OR$^2$, NH$_2$, NHR$^2$ or NR$_2^2$;

R$^1$ is H, R$^2$, Trt, Dpm or Bzl;

R$^2$ is $C_{1-6}$-alkyl; and

Hal is F, Cl, Br or I, or a physiologically acceptable salt thereof.

2. A peptide of claim 1, having 4–17 amino acid residues.

3. A peptide of claim 1 selected from the group consisting of:

(a) H-Ala-Asp-Cys(Trt)-Pro-Arg-Asn-Pro-His-Lys-Gly-Pro-Ala-Thr-OH;

(b) H-Lys-Thr-Ala-Asp-Cys(Trt)-Pro-Arg-Asn-Pro-His-Lys-Gly-Pro-Ala-Thr-OH;

(c) H-Gly-Lys-Thr-Ala-Asp-Cys(Trt)-Pro-Arg-Asn-Pro-His-Lys-Gly-OH;

(d) H-Lys-Thr-Ala-Asp-Cys(Trt)-Pro-Arg-Asn-Pro-His-OH;

(e) H-Lys-Thr-Ala-Asp-Cys(Trt)-Pro-Arg-Asn-Pro-His-Lys-Gly-OH;

(f) H-Lys-Thr-Ala-Asp-Cys(Trt)-Pro-Arg-OH;

(g) H-Lys-Thr-Ala-Asp-Cys(Trt)-Pro-OH; and (h) H$_3$C-CO-Asp-Cys(Trt)-Pro-Arg-Asn-Pro-His-Lys-OH.

4. A process for the preparation of a peptide of claim 1 or a salt thereof, comprising:

liberating said peptide from one of its functional derivatives by treatment with a solvolyzing or hydrogenolyzing agent, or reacting a compound of formula II

X-M-OH     II, wherein

M is an amino acid residue or peptide radical selected from a group consisting of A, A-Cys(R$^1$), Ala, Thr, Thr-Ala, Lys, Lys-Thr, Lys-Thr-Ala, Gly, Lys-Thr-Ala-Gly, Gly-Lys, Gly-Lys-Thr, Gly-Lys-Thr-Ala, Gly-Lys-Thr-Cys(R$^1$), Asn, Asn-Gly, Asn-Gly-Lys, Lys-Ala, Lys-Ala-Ala, Asn-Gly-Lys-Thr, Asn-Gly-Lys-Thr-Ala, Cys, Cys-Asn, Cys-Asn-Gly, Arg, Arg-Thr, Arg-Thr-Ala, Ser, Cys-Asn-Gly-Lys, Cys-Asn-Gly-Lys-Thr, Cys-Asn-Gly-Lys-Thr-Ala, Ser-Ala, Tyr, Tyr-Cys, Tyr-Cys-Asn, Tyr-Cys-Asn-Gly, Tyr-Cys-Asn-Gly-Lys, Gin, Gln-Ser, Gln-Ser-Ala, Tyr-Cys-Asn-Gly-Lys-Thr, Tyr-Cys-Asn-Gly-Lys-Thr-Ala, Asp, Asp-Tyr, Asp-Tyr-Cys, Asp-Tyr-Cys-Asn, Asp-Tyr-Cys-Asn-Gly, Ile, Ile-Ser, Ile-Ser-Ala, Asp-Tyr-Cys-Asn-Gly-Lys, Asp-Tyr-Cys-Asn-Gly-Lys-Thr, Arg-Ser, Arg-Ser-Ala, Asp-Tyr-Cys-Asn-Gly-Lys-Thr-Ala, Asp-Asp, Asp-Asp-Tyr, Asp-Asp-Tyr-Cys, Asp-Asp-Tyr-Cys-Asn, Asp-Asp-Tyr-Cys-Asn-Gly, Asp-Asp-Tyr-Cys-Asn-Gly-Lys, Asp-Asp-Tyr-Cys-Asn-Gly-Lys-Thr, Asp-Asp-Tyr-Cys-Asn-Gly-Lys-Thr-Ala, Met, Met-Asp, Met-Asp-Asp, Met-Asp-Asp-Tyr, Met-Asp-Asp-Tyr-Cys, Met-Asp-Asp-Tyr-Cys-Asn, Met-Asp-Asp-Tyr-Cys-Asn-Gly, Met-Asp-Asp-Tyr-Cys-Asn-Gly-Lys, Met-Asp-Asp-Tyr-Cys-Asn-Gly-Lys-Thr, Met-Asp-Asp-Tyr-Cys-Asn-Gly-Lys-Thr-Ala, Asp-Met, Asp-Met-Asp, Asp-Met-Asp-Asp, Asp-Met-Asp-Asp-Tyr, Asp-Met-Asp-Asp-Tyr-Cys, Asp-Met-Asp-Asp-Tyr-Cys- Asn, Asp-Met-Asp-Asp-Tyr-Cys-Asn-Gly, Asp-Met-Asp-Asp-Tyr-Cys-Asn-Gly-Lys, Asp-M et-Asp-Asp-Tyr-Cys-Asn-Gly-Lys-Thr, Asp-Met-Asp-Asp-Tyr-Cys-Asn-Gly-Lys-Thr-Ala, A-Cys($R^1$)-Pro, A-Cys($R^1$)-Pro-Arg, A-Cys($R^1$)-Pro-Arg-Asn, A-Cys($R^1$)-Pro-Arg-Asn-Pro, A-Cys($R^1$)-Pro-Arg-Asn-Pro-His, A-Cys($R^1$)-Pro-Arg-Asn-Pro-His-Lys, A-Cys($R^1$)-Pro-Arg-Asn-Pro-His-Lys-Gly, A-Cys($R^1$)-Pro-Arg-Asn-Pro-His-Lys-Gly-Pro, A-Cys($R^1$)-Pro-Arg-Asn-Pro-His-Lys-Gly-Pro-Ala, in which A and $R^1$ are as defined in claim 1, and X is as defined but is not hydrogen if A and therefore M are absent, with an amino compound of the formula III $$H-Q-Z \qquad \text{III,}$$

wherein

Z is as defined and

Q is an amino acid residue or peptide radical selected from a group consisting of B, Cys($R^1$)-B, Arg-Asn, Arg-Asn-Pro, Asn-Pro, Arg-Asn-Pro-His, Asn-Pro-His, Pro-His, Arg-Asn-Pro-His-Lys, Asn-Pro-His-Lys, Pro-His-Lys, His-Lys, Arg-Asn-Pro-His-Lys-Gly, Asn-Pro-His-Lys-Gly, Pro-His-Lys-Gly, His-Lys-Gly, Lys-Gly, Arg-Asn-Pro-His-Lys-Gly-Pro, Asn-Pro-His-Lys-Gly-Pro, Pro-His-Lys-Gly-Pro, His-Lys-Gly-Pro, Lys-Gly-Pro, Gly-Pro, Arg-Asn-Pro-His-Lys-Gly-Pro-Ala, Asn-Pro-His-Lys-Gly-Pro-Ala, Pro-His-Lys-Gly-Pro-Ala, His-Lys-Gly-Pro-Ala, Lys-Gly-Pro-Ala, Gly-Pro-Ala, Pro-Ala, Arg-Asn-Pro-His-Lys-Gly-Pro-Ala-Thr, Asn-Pro-His-Lys-Gly-Pro-Ala-Thr, Pro-His-Lys-Gly-Pro-Ala-Thr, His-Lys-Gly-Pro-Ala-Thr, Lys-Gly-Pro-Ala-Thr, G -Pro-Ala-Thr, Pro-Ala-Thr, Ala-Thr, Gly-Asp-Cys($R^1$)-B, Thr-Gly-Asp-Cys($R^1$)-B, Asp-Cys($R^1$)-B, Ala-Asp-Cys($R^1$)-B, Thr-Ala-Asp-Cys($R^1$)-B, Lys-Thr-Ala-Asp-Cys($R^1$)-B, Gly-Lys-Thr-Ala-Asp-Cys($R^1$)-B, Asn-Gly-Lys-Thr-Ala-Asp-Cys($R^1$)-B, Asn-Cys($R^1$)-B, Ala-Asn-Cys($R^1$)-B, Thr-Ala-Asn-Cys($R^1$)-B, Cys-Ala-Gly-Lys-Thr-Ala-Asp-Cys($R^1$)-B, Ala-Ala-Asp-Cys($R^1$)-B, Ser-Ala-Asp-Cys($R^1$)-B, Tyr-Cys-Asn-Gly-Lys-Thr-Ala-Asp-Cys($R^1$)-B, Gly-Cys($R^1$)-B, Ala-Gly-Cys($R^1$)-B, Ser-Ala-Gly-Cys($R^1$)-B, Cys(Trt)-Asp-Cys($R^1$)-B, Thr-Cys(Trt)-Asp-Cys($R^1$)-B, Lys-Thr-Cys(Trt)-Asp-Cys($R^1$)-B, Asp-Tyr-Cys-Asn-Gly-Lys-Thr-Ala-Asp-Cys($R^1$)-B, Asp-Asp-Tyr-Cys-Asn-Gly-Lys-Thr-Ala-Asp-Cys($R^1$)-B or Met-Asp-Asp-Tyr-Cys-Asn-Gly-Lys-Thr-Ala-Asp-Cys($R^1$)-B, wherein $R^1$ is as defined, and/or alkylating a free mercapto, hydroxyl or amino group and/or converting a peptide into a salt thereof by treatment with an acid or base.

5. A peptide of claim 1, which has a chiral center and occurs in enantiomeric forms.

6. A peptide of claim 5, wherein the enantiomer is in the D form.

7. A peptide of claim 5, wherein the enantiomer is in the L form.

8. A peptide of claim 1, wherein A is Ac-Asp, Ala-Asp, Thr-Ala-Asp, Lys-Thr-Ala-Asp, Ac-Lys-Thr-Ala-Asp, Gly-Lys-Thr-Cys-Asp, Gly-Lys-Thr-Cys(Trt)-Asp, Gly-Lys-Thr-Ala-Asp, Lys-Thr-Ala-Asn, Lys-Thr-Gly-Asp, Lys-Ala-Ala-Asp, Arg-Thr-Ala-Asp, Gly-Ser-Ala-Asp, Ac-Gln-Ser-Ala-Asp, Ile-Ser-Ala-Gly or Arg-Ser-Ala-Gly.

9. A peptide of claim 1, wherein B is not present or is Ala, optionally methylated, Pro, Pro-Arg, Pro-Arg-Asn, Pro-Arg-Asn-Pro, Pro-Arg-Asn-Pro-His, Pro-Arg-Asn-Pro-His-Lys, Pro-Arg-Asn-Pro-His-Lys-Gly or Pro-Arg-Asn-Pro-His-Lys-Gly-Pro-Ala-Thr.

10. A peptide of claim 1, wherein X is H or acetyl.

11. A peptide of claim 1, wherein Z is OH or $NH_2$.

12. A peptide of claim 1, wherein $R^1$ is triphenylmethyl.

13. A peptide of claim 1, wherein $R^2$ is methyl, ethyl, propyl, butyl or tert-butyl.

14. A peptide of claim 1, wherein Ac is acetyl, formyl, propionyl, butyryl, isobutyryl, valeryl, isovaleryl or pivaloyl, $C_{7-11}$-aroyl optionally sub-stituted 1–3 times by $C_{1-3}$-alkyl, -alkoxy, -alkylthio, -alkylsulfinyl or -alkylsulfonyl, methylenedioxy, OH, F, Cl, Br, I, $NO_2$, $NH_2$, $C_{1-3}$-alkylamino or $C_{2-6}$-dialkylamino.

15. A pharmaceutical preparation comprising a peptide of claim 1, and a pharmaceutically acceptable excipient.

16. A pharmaceutical preparation of claim 5, wherein the amount of the peptide is 0.05 to 500 mg per dosage.

17. A method of treating thrombosis, cardiac infarction, stroke, osteoporosis, arteriosclerosis, inflammation or a tumor, comprising administering to a patient in need of such treatment a peptide of claim 1.

18. A method of inhibiting tumor cells from metastasizing, comprising exposing said tumor cells to a peptide of claim 1.

19. A method of inhibiting the binding of fibrinogen to $\beta_3$-integrin receptor, comprising administering a peptide of claim 1.

20. A method of inhibiting thrombocyte aggregation, comprising administering a peptide of claim 1.

21. A method of claim 17, wherein said peptide is administered in a daily dosage of 0.01–2 mg/kg of body weight.

22. A method for the purification of integrins by affinity chromatography, comprising introducing a sample containing integrins into a chromatographic column, said column containing a polymeric support to which a peptide of claim 1 is bonded directly or via an anchor function.

* * * * *

SEQUENCE LISTING ( 1 ) GENERAL INFORMATION:

( i i i ) NUMBER OF SEQUENCES: 228

( 2 ) INFORMATION FOR SEQ ID NO: 1:

( i ) SEQUENCE CHARACTERISTICS:

( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: YES -continued (iv) ANTI-SENSE: NO (v) FRAGMENT TYPE: N-terminal (xi) SEQUENCE DESCRIPTION: SEQ ID NO: 1:

Lys Thr Ala Asp
1

(2) INFORMATION FOR SEQ ID NO: 2:

(i) SEQUENCE CHARACTERISTICS:
       (A) LENGTH: 4 amino acids
       (B) TYPE: amino acid
       (C) STRANDEDNESS: single
       (D) TOPOLOGY: linear (ii) MOLECULE TYPE: peptide (iii) HYPOTHETICAL: YES (iv) ANTI-SENSE: NO (v) FRAGMENT TYPE: N-terminal (xi) SEQUENCE DESCRIPTION: SEQ ID NO: 2:

Lys Thr Ala Asn
1

(2) INFORMATION FOR SEQ ID NO: 3:

(i) SEQUENCE CHARACTERISTICS:
       (A) LENGTH: 4 amino acids
       (B) TYPE: amino acid
       (C) STRANDEDNESS: single
       (D) TOPOLOGY: linear (ii) MOLECULE TYPE: peptide (iii) HYPOTHETICAL: YES (iv) ANTI-SENSE: NO (v) FRAGMENT TYPE: N-terminal (xi) SEQUENCE DESCRIPTION: SEQ ID NO: 3:

Lys Thr Gly Asp
1

(2) INFORMATION FOR SEQ ID NO: 4:

(i) SEQUENCE CHARACTERISTICS:
       (A) LENGTH: 4 amino acids
       (B) TYPE: amino acid
       (C) STRANDEDNESS: single
       (D) TOPOLOGY: linear (ii) MOLECULE TYPE: peptide (iii) HYPOTHETICAL: YES (iv) ANTI-SENSE: NO (v) FRAGMENT TYPE: N-terminal (xi) SEQUENCE DESCRIPTION: SEQ ID NO: 4:

Lys Ala Ala Asp
1

(2) INFORMATION FOR SEQ ID NO: 5:

(i) SEQUENCE CHARACTERISTICS:

(A) LENGTH: 4 amino acids
(B) TYPE: amino acid
(C) STRANDEDNESS: single
(D) TOPOLOGY: linear (ii) MOLECULE TYPE: peptide (iii) HYPOTHETICAL: YES (iv) ANTI-SENSE: NO (v) FRAGMENT TYPE: N-terminal (xi) SEQUENCE DESCRIPTION: SEQ ID NO: 5:

Arg Thr Ala Asp
1

(2) INFORMATION FOR SEQ ID NO: 6:

(i) SEQUENCE CHARACTERISTICS:
(A) LENGTH: 4 amino acids
(B) TYPE: amino acid
(C) STRANDEDNESS: single
(D) TOPOLOGY: linear (ii) MOLECULE TYPE: peptide (iii) HYPOTHETICAL: YES (iv) ANTI-SENSE: NO (v) FRAGMENT TYPE: N-terminal (xi) SEQUENCE DESCRIPTION: SEQ ID NO: 6:

Gln Ser Ala Asp
1

(2) INFORMATION FOR SEQ ID NO: 7:

(i) SEQUENCE CHARACTERISTICS:
(A) LENGTH: 5 amino acids
(B) TYPE: amino acid
(C) STRANDEDNESS: single
(D) TOPOLOGY: linear (ii) MOLECULE TYPE: peptide (iii) HYPOTHETICAL: YES (iv) ANTI-SENSE: NO (v) FRAGMENT TYPE: N-terminal (xi) SEQUENCE DESCRIPTION: SEQ ID NO: 7:

Gly Lys Thr Ala Asp
1               5

(2) INFORMATION FOR SEQ ID NO: 8:

(i) SEQUENCE CHARACTERISTICS:
(A) LENGTH: 6 amino acids
(B) TYPE: amino acid
(C) STRANDEDNESS: single
(D) TOPOLOGY: linear (ii) MOLECULE TYPE: peptide (iii) HYPOTHETICAL: YES (iv) ANTI-SENSE: NO (v) FRAGMENT TYPE: N-terminal (xi) SEQUENCE DESCRIPTION: SEQ ID NO: 8:

```
Asn Gly Lys Thr Ala Asp
 1               5
```

(2) INFORMATION FOR SEQ ID NO: 9:

(i) SEQUENCE CHARACTERISTICS:
      (A) LENGTH: 4 amino acids
      (B) TYPE: amino acid
      (C) STRANDEDNESS: single
      (D) TOPOLOGY: linear (ii) MOLECULE TYPE: peptide (iii) HYPOTHETICAL: YES (iv) ANTI-SENSE: NO (v) FRAGMENT TYPE: N-terminal (xi) SEQUENCE DESCRIPTION: SEQ ID NO: 9:

```
Ile Ser Ala Gly
 1
```

(2) INFORMATION FOR SEQ ID NO: 10:

(i) SEQUENCE CHARACTERISTICS:
      (A) LENGTH: 4 amino acids
      (B) TYPE: amino acid
      (C) STRANDEDNESS: single
      (D) TOPOLOGY: linear (ii) MOLECULE TYPE: peptide (iii) HYPOTHETICAL: YES (iv) ANTI-SENSE: NO (v) FRAGMENT TYPE: N-terminal (xi) SEQUENCE DESCRIPTION: SEQ ID NO: 10:

```
Arg Ser Ala Gly
 1
```

(2) INFORMATION FOR SEQ ID NO: 11:

(i) SEQUENCE CHARACTERISTICS:
      (A) LENGTH: 7 amino acids
      (B) TYPE: amino acid
      (C) STRANDEDNESS: single
      (D) TOPOLOGY: linear (ii) MOLECULE TYPE: peptide (iii) HYPOTHETICAL: YES (iv) ANTI-SENSE: NO (v) FRAGMENT TYPE: N-terminal (xi) SEQUENCE DESCRIPTION: SEQ ID NO: 11:

```
Cys Asn Gly Lys Thr Ala Asp
 1               5
```

(2) INFORMATION FOR SEQ ID NO: 12:

(i) SEQUENCE CHARACTERISTICS:
      (A) LENGTH: 8 amino acids
      (B) TYPE: amino acid
      (C) STRANDEDNESS: single
      (D) TOPOLOGY: linear (ii) MOLECULE TYPE: peptide ( i i i ) HYPOTHETICAL: YES ( i v ) ANTI-SENSE: NO ( v ) FRAGMENT TYPE: N-terminal ( x i ) SEQUENCE DESCRIPTION: SEQ ID NO: 12:

Tyr Cys Asn Gly Lys Thr Ala Asp
1               5

( 2 ) INFORMATION FOR SEQ ID NO: 13:

( i ) SEQUENCE CHARACTERISTICS:
      ( A ) LENGTH: 9 amino acids
      ( B ) TYPE: amino acid
      ( C ) STRANDEDNESS: single
      ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( x i ) SEQUENCE DESCRIPTION: SEQ ID NO: 13:

Asp Tyr Cys Asn Gly Lys Thr Ala Asp
1               5

( 2 ) INFORMATION FOR SEQ ID NO: 14:

( i ) SEQUENCE CHARACTERISTICS:
      ( A ) LENGTH: 5 amino acids
      ( B ) TYPE: amino acid
      ( C ) STRANDEDNESS: single
      ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( x i ) SEQUENCE DESCRIPTION: SEQ ID NO: 14:

Gly Lys Thr Cys Asp
1               5

( 2 ) INFORMATION FOR SEQ ID NO: 15:

( i ) SEQUENCE CHARACTERISTICS:
      ( A ) LENGTH: 10 amino acids
      ( B ) TYPE: amino acid
      ( C ) STRANDEDNESS: single
      ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: linear ( x i ) SEQUENCE DESCRIPTION: SEQ ID NO: 15:

Asp Asp Tyr Cys Asn Gly Lys Thr Ala Asp
1               5                   10

( 2 ) INFORMATION FOR SEQ ID NO: 16:

( i ) SEQUENCE CHARACTERISTICS:
  ( A ) LENGTH: 5 amino acids
  ( B ) TYPE: amino acid
  ( C ) STRANDEDNESS: single
  ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
  ( A ) NAME/KEY: Modified-site
  ( B ) LOCATION:4
  ( D ) OTHER INFORMATION:/product="Cys-Trityl"
      / note="S-Trityl"

( x i ) SEQUENCE DESCRIPTION: SEQ ID NO: 16:

Gly Lys Thr Cys Asp
1           5

( 2 ) INFORMATION FOR SEQ ID NO: 17:

( i ) SEQUENCE CHARACTERISTICS:
  ( A ) LENGTH: 11 amino acids
  ( B ) TYPE: amino acid
  ( C ) STRANDEDNESS: single
  ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( x i ) SEQUENCE DESCRIPTION: SEQ ID NO: 17:

Met Asp Asp Tyr Cys Asn Gly Lys Thr Ala Asp
1               5                   10

( 2 ) INFORMATION FOR SEQ ID NO: 18:

( i ) SEQUENCE CHARACTERISTICS:
  ( A ) LENGTH: 12 amino acids
  ( B ) TYPE: amino acid
  ( C ) STRANDEDNESS: single
  ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( x i ) SEQUENCE DESCRIPTION: SEQ ID NO: 18:

Asp Met Asp Asp Tyr Cys Asn Gly Lys Thr Ala Asp
1               5                   10

( 2 ) INFORMATION FOR SEQ ID NO: 19:

( i ) SEQUENCE CHARACTERISTICS:
  ( A ) LENGTH: 4 amino acids
  ( B ) TYPE: amino acid
  ( C ) STRANDEDNESS: single
  ( D ) TOPOLOGY: linear ( i i ) MOLECULE TYPE: peptide (iii) HYPOTHETICAL: YES (iv) ANTI-SENSE: NO (v) FRAGMENT TYPE: N-terminal (xi) SEQUENCE DESCRIPTION: SEQ ID NO: 19:

Pro Arg Asn Pro
1

(2) INFORMATION FOR SEQ ID NO: 20:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (iii) HYPOTHETICAL: YES (iv) ANTI-SENSE: NO (v) FRAGMENT TYPE: N-terminal (xi) SEQUENCE DESCRIPTION: SEQ ID NO: 20:

Pro Arg Asn Pro His
1                5

(2) INFORMATION FOR SEQ ID NO: 21:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (iii) HYPOTHETICAL: YES (iv) ANTI-SENSE: NO (v) FRAGMENT TYPE: N-terminal (xi) SEQUENCE DESCRIPTION: SEQ ID NO: 21:

Pro Arg Asn Pro His Lys
1                5

(2) INFORMATION FOR SEQ ID NO: 22:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (iii) HYPOTHETICAL: YES (iv) ANTI-SENSE: NO (v) FRAGMENT TYPE: N-terminal (xi) SEQUENCE DESCRIPTION: SEQ ID NO: 22:

Pro Arg Asn Pro His Lys Gly
1                5

(2) INFORMATION FOR SEQ ID NO: 23:

( i ) SEQUENCE CHARACTERISTICS:
    ( A ) LENGTH: 8 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( x i ) SEQUENCE DESCRIPTION: SEQ ID NO: 23:

```
Pro Arg Asn Pro His Lys Gly Pro
1               5
```

( 2 ) INFORMATION FOR SEQ ID NO: 24:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( x i ) SEQUENCE DESCRIPTION: SEQ ID NO: 24:

```
Pro Arg Asn Pro His Lys Gly Pro Ala
1               5
```

( 2 ) INFORMATION FOR SEQ ID NO: 25:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: linear ( x i ) SEQUENCE DESCRIPTION: SEQ ID NO: 25:

```
Pro Arg Asn Pro His Lys Gly Pro Ala Thr
1               5                   10
```

( 2 ) INFORMATION FOR SEQ ID NO: 26:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: linear ( x i ) SEQUENCE DESCRIPTION: SEQ ID NO: 26:

Lys Thr Ala Gly
1

( 2 ) INFORMATION FOR SEQ ID NO: 27:

( i ) SEQUENCE CHARACTERISTICS:
    ( A ) LENGTH: 4 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: linear ( x i ) SEQUENCE DESCRIPTION: SEQ ID NO: 27:

Gly Lys Thr Ala
1

( 2 ) INFORMATION FOR SEQ ID NO: 28:

( i ) SEQUENCE CHARACTERISTICS:
    ( A ) LENGTH: 4 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: linear ( x i ) SEQUENCE DESCRIPTION: SEQ ID NO: 28:

Asn Gly Lys Thr
1

( 2 ) INFORMATION FOR SEQ ID NO: 29:

( i ) SEQUENCE CHARACTERISTICS:
    ( A ) LENGTH: 5 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: linear ( x i ) SEQUENCE DESCRIPTION: SEQ ID NO: 29:

Asn Gly Lys Thr Ala
1       5

( 2 ) INFORMATION FOR SEQ ID NO: 30:

( i ) SEQUENCE CHARACTERISTICS:
    ( A ) LENGTH: 4 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: linear ( x i ) SEQUENCE DESCRIPTION: SEQ ID NO: 30:

Cys Asn Gly Lys
1

( 2 ) INFORMATION FOR SEQ ID NO: 31:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: linear ( x i ) SEQUENCE DESCRIPTION: SEQ ID NO: 31:

Cys Asn Gly Lys Thr
1                 5

( 2 ) INFORMATION FOR SEQ ID NO: 32:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: linear ( x i ) SEQUENCE DESCRIPTION: SEQ ID NO: 32:

Cys Asn Gly Lys Thr Ala
1                 5

( 2 ) INFORMATION FOR SEQ ID NO: 33:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: linear ( x i ) SEQUENCE DESCRIPTION: SEQ ID NO: 33:

Tyr Cys Asn Gly
1

( 2 ) INFORMATION FOR SEQ ID NO: 34:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: linear ( x i ) SEQUENCE DESCRIPTION: SEQ ID NO: 34:

Tyr Cys Asn Gly Lys
1               5

( 2 ) INFORMATION FOR SEQ ID NO: 35:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: linear ( x i ) SEQUENCE DESCRIPTION: SEQ ID NO: 35:

Tyr Cys Asn Gly Lys Thr
1               5

( 2 ) INFORMATION FOR SEQ ID NO: 36:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: linear ( x i ) SEQUENCE DESCRIPTION: SEQ ID NO: 36:

Tyr Cys Asn Gly Lys Thr Ala
1               5

( 2 ) INFORMATION FOR SEQ ID NO: 37:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: YES ( i v ) ANTI-SENSE: NO (v) FRAGMENT TYPE: linear (xi) SEQUENCE DESCRIPTION: SEQ ID NO: 37:

Asp Tyr Cys Asn
            1

(2) INFORMATION FOR SEQ ID NO: 38:

(i) SEQUENCE CHARACTERISTICS:
                        (A) LENGTH: 5 amino acids
                        (B) TYPE: amino acid
                        (C) STRANDEDNESS: single
                        (D) TOPOLOGY: linear (ii) MOLECULE TYPE: peptide (iii) HYPOTHETICAL: YES (iv) ANTI-SENSE: NO (v) FRAGMENT TYPE: linear (xi) SEQUENCE DESCRIPTION: SEQ ID NO: 38:

Asp Tyr Cys Asn Gly
            1               5

(2) INFORMATION FOR SEQ ID NO: 39:

(i) SEQUENCE CHARACTERISTICS:
                        (A) LENGTH: 6 amino acids
                        (B) TYPE: amino acid
                        (C) STRANDEDNESS: single
                        (D) TOPOLOGY: linear (ii) MOLECULE TYPE: peptide (iii) HYPOTHETICAL: YES (iv) ANTI-SENSE: NO (v) FRAGMENT TYPE: linear (xi) SEQUENCE DESCRIPTION: SEQ ID NO: 39:

Asp Tyr Cys Asn Gly Lys
            1               5

(2) INFORMATION FOR SEQ ID NO: 40:

(i) SEQUENCE CHARACTERISTICS:
                        (A) LENGTH: 7 amino acids
                        (B) TYPE: amino acid
                        (C) STRANDEDNESS: single
                        (D) TOPOLOGY: linear (ii) MOLECULE TYPE: peptide (iii) HYPOTHETICAL: YES (iv) ANTI-SENSE: NO (v) FRAGMENT TYPE: linear (xi) SEQUENCE DESCRIPTION: SEQ ID NO: 40:

Asp Tyr Cys Asn Gly Lys Thr
            1               5

(2) INFORMATION FOR SEQ ID NO: 41:

(i) SEQUENCE CHARACTERISTICS:
                        (A) LENGTH: 8 amino acids
                        (B) TYPE: amino acid -continued (C) STRANDEDNESS: single
                (D) TOPOLOGY: linear (ii) MOLECULE TYPE: peptide (iii) HYPOTHETICAL: YES (iv) ANTI-SENSE: NO (v) FRAGMENT TYPE: linear (xi) SEQUENCE DESCRIPTION: SEQ ID NO: 41:

Asp Tyr Cys Asn Gly Lys Thr Ala
        1               5

(2) INFORMATION FOR SEQ ID NO: 42:

(i) SEQUENCE CHARACTERISTICS:
                (A) LENGTH: 4 amino acids
                (B) TYPE: amino acid
                (C) STRANDEDNESS: single
                (D) TOPOLOGY: linear (ii) MOLECULE TYPE: peptide (iii) HYPOTHETICAL: YES (iv) ANTI-SENSE: NO (v) FRAGMENT TYPE: linear (xi) SEQUENCE DESCRIPTION: SEQ ID NO: 42:

Asp Asp Tyr Cys
        1

(2) INFORMATION FOR SEQ ID NO: 43:

(i) SEQUENCE CHARACTERISTICS:
                (A) LENGTH: 5 amino acids
                (B) TYPE: amino acid
                (C) STRANDEDNESS: single
                (D) TOPOLOGY: linear (ii) MOLECULE TYPE: peptide (iii) HYPOTHETICAL: YES (iv) ANTI-SENSE: NO (v) FRAGMENT TYPE: linear (xi) SEQUENCE DESCRIPTION: SEQ ID NO: 43:

Asp Asp Tyr Cys Asn
        1               5

(2) INFORMATION FOR SEQ ID NO: 44:

(i) SEQUENCE CHARACTERISTICS:
                (A) LENGTH: 6 amino acids
                (B) TYPE: amino acid
                (C) STRANDEDNESS: single
                (D) TOPOLOGY: linear (ii) MOLECULE TYPE: peptide (iii) HYPOTHETICAL: YES (iv) ANTI-SENSE: NO (v) FRAGMENT TYPE: linear (xi) SEQUENCE DESCRIPTION: SEQ ID NO: 44:

Asp Asp Tyr Cys Asn Gly ( 2 ) INFORMATION FOR SEQ ID NO: 45:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: linear ( x i ) SEQUENCE DESCRIPTION: SEQ ID NO: 45:

Asp Asp Tyr Cys Asn Gly Lys
    1                5

( 2 ) INFORMATION FOR SEQ ID NO: 46:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: linear ( x i ) SEQUENCE DESCRIPTION: SEQ ID NO: 46:

Asp Asp Tyr Cys Asn Gly Lys Thr
    1                5

( 2 ) INFORMATION FOR SEQ ID NO: 47:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: linear ( x i ) SEQUENCE DESCRIPTION: SEQ ID NO: 47:

Asp Asp Tyr Cys Asn Gly Lys Thr Ala
    1                5

( 2 ) INFORMATION FOR SEQ ID NO: 48:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: linear ( x i ) SEQUENCE DESCRIPTION: SEQ ID NO: 48:

Met Asp Asp Tyr
1

( 2 ) INFORMATION FOR SEQ ID NO: 49:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: linear ( x i ) SEQUENCE DESCRIPTION: SEQ ID NO: 49:

Met Asp Asp Tyr Cys
1               5

( 2 ) INFORMATION FOR SEQ ID NO: 50:

( i ) SEQUENCE CHARACTERISTICS:
( A ) LENGTH: 6 amino acids
( B ) TYPE: amino acid
( C ) STRANDEDNESS: single
( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: linear ( x i ) SEQUENCE DESCRIPTION: SEQ ID NO: 50:

Met Asp Asp Tyr Cys Asn
1               5

( 2 ) INFORMATION FOR SEQ ID NO: 51:

( i ) SEQUENCE CHARACTERISTICS:
( A ) LENGTH: 7 amino acids
( B ) TYPE: amino acid
( C ) STRANDEDNESS: single
( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: linear ( x i ) SEQUENCE DESCRIPTION: SEQ ID NO: 51:

Met Asp Asp Tyr Cys Asn Gly
1               5

( 2 ) INFORMATION FOR SEQ ID NO: 52:

( i ) SEQUENCE CHARACTERISTICS:

(A) LENGTH: 8 amino acids
                (B) TYPE: amino acid
                (C) STRANDEDNESS: single
                (D) TOPOLOGY: linear (ii) MOLECULE TYPE: peptide (iii) HYPOTHETICAL: YES (iv) ANTI-SENSE: NO (v) FRAGMENT TYPE: linear (xi) SEQUENCE DESCRIPTION: SEQ ID NO: 52:

Met Asp Asp Tyr Cys Asn Gly Lys
        1                   5

(2) INFORMATION FOR SEQ ID NO: 53:

(i) SEQUENCE CHARACTERISTICS:
                (A) LENGTH: 9 amino acids
                (B) TYPE: amino acid
                (C) STRANDEDNESS: single
                (D) TOPOLOGY: linear (ii) MOLECULE TYPE: peptide (iii) HYPOTHETICAL: YES (iv) ANTI-SENSE: NO (v) FRAGMENT TYPE: linear (xi) SEQUENCE DESCRIPTION: SEQ ID NO: 53:

Met Asp Asp Tyr Cys Asn Gly Lys Thr
        1                   5

(2) INFORMATION FOR SEQ ID NO: 54:

(i) SEQUENCE CHARACTERISTICS:
                (A) LENGTH: 10 amino acids
                (B) TYPE: amino acid
                (C) STRANDEDNESS: single
                (D) TOPOLOGY: linear (ii) MOLECULE TYPE: peptide (iii) HYPOTHETICAL: YES (iv) ANTI-SENSE: NO (v) FRAGMENT TYPE: linear (xi) SEQUENCE DESCRIPTION: SEQ ID NO: 54:

Met Asp Asp Tyr Cys Asn Gly Lys Thr Ala
        1                   5                   10

(2) INFORMATION FOR SEQ ID NO: 55:

(i) SEQUENCE CHARACTERISTICS:
                (A) LENGTH: 4 amino acids
                (B) TYPE: amino acid
                (C) STRANDEDNESS: single
                (D) TOPOLOGY: linear (ii) MOLECULE TYPE: peptide (iii) HYPOTHETICAL: YES (iv) ANTI-SENSE: NO (v) FRAGMENT TYPE: linear (xi) SEQUENCE DESCRIPTION: SEQ ID NO: 55:

Asp Met Asp Asp
1

( 2 ) INFORMATION FOR SEQ ID NO: 56:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: linear ( x i ) SEQUENCE DESCRIPTION: SEQ ID NO: 56:

Asp Met Asp Asp Tyr
1                 5

( 2 ) INFORMATION FOR SEQ ID NO: 57:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: linear ( x i ) SEQUENCE DESCRIPTION: SEQ ID NO: 57:

Asp Met Asp Asp Tyr Cys
1                 5

( 2 ) INFORMATION FOR SEQ ID NO: 58:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: linear ( x i ) SEQUENCE DESCRIPTION: SEQ ID NO: 58:

Asp Met Asp Asp Tyr Cys Asn
1                 5

( 2 ) INFORMATION FOR SEQ ID NO: 59:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide -continued ( i i i ) HYPOTHETICAL: YES ( i v ) ANTI-SENSE: NO ( v ) FRAGMENT TYPE: linear ( x i ) SEQUENCE DESCRIPTION: SEQ ID NO: 59:

```
Asp Met Asp Asp Tyr Cys Asn Gly
1               5
```

( 2 ) INFORMATION FOR SEQ ID NO: 60:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: linear ( x i ) SEQUENCE DESCRIPTION: SEQ ID NO: 60:

```
Asp Met Asp Asp Tyr Cys Asn Gly Lys
1               5
```

( 2 ) INFORMATION FOR SEQ ID NO: 61:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: linear ( x i ) SEQUENCE DESCRIPTION: SEQ ID NO: 61:

```
Asp Met Asp Asp Tyr Cys Asn Gly Lys Thr
1               5                   10
```

( 2 ) INFORMATION FOR SEQ ID NO: 62:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: linear ( x i ) SEQUENCE DESCRIPTION: SEQ ID NO: 62:

```
Asp Met Asp Asp Tyr Cys Asn Gly Lys Thr Ala
1               5                   10
```

( 2 ) INFORMATION FOR SEQ ID NO: 63:

(i) SEQUENCE CHARACTERISTICS:
  (A) LENGTH: 4 amino acids
  (B) TYPE: amino acid
  (C) STRANDEDNESS: single
  (D) TOPOLOGY: linear (ii) MOLECULE TYPE: peptide (iii) HYPOTHETICAL: YES (iv) ANTI-SENSE: NO (v) FRAGMENT TYPE: linear (xi) SEQUENCE DESCRIPTION: SEQ ID NO: 63:

Arg Asn Pro His
1

(2) INFORMATION FOR SEQ ID NO: 64:

(i) SEQUENCE CHARACTERISTICS:
  (A) LENGTH: 5 amino acids
  (B) TYPE: amino acid
  (C) STRANDEDNESS: single
  (D) TOPOLOGY: linear (ii) MOLECULE TYPE: peptide (iii) HYPOTHETICAL: YES (iv) ANTI-SENSE: NO (v) FRAGMENT TYPE: linear (xi) SEQUENCE DESCRIPTION: SEQ ID NO: 64:

Arg Asn Pro His Lys
1               5

(2) INFORMATION FOR SEQ ID NO: 65:

(i) SEQUENCE CHARACTERISTICS:
  (A) LENGTH: 4 amino acids
  (B) TYPE: amino acid
  (C) STRANDEDNESS: single
  (D) TOPOLOGY: linear (ii) MOLECULE TYPE: peptide (iii) HYPOTHETICAL: YES (iv) ANTI-SENSE: NO (v) FRAGMENT TYPE: linear (xi) SEQUENCE DESCRIPTION: SEQ ID NO: 65:

Asn Pro His Lys
1

(2) INFORMATION FOR SEQ ID NO: 66:

(i) SEQUENCE CHARACTERISTICS:
  (A) LENGTH: 6 amino acids
  (B) TYPE: amino acid
  (C) STRANDEDNESS: single
  (D) TOPOLOGY: linear (ii) MOLECULE TYPE: peptide (iii) HYPOTHETICAL: YES (iv) ANTI-SENSE: NO (v) FRAGMENT TYPE: linear ( x i ) SEQUENCE DESCRIPTION: SEQ ID NO: 66:

Arg Asn Pro His Lys Gly
1               5

( 2 ) INFORMATION FOR SEQ ID NO: 67:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: linear ( x i ) SEQUENCE DESCRIPTION: SEQ ID NO: 67:

Asn Pro His Lys Gly
1           5

( 2 ) INFORMATION FOR SEQ ID NO: 68:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: linear ( x i ) SEQUENCE DESCRIPTION: SEQ ID NO: 68:

Pro His Lys Gly
1

( 2 ) INFORMATION FOR SEQ ID NO: 69:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: linear ( x i ) SEQUENCE DESCRIPTION: SEQ ID NO: 69:

Arg Asn Pro His Lys Gly Pro
1               5

( 2 ) INFORMATION FOR SEQ ID NO: 70:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: linear ( x i ) SEQUENCE DESCRIPTION: SEQ ID NO: 70:

Asn Pro His Lys Gly Pro
1               5

( 2 ) INFORMATION FOR SEQ ID NO: 71:

( i ) SEQUENCE CHARACTERISTICS:
      ( A ) LENGTH: 5 amino acids
      ( B ) TYPE: amino acid
      ( C ) STRANDEDNESS: single
      ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: linear ( x i ) SEQUENCE DESCRIPTION: SEQ ID NO: 71:

Pro His Lys Gly Pro
1               5

( 2 ) INFORMATION FOR SEQ ID NO: 72:

( i ) SEQUENCE CHARACTERISTICS:
      ( A ) LENGTH: 4 amino acids
      ( B ) TYPE: amino acid
      ( C ) STRANDEDNESS: single
      ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: linear ( x i ) SEQUENCE DESCRIPTION: SEQ ID NO: 72:

His Lys Gly Pro
1

( 2 ) INFORMATION FOR SEQ ID NO: 73:

( i ) SEQUENCE CHARACTERISTICS:
      ( A ) LENGTH: 8 amino acids
      ( B ) TYPE: amino acid
      ( C ) STRANDEDNESS: single
      ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: linear ( x i ) SEQUENCE DESCRIPTION: SEQ ID NO: 73:

Arg Asn Pro His Lys Gly Pro Ala
1               5

( 2 ) INFORMATION FOR SEQ ID NO: 74:

( i ) SEQUENCE CHARACTERISTICS:
    ( A ) LENGTH: 7 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: linear ( x i ) SEQUENCE DESCRIPTION: SEQ ID NO: 74:

Asn Pro His Lys Gly Pro Ala
  1       5

( 2 ) INFORMATION FOR SEQ ID NO: 75:

( i ) SEQUENCE CHARACTERISTICS:
    ( A ) LENGTH: 6 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: linear ( x i ) SEQUENCE DESCRIPTION: SEQ ID NO: 75:

Pro His Lys Gly Pro Ala
  1     5

( 2 ) INFORMATION FOR SEQ ID NO: 76:

( i ) SEQUENCE CHARACTERISTICS:
    ( A ) LENGTH: 5 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: linear ( x i ) SEQUENCE DESCRIPTION: SEQ ID NO: 76:

His Lys Gly Pro Ala
  1    5

( 2 ) INFORMATION FOR SEQ ID NO: 77:

( i ) SEQUENCE CHARACTERISTICS:
    ( A ) LENGTH: 4 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: linear ( x i ) SEQUENCE DESCRIPTION: SEQ ID NO: 77:

Lys Gly Pro Ala
1

( 2 ) INFORMATION FOR SEQ ID NO: 78:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: linear ( x i ) SEQUENCE DESCRIPTION: SEQ ID NO: 78:

Arg Asn Pro His Lys Gly Pro Ala Thr
1                   5

( 2 ) INFORMATION FOR SEQ ID NO: 79:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: linear ( x i ) SEQUENCE DESCRIPTION: SEQ ID NO: 79:

Asn Pro His Lys Gly Pro Ala Thr
1               5

( 2 ) INFORMATION FOR SEQ ID NO: 80:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: linear ( x i ) SEQUENCE DESCRIPTION: SEQ ID NO: 80:

Pro His Lys Gly Pro Ala Thr
1           5

( 2 ) INFORMATION FOR SEQ ID NO: 81:

( i ) SEQUENCE CHARACTERISTICS:
        ( A ) LENGTH: 6 amino acids
        ( B ) TYPE: amino acid (C) STRANDEDNESS: single
(D) TOPOLOGY: linear (ii) MOLECULE TYPE: peptide (iii) HYPOTHETICAL: YES (iv) ANTI-SENSE: NO (v) FRAGMENT TYPE: linear (xi) SEQUENCE DESCRIPTION: SEQ ID NO: 81:

His Lys Gly Pro Ala Thr
1               5

(2) INFORMATION FOR SEQ ID NO: 82:

(i) SEQUENCE CHARACTERISTICS:
(A) LENGTH: 5 amino acids
(B) TYPE: amino acid
(C) STRANDEDNESS: single
(D) TOPOLOGY: linear (ii) MOLECULE TYPE: peptide (iii) HYPOTHETICAL: YES (iv) ANTI-SENSE: NO (v) FRAGMENT TYPE: linear (xi) SEQUENCE DESCRIPTION: SEQ ID NO: 82:

Lys Gly Pro Ala Thr
1               5

(2) INFORMATION FOR SEQ ID NO: 83:

(i) SEQUENCE CHARACTERISTICS:
(A) LENGTH: 4 amino acids
(B) TYPE: amino acid
(C) STRANDEDNESS: single
(D) TOPOLOGY: linear (ii) MOLECULE TYPE: peptide (iii) HYPOTHETICAL: YES (iv) ANTI-SENSE: NO (v) FRAGMENT TYPE: linear (xi) SEQUENCE DESCRIPTION: SEQ ID NO: 83:

Gly Pro Ala Thr
1

(2) INFORMATION FOR SEQ ID NO: 84:

(i) SEQUENCE CHARACTERISTICS:
(A) LENGTH: 4 amino acids
(B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (v) FRAGMENT TYPE: N-terminal (ix) FEATURE:
(A) NAME/KEY: Modified-site
(B) LOCATION:1

( D ) OTHER INFORMATION:/product="Lys"
    / note="N-terminal: acetyl"

( x i ) SEQUENCE DESCRIPTION: SEQ ID NO: 84:

Lys Thr Ala Asp
1

( 2 ) INFORMATION FOR SEQ ID NO: 85:

( i ) SEQUENCE CHARACTERISTICS:
    ( A ) LENGTH: 4 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( i x ) FEATURE:
    ( A ) NAME/KEY: Modified-site
    ( B ) LOCATION:1
    ( D ) OTHER INFORMATION:/product="acetyl"
        / note="N-terminal: -acetyl"

( x i ) SEQUENCE DESCRIPTION: SEQ ID NO: 85:

Gln Ser Ala Asp
1

( 2 ) INFORMATION FOR SEQ ID NO: 86:

( i ) SEQUENCE CHARACTERISTICS:
    ( A ) LENGTH: 4 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
    ( A ) NAME/KEY: Modified-site
    ( B ) LOCATION:1
    ( D ) OTHER INFORMATION:/product="Fmoc-Lys(Boc)"

( i x ) FEATURE:
    ( A ) NAME/KEY: Modified-site
    ( B ) LOCATION:2
    ( D ) OTHER INFORMATION:/product="Thr(But)"

( i x ) FEATURE:
    ( A ) NAME/KEY: Modified-site
    ( B ) LOCATION:4
    ( D ) OTHER INFORMATION:/product="Asp(OBut)"

( x i ) SEQUENCE DESCRIPTION: SEQ ID NO: 86:

Lys Thr Gly Asp
1

( 2 ) INFORMATION FOR SEQ ID NO: 87:

( i ) SEQUENCE CHARACTERISTICS:
    ( A ) LENGTH: 4 amino acids
    ( B ) TYPE: amino acid
    ( C ) STRANDEDNESS: single (D) TOPOLOGY: linear (ii) MOLECULE TYPE: peptide (iii) HYPOTHETICAL: YES (iv) ANTI-SENSE: NO (v) FRAGMENT TYPE: N-terminal (ix) FEATURE:
                    (A) NAME/KEY: Modified-site
                    (B) LOCATION: 1
                    (D) OTHER INFORMATION:/product="Lys(BOC)"
                        / note="N-terminal: FMOC"

(ix) FEATURE:
                    (A) NAME/KEY: Modified-site
                    (B) LOCATION: 2
                    (D) OTHER INFORMATION:/product="Thr(But)"

(ix) FEATURE:
                    (A) NAME/KEY: Modified-site
                    (B) LOCATION: 4
                    (D) OTHER INFORMATION:/product="Asn-trityl"
                        / note="N-Trityl"

(xi) SEQUENCE DESCRIPTION: SEQ ID NO: 87:

Lys  Thr  Ala  Asn
    1

(2) INFORMATION FOR SEQ ID NO: 88:

(i) SEQUENCE CHARACTERISTICS:
                    (A) LENGTH: 4 amino acids
                    (B) TYPE: amino acid
                    (C) STRANDEDNESS: single
                    (D) TOPOLOGY: linear (ii) MOLECULE TYPE: peptide (iii) HYPOTHETICAL: YES (iv) ANTI-SENSE: NO (v) FRAGMENT TYPE: N-terminal (ix) FEATURE:
                    (A) NAME/KEY: Modified-site
                    (B) LOCATION: 1
                    (D) OTHER INFORMATION:/product="Lys(BOC)"
                        / note="N-terminal: FMOC"

(ix) FEATURE:
                    (A) NAME/KEY: Modified-site
                    (B) LOCATION: 4
                    (D) OTHER INFORMATION:/product="Asp(OBut)"

(xi) SEQUENCE DESCRIPTION: SEQ ID NO: 88:

Lys  Ala  Ala  Asp
    1

(2) INFORMATION FOR SEQ ID NO: 89:

(i) SEQUENCE CHARACTERISTICS:
                    (A) LENGTH: 4 amino acids
                    (B) TYPE: amino acid
                    (C) STRANDEDNESS: single
                    (D) TOPOLOGY: linear (ii) MOLECULE TYPE: peptide (iii) HYPOTHETICAL: YES (iv) ANTI-SENSE: NO -continued

```
        ( v ) FRAGMENT TYPE: N-terminal ( i x ) FEATURE:
                ( A ) NAME/KEY: Modified-site
                ( B ) LOCATION: 1
                ( D ) OTHER INFORMATION:/product="Arg(Mtr)"
                         / note="N-terminal: FMOC"

( i x ) FEATURE:
                ( A ) NAME/KEY: Modified-site
                ( B ) LOCATION: 2
                ( D ) OTHER INFORMATION:/product="Thr(But)"

( i x ) FEATURE:
                ( A ) NAME/KEY: Modified-site
                ( B ) LOCATION: 4
                ( D ) OTHER INFORMATION:/product="Asp(OBut)"

( x i ) SEQUENCE DESCRIPTION: SEQ ID NO: 89:

Arg  Thr  Ala  Asp
      1
```

( 2 ) INFORMATION FOR SEQ ID NO: 90:

```
        ( i ) SEQUENCE CHARACTERISTICS:
                ( A ) LENGTH: 4 amino acids
                ( B ) TYPE: amino acid
                ( C ) STRANDEDNESS: single
                ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
                ( A ) NAME/KEY: Modified-site
                ( B ) LOCATION: 1
                ( D ) OTHER INFORMATION:/product="Lys(BOC)"
                         / note="N-terminal: FMOC"

( i x ) FEATURE:
                ( A ) NAME/KEY: Modified-site
                ( B ) LOCATION: 2
                ( D ) OTHER INFORMATION:/product="Thr(But)"

( i x ) FEATURE:
                ( A ) NAME/KEY: Modified-site
                ( B ) LOCATION: 4
                ( D ) OTHER INFORMATION:/product="Asp(OBut)"

( x i ) SEQUENCE DESCRIPTION: SEQ ID NO: 90:

Lys  Thr  Ala  Asp
      1
```

( 2 ) INFORMATION FOR SEQ ID NO: 91:

```
        ( i ) SEQUENCE CHARACTERISTICS:
                ( A ) LENGTH: 4 amino acids
                ( B ) TYPE: amino acid
                ( C ) STRANDEDNESS: single
                ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
                ( A ) NAME/KEY: Modified-site
```

( B ) LOCATION:2
                    ( D ) OTHER INFORMATION:/product="Ser(But)"

( i x ) FEATURE:
                    ( A ) NAME/KEY: Modified-site
                    ( B ) LOCATION:1
                    ( D ) OTHER INFORMATION:/product="Gln-trityl"
                        / note="N-terminal: FMOC; N'-trityl"

( i x ) FEATURE:
                    ( A ) NAME/KEY: Modified-site
                    ( B ) LOCATION:4
                    ( D ) OTHER INFORMATION:/product="Asp(OBut)"

( x i ) SEQUENCE DESCRIPTION: SEQ ID NO: 91:

Gln  Ser  Ala  Asp
            1

( 2 ) INFORMATION FOR SEQ ID NO: 92:

( i ) SEQUENCE CHARACTERISTICS:
                    ( A ) LENGTH: 6 amino acids
                    ( B ) TYPE: amino acid
                    ( C ) STRANDEDNESS: single
                    ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
                    ( A ) NAME/KEY: Modified-site
                    ( B ) LOCATION:5
                    ( D ) OTHER INFORMATION:/product="Cys-Trityl"

( i x ) FEATURE:
                    ( A ) NAME/KEY: Modified-site
                    ( B ) LOCATION:5
                    ( D ) OTHER INFORMATION:/product="Cys-trityl"
                        / note="S-Trityl"

( x i ) SEQUENCE DESCRIPTION: SEQ ID NO: 92:

Lys  Thr  Ala  Asn  Cys  Pro
            1                   5

( 2 ) INFORMATION FOR SEQ ID NO: 93:

( i ) SEQUENCE CHARACTERISTICS:
                    ( A ) LENGTH: 6 amino acids
                    ( B ) TYPE: amino acid
                    ( C ) STRANDEDNESS: single
                    ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( x i ) SEQUENCE DESCRIPTION: SEQ ID NO: 93:

Lys  Thr  Ala  Asp  Cys  Pro
            1                   5

( 2 ) INFORMATION FOR SEQ ID NO: 94:

( i ) SEQUENCE CHARACTERISTICS:
                    ( A ) LENGTH: 6 amino acids
                    ( B ) TYPE: amino acid (C) STRANDEDNESS: single
            (D) TOPOLOGY: linear (ii) MOLECULE TYPE: peptide (iii) HYPOTHETICAL: YES (iv) ANTI-SENSE: NO (v) FRAGMENT TYPE: N-terminal (ix) FEATURE:
            (A) NAME/KEY: Modified-site
            (B) LOCATION:5
            (D) OTHER INFORMATION:/product="Cys-trityl"
                    / note="S-trityl"

(xi) SEQUENCE DESCRIPTION: SEQ ID NO: 94:

Lys  Ala  Ala  Asp  Cys  Pro
    1                    5

(2) INFORMATION FOR SEQ ID NO: 95:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: peptide (iii) HYPOTHETICAL: YES (iv) ANTI-SENSE: NO (v) FRAGMENT TYPE: N-terminal (ix) FEATURE:
            (A) NAME/KEY: Modified-site
            (B) LOCATION:5
            (D) OTHER INFORMATION:/product="Cys(Trt)"

(xi) SEQUENCE DESCRIPTION: SEQ ID NO: 95:

Arg  Thr  Ala  Asp  Cys  Pro
    1                    5

(2) INFORMATION FOR SEQ ID NO: 96:

(i) SEQUENCE CHARACTERISTICS:
            (A) LENGTH: 5 amino acids
            (B) TYPE: amino acid
            (C) STRANDEDNESS: single
            (D) TOPOLOGY: linear (ii) MOLECULE TYPE: peptide (iii) HYPOTHETICAL: YES (iv) ANTI-SENSE: NO (v) FRAGMENT TYPE: N-terminal (ix) FEATURE:
            (A) NAME/KEY: Modified-site
            (B) LOCATION:4
            (D) OTHER INFORMATION:/product="Cys-trityl"
                    / note="N-trityl"

(xi) SEQUENCE DESCRIPTION: SEQ ID NO: 96:

Ser  Ala  Asp  Cys  Pro
    1               5

(2) INFORMATION FOR SEQ ID NO: 97:

```
        ( i ) SEQUENCE CHARACTERISTICS:
                ( A ) LENGTH: 6 amino acids
                ( B ) TYPE: amino acid
                ( C ) STRANDEDNESS: single
                ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
                ( A ) NAME/KEY: Modified-site
                ( B ) LOCATION:5
                ( D ) OTHER INFORMATION:/product="Cys-Trityl"

( i x ) FEATURE:
                ( A ) NAME/KEY: Modified-site
                ( B ) LOCATION:5
                ( D ) OTHER INFORMATION:/product="Cys-trityl"
                        / note="S-trityl"

( x i ) SEQUENCE DESCRIPTION: SEQ ID NO: 97:

Gln  Ser  Ala  Asp  Cys  Pro
       1                   5

( 2 ) INFORMATION FOR SEQ ID NO: 98:

( i ) SEQUENCE CHARACTERISTICS:
                ( A ) LENGTH: 6 amino acids
                ( B ) TYPE: amino acid
                ( C ) STRANDEDNESS: single
                ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
                ( A ) NAME/KEY: Modified-site
                ( B ) LOCATION:1
                ( D ) OTHER INFORMATION:/product="X is Glp"

( i x ) FEATURE:
                ( A ) NAME/KEY: Modified-site
                ( B ) LOCATION:5
                ( D ) OTHER INFORMATION:/product="Cys(Trt)"

( x i ) SEQUENCE DESCRIPTION: SEQ ID NO: 98:

Xaa  Ser  Ala  Asp  Cys  Pro
       1                   5

( 2 ) INFORMATION FOR SEQ ID NO: 99:

( i ) SEQUENCE CHARACTERISTICS:
                ( A ) LENGTH: 6 amino acids
                ( B ) TYPE: amino acid
                ( C ) STRANDEDNESS: single
                ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
```

(A) NAME/KEY: Modified-site
        (B) LOCATION:5
        (D) OTHER INFORMATION:/product="Cys-trityl"
              / note="S-trityl"

(xi) SEQUENCE DESCRIPTION: SEQ ID NO: 99:

Ile Ser Ala Gly Cys Pro
1               5

(2) INFORMATION FOR SEQ ID NO: 100:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (iii) HYPOTHETICAL: YES (iv) ANTI-SENSE: NO (v) FRAGMENT TYPE: N-terminal (ix) FEATURE:
        (A) NAME/KEY: Modified-site
        (B) LOCATION:5
        (D) OTHER INFORMATION:/product="Cys-trityl"
              / note="S-trityl"

(xi) SEQUENCE DESCRIPTION: SEQ ID NO: 100:

Arg Ser Ala Gly Cys Pro
1               5

(2) INFORMATION FOR SEQ ID NO: 101:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (iii) HYPOTHETICAL: YES (iv) ANTI-SENSE: NO (v) FRAGMENT TYPE: N-terminal (ix) FEATURE:
        (A) NAME/KEY: Modified-site
        (B) LOCATION:5
        (D) OTHER INFORMATION:/product="Cys-trityl"
              / note="S-trityl"

(xi) SEQUENCE DESCRIPTION: SEQ ID NO: 101:

Lys Gly Gly Asp Cys Pro
1               5

(2) INFORMATION FOR SEQ ID NO: 102:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (iii) HYPOTHETICAL: YES (iv) ANTI-SENSE: NO (v) FRAGMENT TYPE: N-terminal (ix) FEATURE:
    (A) NAME/KEY: Modified-site
    (B) LOCATION:5
    (D) OTHER INFORMATION:/product="Cys-trityl"
        / note="S-trityl"

(ix) FEATURE:
    (A) NAME/KEY: Modified-site
    (B) LOCATION:1
    (D) OTHER INFORMATION:/product="Lys(BOC)"
        / note="N-terminal: FMOC"

(ix) FEATURE:
    (A) NAME/KEY: Modified-site
    (B) LOCATION:2
    (D) OTHER INFORMATION:/product="Thr(But)"

(ix) FEATURE:
    (A) NAME/KEY: Modified-site
    (B) LOCATION:4
    (D) OTHER INFORMATION:/product="Asp(OBut)"

(xi) SEQUENCE DESCRIPTION: SEQ ID NO: 102:

Lys  Thr  Ala  Asp  Cys
1                    5

(2) INFORMATION FOR SEQ ID NO: 103:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (iii) HYPOTHETICAL: YES (iv) ANTI-SENSE: NO (v) FRAGMENT TYPE: N-terminal (ix) FEATURE:
        (A) NAME/KEY: Modified-site
        (B) LOCATION:5
        (D) OTHER INFORMATION:/product="Cys-trityl"
            / note="S-trityl"

(xi) SEQUENCE DESCRIPTION: SEQ ID NO: 103:

Lys  Thr  Ala  Asp  Cys
1                    5

(2) INFORMATION FOR SEQ ID NO: 104:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (iii) HYPOTHETICAL: YES (iv) ANTI-SENSE: NO (v) FRAGMENT TYPE: N-terminal (ix) FEATURE:
        (A) NAME/KEY: Modified-site
        (B) LOCATION:1
        (D) OTHER INFORMATION:/product="Asn(Trt)"

( i x ) FEATURE:
    ( A ) NAME/KEY: Modified-site
    ( B ) LOCATION:3
    ( D ) OTHER INFORMATION:/product="His(Trt)"

( i x ) FEATURE:
    ( A ) NAME/KEY: Modified-site
    ( B ) LOCATION:4
    ( D ) OTHER INFORMATION:/product="Lys(Boc)"

( i x ) FEATURE:
    ( A ) NAME/KEY: Modified-site
    ( B ) LOCATION:8
    ( D ) OTHER INFORMATION:/product="Thr(But)-OMe"

( x i ) SEQUENCE DESCRIPTION: SEQ ID NO: 104:

Asn  Pro  His  Lys  Gly  Pro  Ala  Thr
1                           5

( 2 ) INFORMATION FOR SEQ ID NO: 105:

( i ) SEQUENCE CHARACTERISTICS:
        ( A ) LENGTH: 5 amino acids
        ( B ) TYPE: amino acid
        ( C ) STRANDEDNESS:
        ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
        ( A ) NAME/KEY: Modified-site
        ( B ) LOCATION:1
        ( D ) OTHER INFORMATION:/product="Boc-Gly"

( i x ) FEATURE:
        ( A ) NAME/KEY: Modified-site
        ( B ) LOCATION:2
        ( D ) OTHER INFORMATION:/product="Lys(Boc)"

( i x ) FEATURE:
        ( A ) NAME/KEY: Modified-site
        ( B ) LOCATION:3
        ( D ) OTHER INFORMATION:/product="Thr(But)"

( i x ) FEATURE:
        ( A ) NAME/KEY: Modified-site
        ( B ) LOCATION:4
        ( D ) OTHER INFORMATION:/product="Cys(Trt)"

( i x ) FEATURE:
        ( A ) NAME/KEY: Modified-site
        ( B ) LOCATION:5
        ( D ) OTHER INFORMATION:/product="Asp(OBut)"

( x i ) SEQUENCE DESCRIPTION: SEQ ID NO: 105:

Gly  Lys  Thr  Cys  Asp
1                       5

( 2 ) INFORMATION FOR SEQ ID NO: 106:

( i ) SEQUENCE CHARACTERISTICS:
        ( A ) LENGTH: 11 amino acids
        ( B ) TYPE: amino acid
        ( C ) STRANDEDNESS:
        ( D ) TOPOLOGY: linear ( i i ) MOLECULE TYPE: peptide ( i i i ) HYPOTHETICAL: YES (iv) ANTI-SENSE: NO (v) FRAGMENT TYPE: N-terminal (ix) FEATURE:
    (A) NAME/KEY: Modified-site
    (B) LOCATION:1
    (D) OTHER INFORMATION:/product="Cys(Trt)"

(ix) FEATURE:
    (A) NAME/KEY: Modified-site
    (B) LOCATION:3
    (D) OTHER INFORMATION:/product="Arg(Mtr)"

(ix) FEATURE:
    (A) NAME/KEY: Modified-site
    (B) LOCATION:4
    (D) OTHER INFORMATION:/product="Asn(Trt)"

(ix) FEATURE:
    (A) NAME/KEY: Modified-site
    (B) LOCATION:6
    (D) OTHER INFORMATION:/product="His(Trt)"

(ix) FEATURE:
    (A) NAME/KEY: Modified-site
    (B) LOCATION:7
    (D) OTHER INFORMATION:/product="Lys(Boc)"

(ix) FEATURE:
    (A) NAME/KEY: Modified-site
    (B) LOCATION:11
    (D) OTHER INFORMATION:/product="Thr(But)-OMe"

(xi) SEQUENCE DESCRIPTION: SEQ ID NO: 106:

Cys Pro Arg Asn Pro His Lys Gly Pro Ala Thr
1              5                          10

(2) INFORMATION FOR SEQ ID NO: 107:

(i) SEQUENCE CHARACTERISTICS:
        (A) LENGTH: 16 amino acids
        (B) TYPE: amino acid
        (C) STRANDEDNESS:
        (D) TOPOLOGY: linear (ii) MOLECULE TYPE: peptide (iii) HYPOTHETICAL: YES (iv) ANTI-SENSE: NO (v) FRAGMENT TYPE: N-terminal (ix) FEATURE:
        (A) NAME/KEY: Modified-site
        (B) LOCATION:1
        (D) OTHER INFORMATION:/product="Boc-Gly"

(ix) FEATURE:
        (A) NAME/KEY: Modified-site
        (B) LOCATION:2
        (D) OTHER INFORMATION:/product="Lys(Boc)"

(ix) FEATURE:
        (A) NAME/KEY: Modified-site
        (B) LOCATION:3
        (D) OTHER INFORMATION:/product="Thr(But)"

(ix) FEATURE:
        (A) NAME/KEY: Modified-site
        (B) LOCATION:4
        (D) OTHER INFORMATION:/product="Cys(Trt)"

(ix) FEATURE:
        (A) NAME/KEY: Modified-site
        (B) LOCATION:5
        (D) OTHER INFORMATION:/product="Asp(OBut)"

( i x ) FEATURE:
    ( A ) NAME/KEY: Modified-site
    ( B ) LOCATION:6
    ( D ) OTHER INFORMATION:/product="Cys(Trt)"

( i x ) FEATURE:
    ( A ) NAME/KEY: Modified-site
    ( B ) LOCATION:8
    ( D ) OTHER INFORMATION:/product="Arg(Mtr)"

( i x ) FEATURE:
    ( A ) NAME/KEY: Modified-site
    ( B ) LOCATION:9
    ( D ) OTHER INFORMATION:/product="Asn(Trt)"

( i x ) FEATURE:
    ( A ) NAME/KEY: Modified-site
    ( B ) LOCATION:11
    ( D ) OTHER INFORMATION:/product="His(Trt)"

( i x ) FEATURE:
    ( A ) NAME/KEY: Modified-site
    ( B ) LOCATION:12
    ( D ) OTHER INFORMATION:/product="Lys(Boc)"

( i x ) FEATURE:
    ( A ) NAME/KEY: Modified-site
    ( B ) LOCATION:16
    ( D ) OTHER INFORMATION:/product="Thr(But)-OMe"

( x i ) SEQUENCE DESCRIPTION: SEQ ID NO: 107:

Gly Lys Thr Cys Asp Cys Pro Arg Asn Pro His Lys Gly Pro Ala Thr
1                    5                         10                      15

( 2 ) INFORMATION FOR SEQ ID NO: 108:

( i ) SEQUENCE CHARACTERISTICS:
        ( A ) LENGTH: 5 amino acids
        ( B ) TYPE: amino acid
        ( C ) STRANDEDNESS:
        ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
        ( A ) NAME/KEY: Modified-site
        ( B ) LOCATION:1
        ( D ) OTHER INFORMATION:/product="Boc-Lys(Boc)"

( i x ) FEATURE:
        ( A ) NAME/KEY: Modified-site
        ( B ) LOCATION:2
        ( D ) OTHER INFORMATION:/product="Thr(But)"

( i x ) FEATURE:
        ( A ) NAME/KEY: Modified-site
        ( B ) LOCATION:4
        ( D ) OTHER INFORMATION:/product="Asp(OBut)"

( i x ) FEATURE:
        ( A ) NAME/KEY: Modified-site
        ( B ) LOCATION:5
        ( D ) OTHER INFORMATION:/product="Cys(Trt)"

( x i ) SEQUENCE DESCRIPTION: SEQ ID NO: 108:

Lys Thr Ala Asp Cys
1                    5

( 2 ) INFORMATION FOR SEQ ID NO: 109:

( i ) SEQUENCE CHARACTERISTICS:
    ( A ) LENGTH: 7 amino acids
    ( B ) TYPE: amino acid
    ( C ) STRANDEDNESS:
    ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
    ( A ) NAME/KEY: Modified-site
    ( B ) LOCATION:2
    ( D ) OTHER INFORMATION:/product="Arg(Mtr)"

( i x ) FEATURE:
    ( A ) NAME/KEY: Modified-site
    ( B ) LOCATION:3
    ( D ) OTHER INFORMATION:/product="Asn(Trt)"

( i x ) FEATURE:
    ( A ) NAME/KEY: Modified-site
    ( B ) LOCATION:5
    ( D ) OTHER INFORMATION:/product="His(Trt)"

( i x ) FEATURE:
    ( A ) NAME/KEY: Modified-site
    ( B ) LOCATION:6
    ( D ) OTHER INFORMATION:/product="Lys(Boc)"

( i x ) FEATURE:
    ( A ) NAME/KEY: Modified-site
    ( B ) LOCATION:7
    ( D ) OTHER INFORMATION:/product="Gly-OMe"

( x i ) SEQUENCE DESCRIPTION: SEQ ID NO: 109:

Pro Arg Asn Pro His Lys Gly
1               5

( 2 ) INFORMATION FOR SEQ ID NO: 110:

( i ) SEQUENCE CHARACTERISTICS:
        ( A ) LENGTH: 12 amino acids
        ( B ) TYPE: amino acid
        ( C ) STRANDEDNESS:
        ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
        ( A ) NAME/KEY: Modified-site
        ( B ) LOCATION:1
        ( D ) OTHER INFORMATION:/product="Boc-Lys(Boc)"

( i x ) FEATURE:
        ( A ) NAME/KEY: Modified-site
        ( B ) LOCATION:2
        ( D ) OTHER INFORMATION:/product="Thr(But)"

( i x ) FEATURE:
        ( A ) NAME/KEY: Modified-site
        ( B ) LOCATION:4
        ( D ) OTHER INFORMATION:/product="Asp(OBut)"

( i x ) FEATURE:
        ( A ) NAME/KEY: Modified-site
        ( B ) LOCATION:5

( D ) OTHER INFORMATION:/product="Cys(Trt)"

( i x ) FEATURE:
                ( A ) NAME/KEY: Modified-site
                ( B ) LOCATION:7
                ( D ) OTHER INFORMATION:/product="Arg(Mtr)"

( i x ) FEATURE:
                ( A ) NAME/KEY: Modified-site
                ( B ) LOCATION:8
                ( D ) OTHER INFORMATION:/product="Asn(Trt)"

( i x ) FEATURE:
                ( A ) NAME/KEY: Modified-site
                ( B ) LOCATION:10
                ( D ) OTHER INFORMATION:/product="His(Trt)"

( i x ) FEATURE:
                ( A ) NAME/KEY: Modified-site
                ( B ) LOCATION:11
                ( D ) OTHER INFORMATION:/product="Lys(Boc)"

( i x ) FEATURE:
                ( A ) NAME/KEY: Modified-site
                ( B ) LOCATION:12
                ( D ) OTHER INFORMATION:/product="Gly-OMe"

( x i ) SEQUENCE DESCRIPTION: SEQ ID NO: 110:

Lys  Thr  Ala  Asp  Cys  Pro  Arg  Asn  Pro  His  Lys  Gly
 1                    5                         10

( 2 ) INFORMATION FOR SEQ ID NO: 111:

( i ) SEQUENCE CHARACTERISTICS:
                ( A ) LENGTH: 14 amino acids
                ( B ) TYPE: amino acid
                ( C ) STRANDEDNESS:
                ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
                ( A ) NAME/KEY: Modified-site
                ( B ) LOCATION:1
                ( D ) OTHER INFORMATION:/product="Boc-Thr(But)"

( i x ) FEATURE:
                ( A ) NAME/KEY: Modified-site
                ( B ) LOCATION:3
                ( D ) OTHER INFORMATION:/product="Asp(OBut)"

( i x ) FEATURE:
                ( A ) NAME/KEY: Modified-site
                ( B ) LOCATION:6
                ( D ) OTHER INFORMATION:/product="Arg(Mtr)"

( i x ) FEATURE:
                ( A ) NAME/KEY: Modified-site
                ( B ) LOCATION:7
                ( D ) OTHER INFORMATION:/product="Asn(Trt)"

( i x ) FEATURE:
                ( A ) NAME/KEY: Modified-site
                ( B ) LOCATION:9
                ( D ) OTHER INFORMATION:/product="His(Trt)"

( i x ) FEATURE:
                ( A ) NAME/KEY: Modified-site
                ( B ) LOCATION:10
                ( D ) OTHER INFORMATION:/product="Lys(Boc)"

( i x ) FEATURE:

(A) NAME/KEY: Modified-site
(B) LOCATION: 14
(D) OTHER INFORMATION:/product="Thr(But)-OMe"

(xi) SEQUENCE DESCRIPTION: SEQ ID NO: 111:

Thr Ala Asp Cys Pro Arg Asn Pro His Lys Gly Pro Ala Thr
1               5                   10

(2) INFORMATION FOR SEQ ID NO: 112:

(i) SEQUENCE CHARACTERISTICS:
      (A) LENGTH: 14 amino acids
      (B) TYPE: amino acid
      (C) STRANDEDNESS:
      (D) TOPOLOGY: linear (ii) MOLECULE TYPE: peptide (iii) HYPOTHETICAL: YES (iv) ANTI-SENSE: NO (v) FRAGMENT TYPE: N-terminal (ix) FEATURE:
      (A) NAME/KEY: Modified-site
      (B) LOCATION: 1
      (D) OTHER INFORMATION:/product="Boc-Thr(But)"

(ix) FEATURE:
      (A) NAME/KEY: Modified-site
      (B) LOCATION: 3
      (D) OTHER INFORMATION:/product="Asp(OBut)"

(ix) FEATURE:
      (A) NAME/KEY: Modified-site
      (B) LOCATION: 6
      (D) OTHER INFORMATION:/product="Arg(Mtr)"

(ix) FEATURE:
      (A) NAME/KEY: Modified-site
      (B) LOCATION: 7
      (D) OTHER INFORMATION:/product="Asn(Trt)"

(ix) FEATURE:
      (A) NAME/KEY: Modified-site
      (B) LOCATION: 9
      (D) OTHER INFORMATION:/product="His(Trt)"

(ix) FEATURE:
      (A) NAME/KEY: Modified-site
      (B) LOCATION: 10
      (D) OTHER INFORMATION:/product="Lys(Boc)"

(ix) FEATURE:
      (A) NAME/KEY: Modified-site
      (B) LOCATION: 14
      (D) OTHER INFORMATION:/product="Thr(But)"

(xi) SEQUENCE DESCRIPTION: SEQ ID NO: 112:

Thr Ala Asp Cys Pro Arg Asn Pro His Lys Gly Pro Ala Thr
1               5                   10

(2) INFORMATION FOR SEQ ID NO: 113:

(i) SEQUENCE CHARACTERISTICS:
      (A) LENGTH: 14 amino acids
      (B) TYPE: amino acid
      (C) STRANDEDNESS:
      (D) TOPOLOGY: linear (ii) MOLECULE TYPE: peptide (iii) HYPOTHETICAL: YES (iv) ANTI-SENSE: NO (v) FRAGMENT TYPE: N-terminal (xi) SEQUENCE DESCRIPTION: SEQ ID NO: 113:

Thr Ala Asp Cys Pro Arg Asn Pro His Lys Gly Pro Ala Thr
1               5                   10

(2) INFORMATION FOR SEQ ID NO: 114:

(i) SEQUENCE CHARACTERISTICS:
      (A) LENGTH: 14 amino acids
      (B) TYPE: amino acid
      (C) STRANDEDNESS:
      (D) TOPOLOGY: linear (ii) MOLECULE TYPE: peptide (iii) HYPOTHETICAL: YES (iv) ANTI-SENSE: NO (v) FRAGMENT TYPE: N-terminal (xi) SEQUENCE DESCRIPTION: SEQ ID NO: 114:

Gly Lys Thr Cys Pro Arg Asn Pro His Lys Gly Pro Ala Thr
1               5                   10

(2) INFORMATION FOR SEQ ID NO: 115:

(i) SEQUENCE CHARACTERISTICS:
      (A) LENGTH: 12 amino acids
      (B) TYPE: amino acid
      (C) STRANDEDNESS:
      (D) TOPOLOGY: linear (ii) MOLECULE TYPE: peptide (iii) HYPOTHETICAL: YES (iv) ANTI-SENSE: NO (v) FRAGMENT TYPE: N-terminal (xi) SEQUENCE DESCRIPTION: SEQ ID NO: 115:

Lys Thr Ala Asp Cys Pro Arg Asn Pro His Lys Gly
1               5                   10

(2) INFORMATION FOR SEQ ID NO: 116:

(i) SEQUENCE CHARACTERISTICS:
      (A) LENGTH: 7 amino acids
      (B) TYPE: amino acid
      (C) STRANDEDNESS:
      (D) TOPOLOGY: linear (ii) MOLECULE TYPE: peptide (iii) HYPOTHETICAL: YES (iv) ANTI-SENSE: NO (v) FRAGMENT TYPE: N-terminal (ix) FEATURE:
      (A) NAME/KEY: Modified-site
      (B) LOCATION:1
      (D) OTHER INFORMATION:/product="Fmoc-Pro"

(ix) FEATURE:
      (A) NAME/KEY: Modified-site
      (B) LOCATION:2
      (D) OTHER INFORMATION:/product="His(Trt)"

(ix) FEATURE:

( A ) NAME/KEY: Modified-site
                    ( B ) LOCATION:3
                    ( D ) OTHER INFORMATION:/product="Lys(Boc)"

( i x ) FEATURE:
                    ( A ) NAME/KEY: Modified-site
                    ( B ) LOCATION:7
                    ( D ) OTHER INFORMATION:/product="Thr(But)"

( x i ) SEQUENCE DESCRIPTION: SEQ ID NO: 116:

Pro  His  Lys  Gly  Pro  Ala  Thr
1                     5

( 2 ) INFORMATION FOR SEQ ID NO: 117:

( i ) SEQUENCE CHARACTERISTICS:
                    ( A ) LENGTH: 7 amino acids
                    ( B ) TYPE: amino acid
                    ( C ) STRANDEDNESS:
                    ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
                    ( A ) NAME/KEY: Modified-site
                    ( B ) LOCATION:2
                    ( D ) OTHER INFORMATION:/product="His(Trt)"

( i x ) FEATURE:
                    ( A ) NAME/KEY: Modified-site
                    ( B ) LOCATION:3
                    ( D ) OTHER INFORMATION:/product="Lys(Boc)"

( i x ) FEATURE:
                    ( A ) NAME/KEY: Modified-site
                    ( B ) LOCATION:7
                    ( D ) OTHER INFORMATION:/product="Thr(But)"

( x i ) SEQUENCE DESCRIPTION: SEQ ID NO: 117:

Pro  His  Lys  Gly  Pro  Ala  Thr
1                     5

( 2 ) INFORMATION FOR SEQ ID NO: 118:

( i ) SEQUENCE CHARACTERISTICS:
                    ( A ) LENGTH: 4 amino acids
                    ( B ) TYPE: amino acid
                    ( C ) STRANDEDNESS:
                    ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
                    ( A ) NAME/KEY: Modified-site
                    ( B ) LOCATION:1
                    ( D ) OTHER INFORMATION:/product="Fmoc-Pro"

( i x ) FEATURE:
                    ( A ) NAME/KEY: Modified-site
                    ( B ) LOCATION:2
                    ( D ) OTHER INFORMATION:/product="His(Trt)"

( i x ) FEATURE:
                    ( A ) NAME/KEY: Modified-site (B) LOCATION:3
(D) OTHER INFORMATION:/product="Lys(Boc)"

(x i) SEQUENCE DESCRIPTION: SEQ ID NO: 118:

Pro His Lys Gly
1

(2) INFORMATION FOR SEQ ID NO: 119:

(i) SEQUENCE CHARACTERISTICS:
(A) LENGTH: 4 amino acids
(B) TYPE: amino acid
(C) STRANDEDNESS:
(D) TOPOLOGY: linear (i i) MOLECULE TYPE: peptide (i i i) HYPOTHETICAL: YES (i v) ANTI-SENSE: NO (v) FRAGMENT TYPE: N-terminal (i x) FEATURE:
(A) NAME/KEY: Modified-site
(B) LOCATION:2
(D) OTHER INFORMATION:/product="His(Trt)"

(i x) FEATURE:
(A) NAME/KEY: Modified-site
(B) LOCATION:3
(D) OTHER INFORMATION:/product="Lys(Boc)"

(x i) SEQUENCE DESCRIPTION: SEQ ID NO: 119:

Pro His Lys Gly
1

(2) INFORMATION FOR SEQ ID NO: 120:

(i) SEQUENCE CHARACTERISTICS:
(A) LENGTH: 6 amino acids
(B) TYPE: amino acid
(C) STRANDEDNESS:
(D) TOPOLOGY: linear (i i) MOLECULE TYPE: peptide (i i i) HYPOTHETICAL: YES (i v) ANTI-SENSE: NO (v) FRAGMENT TYPE: N-terminal (i x) FEATURE:
(A) NAME/KEY: Modified-site
(B) LOCATION:1
(D) OTHER INFORMATION:/product="Fmoc-Ala"

(i x) FEATURE:
(A) NAME/KEY: Modified-site
(B) LOCATION:2
(D) OTHER INFORMATION:/product="Asp(OBut)"

(i x) FEATURE:
(A) NAME/KEY: Modified-site
(B) LOCATION:3
(D) OTHER INFORMATION:/product="Cys(Trt)"

(i x) FEATURE:
(A) NAME/KEY: Modified-site
(B) LOCATION:5
(D) OTHER INFORMATION:/product="Arg(Mtr)"

(i x) FEATURE:
(A) NAME/KEY: Modified-site
(B) LOCATION:6

(D) OTHER INFORMATION:/product="Asn(Trt)"

(x i) SEQUENCE DESCRIPTION: SEQ ID NO: 120:

Ala Asp Cys Pro Arg Asn
1               5

(2) INFORMATION FOR SEQ ID NO: 121:

(i) SEQUENCE CHARACTERISTICS:
        (A) LENGTH: 9 amino acids
        (B) TYPE: amino acid
        (C) STRANDEDNESS:
        (D) TOPOLOGY: linear (i i) MOLECULE TYPE: peptide (i i i) HYPOTHETICAL: YES (i v) ANTI-SENSE: NO (v) FRAGMENT TYPE: N-terminal (i x) FEATURE:
        (A) NAME/KEY: Modified-site
        (B) LOCATION:1
        (D) OTHER INFORMATION:/product="Fmoc-Lys(Boc)"

(i x) FEATURE:
        (A) NAME/KEY: Modified-site
        (B) LOCATION:2
        (D) OTHER INFORMATION:/product="Thr(But)"

(i x) FEATURE:
        (A) NAME/KEY: Modified-site
        (B) LOCATION:4
        (D) OTHER INFORMATION:/product="Asp(OBut)"

(i x) FEATURE:
        (A) NAME/KEY: Modified-site
        (B) LOCATION:5
        (D) OTHER INFORMATION:/product="Cys(Trt)"

(i x) FEATURE:
        (A) NAME/KEY: Modified-site
        (B) LOCATION:7
        (D) OTHER INFORMATION:/product="Arg(Mtr)"

(i x) FEATURE:
        (A) NAME/KEY: Modified-site
        (B) LOCATION:8
        (D) OTHER INFORMATION:/product="Asn(Trt)"

(x i) SEQUENCE DESCRIPTION: SEQ ID NO: 121:

Lys Thr Ala Asp Cys Pro Arg Asn Pro
1               5

(2) INFORMATION FOR SEQ ID NO: 122:

(i) SEQUENCE CHARACTERISTICS:
        (A) LENGTH: 9 amino acids
        (B) TYPE: amino acid
        (C) STRANDEDNESS:
        (D) TOPOLOGY: linear (i i) MOLECULE TYPE: peptide (i i i) HYPOTHETICAL: YES (i v) ANTI-SENSE: NO (v) FRAGMENT TYPE: N-terminal (i x) FEATURE:
        (A) NAME/KEY: Modified-site
        (B) LOCATION:1
        (D) OTHER INFORMATION:/product="Fmoc-Gly"

( i x ) FEATURE:
  ( A ) NAME/KEY: Modified-site
  ( B ) LOCATION:2
  ( D ) OTHER INFORMATION:/product="Lys(Boc)"

( i x ) FEATURE:
  ( A ) NAME/KEY: Modified-site
  ( B ) LOCATION:3
  ( D ) OTHER INFORMATION:/product="Thr(But)"

( i x ) FEATURE:
  ( A ) NAME/KEY: Modified-site
  ( B ) LOCATION:4
  ( D ) OTHER INFORMATION:/product="Cys(Trt)"

( i x ) FEATURE:
  ( A ) NAME/KEY: Modified-site
  ( B ) LOCATION:5
  ( D ) OTHER INFORMATION:/product="Asp(OBut)"

( i x ) FEATURE:
  ( A ) NAME/KEY: Modified-site
  ( B ) LOCATION:6
  ( D ) OTHER INFORMATION:/product="Cys(Trt)"

( i x ) FEATURE:
  ( A ) NAME/KEY: Modified-site
  ( B ) LOCATION:8
  ( D ) OTHER INFORMATION:/product="Arg(Mtr)"

( i x ) FEATURE:
  ( A ) NAME/KEY: Modified-site
  ( B ) LOCATION:9
  ( D ) OTHER INFORMATION:/product="Asn(Trt)"

( x i ) SEQUENCE DESCRIPTION: SEQ ID NO: 122:

Gly Lys Thr Cys Asp Cys Pro Arg Asn
1       5

( 2 ) INFORMATION FOR SEQ ID NO: 123:

( i ) SEQUENCE CHARACTERISTICS:
  ( A ) LENGTH: 6 amino acids
  ( B ) TYPE: amino acid
  ( C ) STRANDEDNESS:
  ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
  ( A ) NAME/KEY: Modified-site
  ( B ) LOCATION:1
  ( D ) OTHER INFORMATION:/product="Boc-Thr(But)"

( i x ) FEATURE:
  ( A ) NAME/KEY: Modified-site
  ( B ) LOCATION:3
  ( D ) OTHER INFORMATION:/product="Asp(OBut)"

( i x ) FEATURE:
  ( A ) NAME/KEY: Modified-site
  ( B ) LOCATION:6
  ( D ) OTHER INFORMATION:/product="Arg(Mtr)"

( x i ) SEQUENCE DESCRIPTION: SEQ ID NO: 123:

Thr Ala Asp Cys Pro Arg
1     5

( 2 ) INFORMATION FOR SEQ ID NO: 124:

( i ) SEQUENCE CHARACTERISTICS:
    ( A ) LENGTH: 9 amino acids
    ( B ) TYPE: amino acid
    ( C ) STRANDEDNESS:
    ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
    ( A ) NAME/KEY: Modified-site
    ( B ) LOCATION:1
    ( D ) OTHER INFORMATION:/product="Fmoc-Gly"

( i x ) FEATURE:
    ( A ) NAME/KEY: Modified-site
    ( B ) LOCATION:2
    ( D ) OTHER INFORMATION:/product="Lys(Boc)"

( i x ) FEATURE:
    ( A ) NAME/KEY: Modified-site
    ( B ) LOCATION:3
    ( D ) OTHER INFORMATION:/product="Thr(But)"

( i x ) FEATURE:
    ( A ) NAME/KEY: Modified-site
    ( B ) LOCATION:5
    ( D ) OTHER INFORMATION:/product="Asp(OBut)"

( i x ) FEATURE:
    ( A ) NAME/KEY: Modified-site
    ( B ) LOCATION:6
    ( D ) OTHER INFORMATION:/product="Cys(Trt)"

( i x ) FEATURE:
    ( A ) NAME/KEY: Modified-site
    ( B ) LOCATION:8
    ( D ) OTHER INFORMATION:/product="Arg(Mtr)"

( i x ) FEATURE:
    ( A ) NAME/KEY: Modified-site
    ( B ) LOCATION:9
    ( D ) OTHER INFORMATION:/product="Asn(Trt)"

( x i ) SEQUENCE DESCRIPTION: SEQ ID NO: 124:

```
Gly Lys Thr Ala Asp Cys Pro Arg Asn
1               5
```

( 2 ) INFORMATION FOR SEQ ID NO: 125:

( i ) SEQUENCE CHARACTERISTICS:
    ( A ) LENGTH: 7 amino acids
    ( B ) TYPE: amino acid
    ( C ) STRANDEDNESS:
    ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
    ( A ) NAME/KEY: Modified-site
    ( B ) LOCATION:1
    ( D ) OTHER INFORMATION:/product="Fmoc-Thr(But)"

( i x ) FEATURE:
    ( A ) NAME/KEY: Modified-site
    ( B ) LOCATION:3

( D ) OTHER INFORMATION:/product="Asp(OBut)"

( i x ) FEATURE:
    ( A ) NAME/KEY: Modified-site
    ( B ) LOCATION:4
    ( D ) OTHER INFORMATION:/product="Cys(Trt)"

( i x ) FEATURE:
    ( A ) NAME/KEY: Modified-site
    ( B ) LOCATION:6
    ( D ) OTHER INFORMATION:/product="Arg(Mtr)"

( i x ) FEATURE:
    ( A ) NAME/KEY: Modified-site
    ( B ) LOCATION:7
    ( D ) OTHER INFORMATION:/product="Asn(Trt)"

( x i ) SEQUENCE DESCRIPTION: SEQ ID NO: 125:

Thr Ala Asp Cys Pro Arg Asn
1               5

( 2 ) INFORMATION FOR SEQ ID NO: 126:

( i ) SEQUENCE CHARACTERISTICS:
        ( A ) LENGTH: 7 amino acids
        ( B ) TYPE: amino acid
        ( C ) STRANDEDNESS:
        ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
        ( A ) NAME/KEY: Modified-site
        ( B ) LOCATION:2
        ( D ) OTHER INFORMATION:/product="His(Trt)"

( i x ) FEATURE:
        ( A ) NAME/KEY: Modified-site
        ( B ) LOCATION:3
        ( D ) OTHER INFORMATION:/product="Lys(Boc)"

( i x ) FEATURE:
        ( A ) NAME/KEY: Modified-site
        ( B ) LOCATION:7
        ( D ) OTHER INFORMATION:/product="Thr(But)"

( x i ) SEQUENCE DESCRIPTION: SEQ ID NO: 126:

Pro His Lys Gly Pro Ala Thr
1               5

( 2 ) INFORMATION FOR SEQ ID NO: 127:

( i ) SEQUENCE CHARACTERISTICS:
        ( A ) LENGTH: 6 amino acids
        ( B ) TYPE: amino acid
        ( C ) STRANDEDNESS:
        ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
        ( A ) NAME/KEY: Modified-site
        ( B ) LOCATION:1
        ( D ) OTHER INFORMATION:/product="Fmoc-Ala"

( i x ) FEATURE:
    ( A ) NAME/KEY: Modified-site
    ( B ) LOCATION:2
    ( D ) OTHER INFORMATION:/product="Asp(OBut)"

( i x ) FEATURE:
    ( A ) NAME/KEY: Modified-site
    ( B ) LOCATION:3
    ( D ) OTHER INFORMATION:/product="Cys(Trt)"

( i x ) FEATURE:
    ( A ) NAME/KEY: Modified-site
    ( B ) LOCATION:5
    ( D ) OTHER INFORMATION:/product="Arg(Mtr)"

( i x ) FEATURE:
    ( A ) NAME/KEY: Modified-site
    ( B ) LOCATION:6
    ( D ) OTHER INFORMATION:/product="Asn(Trt)"

( x i ) SEQUENCE DESCRIPTION: SEQ ID NO: 127:

Ala Asp Cys Pro Arg Asn
1               5

( 2 ) INFORMATION FOR SEQ ID NO: 128:

( i ) SEQUENCE CHARACTERISTICS:
    ( A ) LENGTH: 4 amino acids
    ( B ) TYPE: amino acid
    ( C ) STRANDEDNESS:
    ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
    ( A ) NAME/KEY: Modified-site
    ( B ) LOCATION:1
    ( D ) OTHER INFORMATION:/product="Fmoc-Thr(But)"

( i x ) FEATURE:
    ( A ) NAME/KEY: Modified-site
    ( B ) LOCATION:3
    ( D ) OTHER INFORMATION:/product="Asp(OBut)"

( i x ) FEATURE:
    ( A ) NAME/KEY: Modified-site
    ( B ) LOCATION:4
    ( D ) OTHER INFORMATION:/product="Cys(Trt)"

( x i ) SEQUENCE DESCRIPTION: SEQ ID NO: 128:

Thr Ala Asp Cys
1

( 2 ) INFORMATION FOR SEQ ID NO: 129:

( i ) SEQUENCE CHARACTERISTICS:
    ( A ) LENGTH: 5 amino acids
    ( B ) TYPE: amino acid
    ( C ) STRANDEDNESS:
    ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
    ( A ) NAME/KEY: Modified-site
    ( B ) LOCATION:1
    ( D ) OTHER INFORMATION:/product="Fmoc-Cys(Trt)"

( i x ) FEATURE:
    ( A ) NAME/KEY: Modified-site
    ( B ) LOCATION:3
    ( D ) OTHER INFORMATION:/product="Arg(Mtr)"

( i x ) FEATURE:
    ( A ) NAME/KEY: Modified-site
    ( B ) LOCATION:4
    ( D ) OTHER INFORMATION:/product="Asn(Trt)"

( x i ) SEQUENCE DESCRIPTION: SEQ ID NO: 129:

Cys Pro Arg Asn Pro
1               5

( 2 ) INFORMATION FOR SEQ ID NO: 130:

( i ) SEQUENCE CHARACTERISTICS:
        ( A ) LENGTH: 5 amino acids
        ( B ) TYPE: amino acid
        ( C ) STRANDEDNESS:
        ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
        ( A ) NAME/KEY: Modified-site
        ( B ) LOCATION:1
        ( D ) OTHER INFORMATION:/product="Cys(Trt)"

( i x ) FEATURE:
        ( A ) NAME/KEY: Modified-site
        ( B ) LOCATION:3
        ( D ) OTHER INFORMATION:/product="Arg(Mtr)"

( i x ) FEATURE:
        ( A ) NAME/KEY: Modified-site
        ( B ) LOCATION:4
        ( D ) OTHER INFORMATION:/product="Asn(Trt)"

( x i ) SEQUENCE DESCRIPTION: SEQ ID NO: 130:

Cys Pro Arg Asn Pro
1               5

( 2 ) INFORMATION FOR SEQ ID NO: 131:

( i ) SEQUENCE CHARACTERISTICS:
        ( A ) LENGTH: 7 amino acids
        ( B ) TYPE: amino acid
        ( C ) STRANDEDNESS:
        ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
        ( A ) NAME/KEY: Modified-site
        ( B ) LOCATION:1
        ( D ) OTHER INFORMATION:/product="Cys(Trt)"

( i x ) FEATURE:

( A ) NAME/KEY: Modified-site
                    ( B ) LOCATION:3
                    ( D ) OTHER INFORMATION:/product="Arg(Mtr)"

( i x ) FEATURE:
                    ( A ) NAME/KEY: Modified-site
                    ( B ) LOCATION:4
                    ( D ) OTHER INFORMATION:/product="Asn(Trt)"

( i x ) FEATURE:
                    ( A ) NAME/KEY: Modified-site
                    ( B ) LOCATION:6
                    ( D ) OTHER INFORMATION:/product="His(Trt)"

( i x ) FEATURE:
                    ( A ) NAME/KEY: Modified-site
                    ( B ) LOCATION:7
                    ( D ) OTHER INFORMATION:/product="Lys(Boc)"

( x i ) SEQUENCE DESCRIPTION: SEQ ID NO: 131:

Cys  Pro  Arg  Asn  Pro  His  Lys
          1                        5

( 2 ) INFORMATION FOR SEQ ID NO: 132:

( i ) SEQUENCE CHARACTERISTICS:
                    ( A ) LENGTH: 6 amino acids
                    ( B ) TYPE: amino acid
                    ( C ) STRANDEDNESS:
                    ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
                    ( A ) NAME/KEY: Modified-site
                    ( B ) LOCATION:1
                    ( D ) OTHER INFORMATION:/product="Cys(Trt)"

( i x ) FEATURE:
                    ( A ) NAME/KEY: Modified-site
                    ( B ) LOCATION:3
                    ( D ) OTHER INFORMATION:/product="Arg(Mtr)"

( i x ) FEATURE:
                    ( A ) NAME/KEY: Modified-site
                    ( B ) LOCATION:4
                    ( D ) OTHER INFORMATION:/product="Asn(Trt)"

( i x ) FEATURE:
                    ( A ) NAME/KEY: Modified-site
                    ( B ) LOCATION:6
                    ( D ) OTHER INFORMATION:/product="His(Trt)"

( x i ) SEQUENCE DESCRIPTION: SEQ ID NO: 132:

Cys  Pro  Arg  Asn  Pro  His
          1                        5

( 2 ) INFORMATION FOR SEQ ID NO: 133:

( i ) SEQUENCE CHARACTERISTICS:
                    ( A ) LENGTH: 8 amino acids
                    ( B ) TYPE: amino acid
                    ( C ) STRANDEDNESS:
                    ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
    ( A ) NAME/KEY: Modified-site
    ( B ) LOCATION:1
    ( D ) OTHER INFORMATION:/product="Cys(Trt)"

( i x ) FEATURE:
    ( A ) NAME/KEY: Modified-site
    ( B ) LOCATION:3
    ( D ) OTHER INFORMATION:/product="Arg(Mtr)"

( i x ) FEATURE:
    ( A ) NAME/KEY: Modified-site
    ( B ) LOCATION:4
    ( D ) OTHER INFORMATION:/product="Asn(Trt)"

( i x ) FEATURE:
    ( A ) NAME/KEY: Modified-site
    ( B ) LOCATION:6
    ( D ) OTHER INFORMATION:/product="His(Trt)"

( i x ) FEATURE:
    ( A ) NAME/KEY: Modified-site
    ( B ) LOCATION:7
    ( D ) OTHER INFORMATION:/product="Lys(Boc)"

( x i ) SEQUENCE DESCRIPTION: SEQ ID NO: 133:

Cys Pro Arg Asn Pro His Lys Gly
1               5

( 2 ) INFORMATION FOR SEQ ID NO: 134:

( i ) SEQUENCE CHARACTERISTICS:
        ( A ) LENGTH: 6 amino acids
        ( B ) TYPE: amino acid
        ( C ) STRANDEDNESS:
        ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
        ( A ) NAME/KEY: Modified-site
        ( B ) LOCATION:1
        ( D ) OTHER INFORMATION:/product="Fmoc-Ala"

( i x ) FEATURE:
        ( A ) NAME/KEY: Modified-site
        ( B ) LOCATION:2
        ( D ) OTHER INFORMATION:/product="Asp(OBut)"

( i x ) FEATURE:
        ( A ) NAME/KEY: Modified-site
        ( B ) LOCATION:3
        ( D ) OTHER INFORMATION:/product="Cys(Trt)"

( i x ) FEATURE:
        ( A ) NAME/KEY: Modified-site
        ( B ) LOCATION:5
        ( D ) OTHER INFORMATION:/product="Arg(Mtr)"

( i x ) FEATURE:
        ( A ) NAME/KEY: Modified-site
        ( B ) LOCATION:6
        ( D ) OTHER INFORMATION:/product="Asn(Trt)"

( x i ) SEQUENCE DESCRIPTION: SEQ ID NO: 134:

Ala Asp Cys Pro Arg Asn
1               5

( 2 ) INFORMATION FOR SEQ ID NO: 135:

( i ) SEQUENCE CHARACTERISTICS:
        ( A ) LENGTH: 13 amino acids
        ( B ) TYPE: amino acid
        ( C ) STRANDEDNESS:
        ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
        ( A ) NAME/KEY: Modified-site
        ( B ) LOCATION:1
        ( D ) OTHER INFORMATION:/product="Fmoc-Ala"

( i x ) FEATURE:
        ( A ) NAME/KEY: Modified-site
        ( B ) LOCATION:2
        ( D ) OTHER INFORMATION:/product="Asp(OBut)"

( i x ) FEATURE:
        ( A ) NAME/KEY: Modified-site
        ( B ) LOCATION:3
        ( D ) OTHER INFORMATION:/product="Cys(Trt)"

( i x ) FEATURE:
        ( A ) NAME/KEY: Modified-site
        ( B ) LOCATION:5
        ( D ) OTHER INFORMATION:/product="Arg(Mtr)"

( i x ) FEATURE:
        ( A ) NAME/KEY: Modified-site
        ( B ) LOCATION:6
        ( D ) OTHER INFORMATION:/product="Asn(Trt)"

( i x ) FEATURE:
        ( A ) NAME/KEY: Modified-site
        ( B ) LOCATION:8
        ( D ) OTHER INFORMATION:/product="His(Trt)"

( i x ) FEATURE:
        ( A ) NAME/KEY: Modified-site
        ( B ) LOCATION:9
        ( D ) OTHER INFORMATION:/product="Lys(Boc)"

( i x ) FEATURE:
        ( A ) NAME/KEY: Modified-site
        ( B ) LOCATION:13
        ( D ) OTHER INFORMATION:/product="Thr(But)"

( x i ) SEQUENCE DESCRIPTION: SEQ ID NO: 135:

```
Ala  Asp  Cys  Pro  Arg  Asn  Pro  His  Lys  Gly  Pro  Ala  Thr
 1                   5                   10
```

( 2 ) INFORMATION FOR SEQ ID NO: 136:

( i ) SEQUENCE CHARACTERISTICS:
        ( A ) LENGTH: 13 amino acids
        ( B ) TYPE: amino acid
        ( C ) STRANDEDNESS:
        ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:

( A ) NAME/KEY: Modified-site
                ( B ) LOCATION:3
                ( D ) OTHER INFORMATION:/product="Cys(Trt)"

( x i ) SEQUENCE DESCRIPTION: SEQ ID NO: 136:

Ala  Asp  Cys  Pro  Arg  Asn  Pro  His  Lys  Gly  Pro  Ala  Thr
1                   5                        10

( 2 ) INFORMATION FOR SEQ ID NO: 137:

( i ) SEQUENCE CHARACTERISTICS:
                ( A ) LENGTH: 7 amino acids
                ( B ) TYPE: amino acid
                ( C ) STRANDEDNESS:
                ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
                ( A ) NAME/KEY: Modified-site
                ( B ) LOCATION:2
                ( D ) OTHER INFORMATION:/product="His(Trt)"

( i x ) FEATURE:
                ( A ) NAME/KEY: Modified-site
                ( B ) LOCATION:3
                ( D ) OTHER INFORMATION:/product="Lys(Boc)"

( i x ) FEATURE:
                ( A ) NAME/KEY: Modified-site
                ( B ) LOCATION:7
                ( D ) OTHER INFORMATION:/product="Thr(But)"

( x i ) SEQUENCE DESCRIPTION: SEQ ID NO: 137:

Pro  His  Lys  Gly  Pro  Ala  Thr
1                   5

( 2 ) INFORMATION FOR SEQ ID NO: 138:

( i ) SEQUENCE CHARACTERISTICS:
                ( A ) LENGTH: 8 amino acids
                ( B ) TYPE: amino acid
                ( C ) STRANDEDNESS:
                ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
                ( A ) NAME/KEY: Modified-site
                ( B ) LOCATION:1
                ( D ) OTHER INFORMATION:/product="Fmoc-Lys(Boc)"

( i x ) FEATURE:
                ( A ) NAME/KEY: Modified-site
                ( B ) LOCATION:2
                ( D ) OTHER INFORMATION:/product="Thr(But)"

( i x ) FEATURE:
                ( A ) NAME/KEY: Modified-site
                ( B ) LOCATION:4
                ( D ) OTHER INFORMATION:/product="Asp(OBut)"

( i x ) FEATURE:
                ( A ) NAME/KEY: Modified-site ( B ) LOCATION:5
                    ( D ) OTHER INFORMATION:/product="Cys(Trt)"

( i x ) FEATURE:
                    ( A ) NAME/KEY: Modified-site
                    ( B ) LOCATION:7
                    ( D ) OTHER INFORMATION:/product="Arg(Mtr)"

( i x ) FEATURE:
                    ( A ) NAME/KEY: Modified-site
                    ( B ) LOCATION:8
                    ( D ) OTHER INFORMATION:/product="Asn(Trt)"

( x i ) SEQUENCE DESCRIPTION: SEQ ID NO: 138:

Lys  Thr  Ala  Asp  Cys  Pro  Arg  Asn
    1                        5

( 2 ) INFORMATION FOR SEQ ID NO: 139:

( i ) SEQUENCE CHARACTERISTICS:
                    ( A ) LENGTH: 15 amino acids
                    ( B ) TYPE: amino acid
                    ( C ) STRANDEDNESS:
                    ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
                    ( A ) NAME/KEY: Modified-site
                    ( B ) LOCATION:5
                    ( D ) OTHER INFORMATION:/product="Cys(Trt)"

( x i ) SEQUENCE DESCRIPTION: SEQ ID NO: 139:

Lys  Thr  Ala  Asp  Cys  Pro  Arg  Asn  Pro  His  Lys  Gly  Pro  Ala  Thr
    1                        5                        10                       15

( 2 ) INFORMATION FOR SEQ ID NO: 140:

( i ) SEQUENCE CHARACTERISTICS:
                    ( A ) LENGTH: 7 amino acids
                    ( B ) TYPE: amino acid
                    ( C ) STRANDEDNESS:
                    ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
                    ( A ) NAME/KEY: Modified-site
                    ( B ) LOCATION:2
                    ( D ) OTHER INFORMATION:/product="His(Trt)"

( i x ) FEATURE:
                    ( A ) NAME/KEY: Modified-site
                    ( B ) LOCATION:3
                    ( D ) OTHER INFORMATION:/product="Lys(Boc)"

( i x ) FEATURE:
                    ( A ) NAME/KEY: Modified-site
                    ( B ) LOCATION:7
                    ( D ) OTHER INFORMATION:/product="Thr(But)"

( x i ) SEQUENCE DESCRIPTION: SEQ ID NO: 140:

Pro  His  Lys  Gly  Pro  Ala  Thr ( 2 ) INFORMATION FOR SEQ ID NO: 141:

( i ) SEQUENCE CHARACTERISTICS:
        ( A ) LENGTH: 9 amino acids
        ( B ) TYPE: amino acid
        ( C ) STRANDEDNESS:
        ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
        ( A ) NAME/KEY: Modified-site
        ( B ) LOCATION:1
        ( D ) OTHER INFORMATION:/product="Fmoc-Gly"

( i x ) FEATURE:
        ( A ) NAME/KEY: Modified-site
        ( B ) LOCATION:2
        ( D ) OTHER INFORMATION:/product="Lys(Boc)"

( i x ) FEATURE:
        ( A ) NAME/KEY: Modified-site
        ( B ) LOCATION:3
        ( D ) OTHER INFORMATION:/product="Thr(But)"

( i x ) FEATURE:
        ( A ) NAME/KEY: Modified-site
        ( B ) LOCATION:4
        ( D ) OTHER INFORMATION:/product="Cys(Trt)"

( i x ) FEATURE:
        ( A ) NAME/KEY: Modified-site
        ( B ) LOCATION:5
        ( D ) OTHER INFORMATION:/product="Asp(OBut)"

( i x ) FEATURE:
        ( A ) NAME/KEY: Modified-site
        ( B ) LOCATION:6
        ( D ) OTHER INFORMATION:/product="Cys(Trt)"

( i x ) FEATURE:
        ( A ) NAME/KEY: Modified-site
        ( B ) LOCATION:8
        ( D ) OTHER INFORMATION:/product="Arg(Mtr)"

( i x ) FEATURE:
        ( A ) NAME/KEY: Modified-site
        ( B ) LOCATION:9
        ( D ) OTHER INFORMATION:/product="Asn(Trt)"

( x i ) SEQUENCE DESCRIPTION: SEQ ID NO: 141:

Gly Lys Thr Cys Asp Cys Pro Arg Asn
    1                  5

( 2 ) INFORMATION FOR SEQ ID NO: 142:

( i ) SEQUENCE CHARACTERISTICS:
        ( A ) LENGTH: 16 amino acids
        ( B ) TYPE: amino acid
        ( C ) STRANDEDNESS:
        ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
    ( A ) NAME/KEY: Modified-site
    ( B ) LOCATION: 4
    ( D ) OTHER INFORMATION:/product="Cys(Trt)"

( i x ) FEATURE:
    ( A ) NAME/KEY: Modified-site
    ( B ) LOCATION: 6
    ( D ) OTHER INFORMATION:/product="Cys(Trt)"

( x i ) SEQUENCE DESCRIPTION: SEQ ID NO: 142:

Gly Lys Thr Cys Asp Cys Pro Arg Asn Pro His Lys Gly Pro Ala Thr
1               5                   10                  15

( 2 ) INFORMATION FOR SEQ ID NO: 143:

( i ) SEQUENCE CHARACTERISTICS:
    ( A ) LENGTH: 4 amino acids
    ( B ) TYPE: amino acid
    ( C ) STRANDEDNESS:
    ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
    ( A ) NAME/KEY: Modified-site
    ( B ) LOCATION: 2
    ( D ) OTHER INFORMATION:/product="His(Trt)"

( i x ) FEATURE:
    ( A ) NAME/KEY: Modified-site
    ( B ) LOCATION: 3
    ( D ) OTHER INFORMATION:/product="Lys(Boc)"

( x i ) SEQUENCE DESCRIPTION: SEQ ID NO: 143:

Pro His Lys Gly
1

( 2 ) INFORMATION FOR SEQ ID NO: 144:

( i ) SEQUENCE CHARACTERISTICS:
    ( A ) LENGTH: 9 amino acids
    ( B ) TYPE: amino acid
    ( C ) STRANDEDNESS:
    ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
    ( A ) NAME/KEY: Modified-site
    ( B ) LOCATION: 1
    ( D ) OTHER INFORMATION:/product="Fmoc-Gly"

( i x ) FEATURE:
    ( A ) NAME/KEY: Modified-site
    ( B ) LOCATION: 2
    ( D ) OTHER INFORMATION:/product="Lys(Boc)"

( i x ) FEATURE:
    ( A ) NAME/KEY: Modified-site
    ( B ) LOCATION: 3
    ( D ) OTHER INFORMATION:/product="Thr(But)"

( i x ) FEATURE:
    ( A ) NAME/KEY: Modified-site
    ( B ) LOCATION:5
    ( D ) OTHER INFORMATION:/product="Asp(OBut)"

( i x ) FEATURE:
    ( A ) NAME/KEY: Modified-site
    ( B ) LOCATION:6
    ( D ) OTHER INFORMATION:/product="Cys(Trt)"

( i x ) FEATURE:
    ( A ) NAME/KEY: Modified-site
    ( B ) LOCATION:8
    ( D ) OTHER INFORMATION:/product="Arg(Mtr)"

( i x ) FEATURE:
    ( A ) NAME/KEY: Modified-site
    ( B ) LOCATION:9
    ( D ) OTHER INFORMATION:/product="Asn(Trt)"

( x i ) SEQUENCE DESCRIPTION: SEQ ID NO: 144:

Gly Lys Thr Ala Asp Cys Pro Arg Asn
1                   5

( 2 ) INFORMATION FOR SEQ ID NO: 145:

( i ) SEQUENCE CHARACTERISTICS:
      ( A ) LENGTH: 13 amino acids
      ( B ) TYPE: amino acid
      ( C ) STRANDEDNESS:
      ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
    ( A ) NAME/KEY: Modified-site
    ( B ) LOCATION:6
    ( D ) OTHER INFORMATION:/product="Cys(Trt)"

( x i ) SEQUENCE DESCRIPTION: SEQ ID NO: 145:

Gly Lys Thr Ala Asp Cys Pro Arg Asn Pro His Lys Gly
1                   5                       10

( 2 ) INFORMATION FOR SEQ ID NO: 146:

( i ) SEQUENCE CHARACTERISTICS:
      ( A ) LENGTH: 7 amino acids
      ( B ) TYPE: amino acid
      ( C ) STRANDEDNESS:
      ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
    ( A ) NAME/KEY: Modified-site
    ( B ) LOCATION:2
    ( D ) OTHER INFORMATION:/product="His(Trt)"

( i x ) FEATURE:
    ( A ) NAME/KEY: Modified-site
    ( B ) LOCATION:3
    ( D ) OTHER INFORMATION:/product="Lys(Boc)"

( i x ) FEATURE:

-continued ( A ) NAME/KEY: Modified-site
                    ( B ) LOCATION: 7
                    ( D ) OTHER INFORMATION:/product="Thr(But)"

( x i ) SEQUENCE DESCRIPTION: SEQ ID NO: 146:

Pro  His  Lys  Gly  Pro  Ala  Thr
    1                   5

( 2 ) INFORMATION FOR SEQ ID NO: 147:

( i ) SEQUENCE CHARACTERISTICS:
                    ( A ) LENGTH: 7 amino acids
                    ( B ) TYPE: amino acid
                    ( C ) STRANDEDNESS:
                    ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
                    ( A ) NAME/KEY: Modified-site
                    ( B ) LOCATION: 1
                    ( D ) OTHER INFORMATION:/product="Fmoc-Thr(But)"

( i x ) FEATURE:
                    ( A ) NAME/KEY: Modified-site
                    ( B ) LOCATION: 3
                    ( D ) OTHER INFORMATION:/product="Asp(OBut)"

( i x ) FEATURE:
                    ( A ) NAME/KEY: Modified-site
                    ( B ) LOCATION: 4
                    ( D ) OTHER INFORMATION:/product="Cys(Trt)"

( i x ) FEATURE:
                    ( A ) NAME/KEY: Modified-site
                    ( B ) LOCATION: 6
                    ( D ) OTHER INFORMATION:/product="Arg(Mtr)"

( i x ) FEATURE:
                    ( A ) NAME/KEY: Modified-site
                    ( B ) LOCATION: 7
                    ( D ) OTHER INFORMATION:/product="Asn(Trt)"

( x i ) SEQUENCE DESCRIPTION: SEQ ID NO: 147:

Thr  Ala  Asp  Cys  Pro  Arg  Asn
    1                   5

( 2 ) INFORMATION FOR SEQ ID NO: 148:

( i ) SEQUENCE CHARACTERISTICS:
                    ( A ) LENGTH: 14 amino acids
                    ( B ) TYPE: amino acid
                    ( C ) STRANDEDNESS:
                    ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( x i ) SEQUENCE DESCRIPTION: SEQ ID NO: 148:

Thr  Ala  Asp  Cys  Pro  Arg  Asn  Pro  His  Lys  Gly  Pro  Ala  Thr
    1                   5                           10

( 2 ) INFORMATION FOR SEQ ID NO: 149:

( i ) SEQUENCE CHARACTERISTICS:
   ( A ) LENGTH: 7 amino acids
   ( B ) TYPE: amino acid
   ( C ) STRANDEDNESS:
   ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
   ( A ) NAME/KEY: Modified-site
   ( B ) LOCATION:2
   ( D ) OTHER INFORMATION:/product="His(Trt)"

( i x ) FEATURE:
   ( A ) NAME/KEY: Modified-site
   ( B ) LOCATION:3
   ( D ) OTHER INFORMATION:/product="Lys(Boc)"

( i x ) FEATURE:
   ( A ) NAME/KEY: Modified-site
   ( B ) LOCATION:7
   ( D ) OTHER INFORMATION:/product="Thr(But)-OMe"

( x i ) SEQUENCE DESCRIPTION: SEQ ID NO: 149:

Pro His Lys Gly Pro Ala Thr
1               5

( 2 ) INFORMATION FOR SEQ ID NO: 150:

( i ) SEQUENCE CHARACTERISTICS:
   ( A ) LENGTH: 6 amino acids
   ( B ) TYPE: amino acid
   ( C ) STRANDEDNESS:
   ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
   ( A ) NAME/KEY: Modified-site
   ( B ) LOCATION:1
   ( D ) OTHER INFORMATION:/product="Boc-Ala"

( i x ) FEATURE:
   ( A ) NAME/KEY: Modified-site
   ( B ) LOCATION:2
   ( D ) OTHER INFORMATION:/product="Asp(OBut)"

( i x ) FEATURE:
   ( A ) NAME/KEY: Modified-site
   ( B ) LOCATION:3
   ( D ) OTHER INFORMATION:/product="Cys(Trt)"

( i x ) FEATURE:
   ( A ) NAME/KEY: Modified-site
   ( B ) LOCATION:5
   ( D ) OTHER INFORMATION:/product="Arg(Mtr)"

( i x ) FEATURE:
   ( A ) NAME/KEY: Modified-site
   ( B ) LOCATION:6
   ( D ) OTHER INFORMATION:/product="Asn(Trt)"

( x i ) SEQUENCE DESCRIPTION: SEQ ID NO: 150:

Ala Asp Cys Pro Arg Asn ( 2 ) INFORMATION FOR SEQ ID NO: 151:

( i ) SEQUENCE CHARACTERISTICS:
       ( A ) LENGTH: 13 amino acids
       ( B ) TYPE: amino acid
       ( C ) STRANDEDNESS:
       ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( x i ) SEQUENCE DESCRIPTION: SEQ ID NO: 151:

Ala Asp Cys Pro Arg Asn Pro His Lys Gly Pro Ala Thr
   1               5                   10

( 2 ) INFORMATION FOR SEQ ID NO: 152:

( i ) SEQUENCE CHARACTERISTICS:
       ( A ) LENGTH: 4 amino acids
       ( B ) TYPE: amino acid
       ( C ) STRANDEDNESS:
       ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
       ( A ) NAME/KEY: Modified-site
       ( B ) LOCATION:2
       ( D ) OTHER INFORMATION:/product="His(Trt)"

( i x ) FEATURE:
       ( A ) NAME/KEY: Modified-site
       ( B ) LOCATION:3
       ( D ) OTHER INFORMATION:/product="Lys(Boc)"

( i x ) FEATURE:
       ( A ) NAME/KEY: Modified-site
       ( B ) LOCATION:4
       ( D ) OTHER INFORMATION:/product="Gly-OMe"

( x i ) SEQUENCE DESCRIPTION: SEQ ID NO: 152:

Pro His Lys Gly
   1

( 2 ) INFORMATION FOR SEQ ID NO: 153:

( i ) SEQUENCE CHARACTERISTICS:
       ( A ) LENGTH: 6 amino acids
       ( B ) TYPE: amino acid
       ( C ) STRANDEDNESS:
       ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
       ( A ) NAME/KEY: Modified-site ( B ) LOCATION:1
( D ) OTHER INFORMATION:/product="Boc-Ala"

( i x ) FEATURE:
    ( A ) NAME/KEY: Modified-site
    ( B ) LOCATION:2
    ( D ) OTHER INFORMATION:/product="Asp(OBut)"

( i x ) FEATURE:
    ( A ) NAME/KEY: Modified-site
    ( B ) LOCATION:3
    ( D ) OTHER INFORMATION:/product="Cys(Trt)"

( i x ) FEATURE:
    ( A ) NAME/KEY: Modified-site
    ( B ) LOCATION:5
    ( D ) OTHER INFORMATION:/product="Arg(Mtr)"

( i x ) FEATURE:
    ( A ) NAME/KEY: Modified-site
    ( B ) LOCATION:6
    ( D ) OTHER INFORMATION:/product="Asn(Trt)"

( x i ) SEQUENCE DESCRIPTION: SEQ ID NO: 153:

Ala  Asp  Cys  Pro  Arg  Asn
1                    5

( 2 ) INFORMATION FOR SEQ ID NO: 154:

( i ) SEQUENCE CHARACTERISTICS:
        ( A ) LENGTH: 10 amino acids
        ( B ) TYPE: amino acid
        ( C ) STRANDEDNESS:
        ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( x i ) SEQUENCE DESCRIPTION: SEQ ID NO: 154:

Ala  Asp  Cys  Pro  Arg  Asn  Pro  His  Lys  Gly
1                    5                         10

( 2 ) INFORMATION FOR SEQ ID NO: 155:

( i ) SEQUENCE CHARACTERISTICS:
        ( A ) LENGTH: 4 amino acids
        ( B ) TYPE: amino acid
        ( C ) STRANDEDNESS:
        ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
        ( A ) NAME/KEY: Modified-site
        ( B ) LOCATION:2
        ( D ) OTHER INFORMATION:/product="His(Trt)"

( i x ) FEATURE:
        ( A ) NAME/KEY: Modified-site
        ( B ) LOCATION:3
        ( D ) OTHER INFORMATION:/product="Lys(Boc)"

( i x ) FEATURE:
        ( A ) NAME/KEY: Modified-site
        ( B ) LOCATION:4

-continued ( D ) OTHER INFORMATION:/product="Gly-OMe"

( x i ) SEQUENCE DESCRIPTION: SEQ ID NO: 155:

Pro  His  Lys  Gly
      1

( 2 ) INFORMATION FOR SEQ ID NO: 156:

( i ) SEQUENCE CHARACTERISTICS:
          ( A ) LENGTH: 9 amino acids
          ( B ) TYPE: amino acid
          ( C ) STRANDEDNESS:
          ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
          ( A ) NAME/KEY: Modified-site
          ( B ) LOCATION:1
          ( D ) OTHER INFORMATION:/product="Boc-Gly"

( i x ) FEATURE:
          ( A ) NAME/KEY: Modified-site
          ( B ) LOCATION:2
          ( D ) OTHER INFORMATION:/product="Lys(Boc)"

( i x ) FEATURE:
          ( A ) NAME/KEY: Modified-site
          ( B ) LOCATION:3
          ( D ) OTHER INFORMATION:/product="Thr(But)"

( i x ) FEATURE:
          ( A ) NAME/KEY: Modified-site
          ( B ) LOCATION:5
          ( D ) OTHER INFORMATION:/product="Asp(OBut)"

( i x ) FEATURE:
          ( A ) NAME/KEY: Modified-site
          ( B ) LOCATION:6
          ( D ) OTHER INFORMATION:/product="Cys(Trt)"

( i x ) FEATURE:
          ( A ) NAME/KEY: Modified-site
          ( B ) LOCATION:8
          ( D ) OTHER INFORMATION:/product="Arg(Mtr)"

( i x ) FEATURE:
          ( A ) NAME/KEY: Modified-site
          ( B ) LOCATION:9
          ( D ) OTHER INFORMATION:/product="Asn(Trt)"

( x i ) SEQUENCE DESCRIPTION: SEQ ID NO: 156:

Gly  Lys  Thr  Ala  Asp  Cys  Pro  Arg  Asn
      1                     5

( 2 ) INFORMATION FOR SEQ ID NO: 157:

( i ) SEQUENCE CHARACTERISTICS:
          ( A ) LENGTH: 13 amino acids
          ( B ) TYPE: amino acid
          ( C ) STRANDEDNESS:
          ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
  ( A ) NAME/KEY: Modified-site
  ( B ) LOCATION:6
  ( D ) OTHER INFORMATION:/product="Cys(Trt)"

( x i ) SEQUENCE DESCRIPTION: SEQ ID NO: 157:

Gly Lys Thr Ala Asp Cys Pro Arg Asn Pro His Lys Gly
1     5         10

( 2 ) INFORMATION FOR SEQ ID NO: 158:

( i ) SEQUENCE CHARACTERISTICS:
  ( A ) LENGTH: 7 amino acids
  ( B ) TYPE: amino acid
  ( C ) STRANDEDNESS:
  ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
  ( A ) NAME/KEY: Modified-site
  ( B ) LOCATION:2
  ( D ) OTHER INFORMATION:/product="His(trt)"

( i x ) FEATURE:
  ( A ) NAME/KEY: Modified-site
  ( B ) LOCATION:3
  ( D ) OTHER INFORMATION:/product="Lys(Boc)"

( i x ) FEATURE:
  ( A ) NAME/KEY: Modified-site
  ( B ) LOCATION:7
  ( D ) OTHER INFORMATION:/product="Thr(But)-OMe"

( x i ) SEQUENCE DESCRIPTION: SEQ ID NO: 158:

Pro His Lys Gly Pro Ala Thr
1     5

( 2 ) INFORMATION FOR SEQ ID NO: 159:

( i ) SEQUENCE CHARACTERISTICS:
  ( A ) LENGTH: 15 amino acids
  ( B ) TYPE: amino acid
  ( C ) STRANDEDNESS:
  ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( x i ) SEQUENCE DESCRIPTION: SEQ ID NO: 159:

Lys Thr Ala Asp Cys Pro Arg Asn Pro His Lys Gly Pro Ala Thr
1     5         10        15

( 2 ) INFORMATION FOR SEQ ID NO: 160:

( i ) SEQUENCE CHARACTERISTICS:
  ( A ) LENGTH: 9 amino acids
  ( B ) TYPE: amino acid
  ( C ) STRANDEDNESS:
  ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
    ( A ) NAME/KEY: Modified-site
    ( B ) LOCATION:5
    ( D ) OTHER INFORMATION:/product="Cys(Trt)"

( x i ) SEQUENCE DESCRIPTION: SEQ ID NO: 160:

```
Lys Thr Ala Asp Cys Pro Arg Asn Pro
 1               5
```

( 2 ) INFORMATION FOR SEQ ID NO: 161:

( i ) SEQUENCE CHARACTERISTICS:
    ( A ) LENGTH: 11 amino acids
    ( B ) TYPE: amino acid
    ( C ) STRANDEDNESS:
    ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
    ( A ) NAME/KEY: Modified-site
    ( B ) LOCATION:5
    ( D ) OTHER INFORMATION:/product="Cys(Trt)"

( x i ) SEQUENCE DESCRIPTION: SEQ ID NO: 161:

```
Lys Thr Ala Asp Cys Pro Arg Asn Pro His Lys
 1               5                   10
```

( 2 ) INFORMATION FOR SEQ ID NO: 162:

( i ) SEQUENCE CHARACTERISTICS:
    ( A ) LENGTH: 7 amino acids
    ( B ) TYPE: amino acid
    ( C ) STRANDEDNESS:
    ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
    ( A ) NAME/KEY: Modified-site
    ( B ) LOCATION:5
    ( D ) OTHER INFORMATION:/product="Cys(Trt)"

( x i ) SEQUENCE DESCRIPTION: SEQ ID NO: 162:

```
Lys Thr Ala Asp Cys Pro Arg
 1               5
```

( 2 ) INFORMATION FOR SEQ ID NO: 163:

( i ) SEQUENCE CHARACTERISTICS:
    ( A ) LENGTH: 8 amino acids
    ( B ) TYPE: amino acid
    ( C ) STRANDEDNESS:
    ( D ) TOPOLOGY: linear (ii) MOLECULE TYPE: peptide (iii) HYPOTHETICAL: YES (iv) ANTI-SENSE: NO (v) FRAGMENT TYPE: N-terminal (ix) FEATURE:
    (A) NAME/KEY: Modified-site
    (B) LOCATION:2
    (D) OTHER INFORMATION:/product="Cys(Trt)"

(xi) SEQUENCE DESCRIPTION: SEQ ID NO: 163:

```
Asp Cys Pro Arg Asn Pro His Lys
1               5
```

(2) INFORMATION FOR SEQ ID NO: 164:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (iii) HYPOTHETICAL: YES (iv) ANTI-SENSE: NO (v) FRAGMENT TYPE: N-terminal (ix) FEATURE:
    (A) NAME/KEY: Modified-site
    (B) LOCATION:3
    (D) OTHER INFORMATION:/product="Cys(Trt)"

(xi) SEQUENCE DESCRIPTION: SEQ ID NO: 164:

```
Ala Asp Cys Pro Arg
1               5
```

(2) INFORMATION FOR SEQ ID NO: 165:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (iii) HYPOTHETICAL: YES (iv) ANTI-SENSE: NO (v) FRAGMENT TYPE: N-terminal (ix) FEATURE:
    (A) NAME/KEY: Modified-site
    (B) LOCATION:4
    (D) OTHER INFORMATION:/product="Cys(Trt)"

(xi) SEQUENCE DESCRIPTION: SEQ ID NO: 165:

```
Thr Ala Asp Cys Pro Arg
1               5
```

(2) INFORMATION FOR SEQ ID NO: 166:

(i) SEQUENCE CHARACTERISTICS:
        (A) LENGTH: 8 amino acids
        (B) TYPE: amino acid
        (C) STRANDEDNESS:
        (D) TOPOLOGY: linear (  i  i  ) MOLECULE TYPE: peptide (  i  i  i  ) HYPOTHETICAL: YES (  i  v  ) ANTI-SENSE: NO (  v  ) FRAGMENT TYPE: N-terminal (  i  x  ) FEATURE:
    ( A ) NAME/KEY: Modified-site
    ( B ) LOCATION:2
    ( D ) OTHER INFORMATION:/product="Cys(Trt)"

(  i  x  ) FEATURE:
    ( A ) NAME/KEY: Modified-site
    ( B ) LOCATION:1
    ( D ) OTHER INFORMATION:/product="Acetyl-Asp"

(  x  i  ) SEQUENCE DESCRIPTION: SEQ ID NO: 166:

Asp Cys Pro Arg Asn Pro His Lys
1               5

( 2 ) INFORMATION FOR SEQ ID NO: 167:

( i ) SEQUENCE CHARACTERISTICS:
        ( A ) LENGTH: 5 amino acids
        ( B ) TYPE: amino acid
        ( C ) STRANDEDNESS:
        ( D ) TOPOLOGY: linear ( i  i ) MOLECULE TYPE: peptide ( i  i  i ) HYPOTHETICAL: YES ( i  v ) ANTI-SENSE: NO ( v ) FRAGMENT TYPE: N-terminal ( i  x ) FEATURE:
        ( A ) NAME/KEY: Modified-site
        ( B ) LOCATION:4
        ( D ) OTHER INFORMATION:/product="Cys(Trt)"

( x  i ) SEQUENCE DESCRIPTION: SEQ ID NO: 167:

Thr Ala Asp Cys Pro
1               5

( 2 ) INFORMATION FOR SEQ ID NO: 168:

( i ) SEQUENCE CHARACTERISTICS:
        ( A ) LENGTH: 6 amino acids
        ( B ) TYPE: amino acid
        ( C ) STRANDEDNESS:
        ( D ) TOPOLOGY: linear ( i  i ) MOLECULE TYPE: peptide ( i  i  i ) HYPOTHETICAL: YES ( i  v ) ANTI-SENSE: NO ( v ) FRAGMENT TYPE: N-terminal ( i  x ) FEATURE:
        ( A ) NAME/KEY: Modified-site
        ( B ) LOCATION:1
        ( D ) OTHER INFORMATION:/product="Ac-Lys"

( i  x ) FEATURE:
        ( A ) NAME/KEY: Modified-site
        ( B ) LOCATION:5
        ( D ) OTHER INFORMATION:/product="Cys(Trt)"

( x  i ) SEQUENCE DESCRIPTION: SEQ ID NO: 168:

```
Lys  Thr  Ala  Asp  Cys  Pro
1                   5
```

( 2 ) INFORMATION FOR SEQ ID NO: 169:

( i ) SEQUENCE CHARACTERISTICS:
        ( A ) LENGTH: 6 amino acids
        ( B ) TYPE: amino acid
        ( C ) STRANDEDNESS:
        ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
        ( A ) NAME/KEY: Modified-site
        ( B ) LOCATION:1
        ( D ) OTHER INFORMATION:/product="Ac-Gln"

( i x ) FEATURE:
        ( A ) NAME/KEY: Modified-site
        ( B ) LOCATION:5
        ( D ) OTHER INFORMATION:/product="Cys(Trt)"

( x i ) SEQUENCE DESCRIPTION: SEQ ID NO: 169:

```
Gln  Ser  Ala  Asp  Cys  Pro
1                   5
```

( 2 ) INFORMATION FOR SEQ ID NO: 170:

( i ) SEQUENCE CHARACTERISTICS:
        ( A ) LENGTH: 10 amino acids
        ( B ) TYPE: amino acid
        ( C ) STRANDEDNESS:
        ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
        ( A ) NAME/KEY: Modified-site
        ( B ) LOCATION:5
        ( D ) OTHER INFORMATION:/product="Cys(Trt)"

( i x ) FEATURE:
        ( A ) NAME/KEY: Modified-site
        ( B ) LOCATION:10
        ( D ) OTHER INFORMATION:/product="His-NH2"

( x i ) SEQUENCE DESCRIPTION: SEQ ID NO: 170:

```
Lys  Thr  Ala  Asp  Cys  Pro  Arg  Asn  Pro  His
1                   5                        10
```

( 2 ) INFORMATION FOR SEQ ID NO: 171:

( i ) SEQUENCE CHARACTERISTICS:
        ( A ) LENGTH: 6 amino acids
        ( B ) TYPE: amino acid
        ( C ) STRANDEDNESS:
        ( D ) TOPOLOGY: linear ( i i ) MOLECULE TYPE: peptide ( i i i ) HYPOTHETICAL: YES (iv) ANTI-SENSE: NO (v) FRAGMENT TYPE: N-terminal (ix) FEATURE:
    (A) NAME/KEY: Modified-site
    (B) LOCATION:5
    (D) OTHER INFORMATION:/product="Cys(Trt)"

(ix) FEATURE:
    (A) NAME/KEY: Modified-site
    (B) LOCATION:6
    (D) OTHER INFORMATION:/product="Pro-NH2"

(xi) SEQUENCE DESCRIPTION: SEQ ID NO: 171:

Lys Thr Ala Asp Cys Pro
1                 5

(2) INFORMATION FOR SEQ ID NO: 172:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (iii) HYPOTHETICAL: YES (iv) ANTI-SENSE: NO (v) FRAGMENT TYPE: N-terminal (ix) FEATURE:
    (A) NAME/KEY: Modified-site
    (B) LOCATION:5
    (D) OTHER INFORMATION:/product="Cys(Trt)"

(ix) FEATURE:
    (A) NAME/KEY: Modified-site
    (B) LOCATION:11
    (D) OTHER INFORMATION:/product="Lys-NH2"

(xi) SEQUENCE DESCRIPTION: SEQ ID NO: 172:

Lys Thr Ala Asp Cys Pro Arg Asn Pro His Lys
1                 5                       10

(2) INFORMATION FOR SEQ ID NO: 173:

(i) SEQUENCE CHARACTERISTICS:
        (A) LENGTH: 12 amino acids
        (B) TYPE: amino acid
        (C) STRANDEDNESS:
        (D) TOPOLOGY: linear (ii) MOLECULE TYPE: peptide (iii) HYPOTHETICAL: YES (iv) ANTI-SENSE: NO (v) FRAGMENT TYPE: N-terminal (ix) FEATURE:
    (A) NAME/KEY: Modified-site
    (B) LOCATION:5
    (D) OTHER INFORMATION:/product="Cys(Trt)"

(ix) FEATURE:
    (A) NAME/KEY: Modified-site
    (B) LOCATION:12
    (D) OTHER INFORMATION:/product="Gly-NH2"

(xi) SEQUENCE DESCRIPTION: SEQ ID NO: 173:

```
Lys  Thr  Ala  Asp  Cys  Pro  Arg  Asn  Pro  His  Lys  Gly
1                  5                      10
```

( 2 ) INFORMATION FOR SEQ ID NO: 174:

( i ) SEQUENCE CHARACTERISTICS:
        ( A ) LENGTH: 7 amino acids
        ( B ) TYPE: amino acid
        ( C ) STRANDEDNESS:
        ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
        ( A ) NAME/KEY: Modified-site
        ( B ) LOCATION:5
        ( D ) OTHER INFORMATION:/product="Cys(Trt)"

( i x ) FEATURE:
        ( A ) NAME/KEY: Modified-site
        ( B ) LOCATION:7
        ( D ) OTHER INFORMATION:/product="Arg-NH2"

( x i ) SEQUENCE DESCRIPTION: SEQ ID NO: 174:

```
Lys  Thr  Ala  Asp  Cys  Pro  Arg
1                  5
```

( 2 ) INFORMATION FOR SEQ ID NO: 175:

( i ) SEQUENCE CHARACTERISTICS:
        ( A ) LENGTH: 8 amino acids
        ( B ) TYPE: amino acid
        ( C ) STRANDEDNESS:
        ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
        ( A ) NAME/KEY: Modified-site
        ( B ) LOCATION:2
        ( D ) OTHER INFORMATION:/product="Cys(Trt)"

( i x ) FEATURE:
        ( A ) NAME/KEY: Modified-site
        ( B ) LOCATION:8
        ( D ) OTHER INFORMATION:/product="Lys-NH2"

( x i ) SEQUENCE DESCRIPTION: SEQ ID NO: 175:

```
Asp  Cys  Pro  Arg  Asn  Pro  His  Lys
1                  5
```

( 2 ) INFORMATION FOR SEQ ID NO: 176:

( i ) SEQUENCE CHARACTERISTICS:
        ( A ) LENGTH: 5 amino acids
        ( B ) TYPE: amino acid
        ( C ) STRANDEDNESS:
        ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
    ( A ) NAME/KEY: Modified-site
    ( B ) LOCATION:3
    ( D ) OTHER INFORMATION:/product="Cys(Trt)"

( i x ) FEATURE:
    ( A ) NAME/KEY: Modified-site
    ( B ) LOCATION:5
    ( D ) OTHER INFORMATION:/product="Arg-NH2"

( x i ) SEQUENCE DESCRIPTION: SEQ ID NO: 176:

Ala Asp Cys Pro Arg
1                 5

( 2 ) INFORMATION FOR SEQ ID NO: 177:

( i ) SEQUENCE CHARACTERISTICS:
    ( A ) LENGTH: 6 amino acids
    ( B ) TYPE: amino acid
    ( C ) STRANDEDNESS:
    ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
    ( A ) NAME/KEY: Modified-site
    ( B ) LOCATION:4
    ( D ) OTHER INFORMATION:/product="Cys(Trt)"

( i x ) FEATURE:
    ( A ) NAME/KEY: Modified-site
    ( B ) LOCATION:6
    ( D ) OTHER INFORMATION:/product="Arg-NH2"

( x i ) SEQUENCE DESCRIPTION: SEQ ID NO: 177:

Thr Ala Asp Cys Pro Arg
1                 5

( 2 ) INFORMATION FOR SEQ ID NO: 178:

( i ) SEQUENCE CHARACTERISTICS:
    ( A ) LENGTH: 6 amino acids
    ( B ) TYPE: amino acid
    ( C ) STRANDEDNESS:
    ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
    ( A ) NAME/KEY: Modified-site
    ( B ) LOCATION:5
    ( D ) OTHER INFORMATION:/product="Cys(Trt)"

( i x ) FEATURE:
    ( A ) NAME/KEY: Modified-site
    ( B ) LOCATION:6
    ( D ) OTHER INFORMATION:/product="Pro-NH2"

( x i ) SEQUENCE DESCRIPTION: SEQ ID NO: 178:

Lys Thr Ala Asp Cys Pro
1               5

( 2 ) INFORMATION FOR SEQ ID NO: 179:

( i ) SEQUENCE CHARACTERISTICS:
        ( A ) LENGTH: 5 amino acids
        ( B ) TYPE: amino acid
        ( C ) STRANDEDNESS:
        ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
        ( A ) NAME/KEY: Modified-site
        ( B ) LOCATION:4
        ( D ) OTHER INFORMATION:/product="Cys(Trt)"

( i x ) FEATURE:
        ( A ) NAME/KEY: Modified-site
        ( B ) LOCATION:5
        ( D ) OTHER INFORMATION:/product="Pro-NH2"

( x i ) SEQUENCE DESCRIPTION: SEQ ID NO: 179:

Thr Ala Asp Cys Pro
1               5

( 2 ) INFORMATION FOR SEQ ID NO: 180:

( i ) SEQUENCE CHARACTERISTICS:
        ( A ) LENGTH: 6 amino acids
        ( B ) TYPE: amino acid
        ( C ) STRANDEDNESS:
        ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
        ( A ) NAME/KEY: Modified-site
        ( B ) LOCATION:1
        ( D ) OTHER INFORMATION:/product="Ac-Lys"

( i x ) FEATURE:
        ( A ) NAME/KEY: Modified-site
        ( B ) LOCATION:5
        ( D ) OTHER INFORMATION:/product="Cys(Trt)"

( i x ) FEATURE:
        ( A ) NAME/KEY: Modified-site
        ( B ) LOCATION:6
        ( D ) OTHER INFORMATION:/product="Pro-NH2"

( x i ) SEQUENCE DESCRIPTION: SEQ ID NO: 180:

Lys Thr Ala Asp Cys Pro
1               5

( 2 ) INFORMATION FOR SEQ ID NO: 181:

( i ) SEQUENCE CHARACTERISTICS:
        ( A ) LENGTH: 11 amino acids
        ( B ) TYPE: amino acid
        ( C ) STRANDEDNESS:
        ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
    ( A ) NAME/KEY: Modified-site
    ( B ) LOCATION:1
    ( D ) OTHER INFORMATION:/product="Ac-Lys"

( i x ) FEATURE:
    ( A ) NAME/KEY: Modified-site
    ( B ) LOCATION:5
    ( D ) OTHER INFORMATION:/product="Cys(Trt)"

( i x ) FEATURE:
    ( A ) NAME/KEY: Modified-site
    ( B ) LOCATION:11
    ( D ) OTHER INFORMATION:/product="Lys-NH2"

( x i ) SEQUENCE DESCRIPTION: SEQ ID NO: 181:

```
Lys  Thr  Ala  Asp  Cys  Pro  Arg  Asn  Pro  His  Lys
1                   5                        10
```

( 2 ) INFORMATION FOR SEQ ID NO: 182:

( i ) SEQUENCE CHARACTERISTICS:
        ( A ) LENGTH: 7 amino acids
        ( B ) TYPE: amino acid
        ( C ) STRANDEDNESS:
        ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
    ( A ) NAME/KEY: Modified-site
    ( B ) LOCATION:1
    ( D ) OTHER INFORMATION:/product="Ac-Lys"

( i x ) FEATURE:
    ( A ) NAME/KEY: Modified-site
    ( B ) LOCATION:5
    ( D ) OTHER INFORMATION:/product="Cys(Trt)"

( i x ) FEATURE:
    ( A ) NAME/KEY: Modified-site
    ( B ) LOCATION:7
    ( D ) OTHER INFORMATION:/product="Arg-NH2"

( x i ) SEQUENCE DESCRIPTION: SEQ ID NO: 182:

```
Lys  Thr  Ala  Asp  Cys  Pro  Arg
1                   5
```

( 2 ) INFORMATION FOR SEQ ID NO: 183:

( i ) SEQUENCE CHARACTERISTICS:
        ( A ) LENGTH: 6 amino acids
        ( B ) TYPE: amino acid
        ( C ) STRANDEDNESS:
        ( D ) TOPOLOGY: linear ( i i ) MOLECULE TYPE: peptide ( i i i ) HYPOTHETICAL: YES ( i v ) ANTI-SENSE: NO (v) FRAGMENT TYPE: N-terminal (ix) FEATURE:
    (A) NAME/KEY: Modified-site
    (B) LOCATION:1
    (D) OTHER INFORMATION:/product="Ac-Thr"

(ix) FEATURE:
    (A) NAME/KEY: Modified-site
    (B) LOCATION:4
    (D) OTHER INFORMATION:/product="Cys(Trt)"

(ix) FEATURE:
    (A) NAME/KEY: Modified-site
    (B) LOCATION:6
    (D) OTHER INFORMATION:/product="Arg-NH2"

(xi) SEQUENCE DESCRIPTION: SEQ ID NO: 183:

Thr Ala Asp Cys Pro Arg
1               5

(2) INFORMATION FOR SEQ ID NO: 184:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (iii) HYPOTHETICAL: YES (iv) ANTI-SENSE: NO (v) FRAGMENT TYPE: N-terminal (ix) FEATURE:
        (A) NAME/KEY: Modified-site
        (B) LOCATION:5
        (D) OTHER INFORMATION:/product="Cys(Trt)"

(ix) FEATURE:
        (A) NAME/KEY: Modified-site
        (B) LOCATION:6
        (D) OTHER INFORMATION:/product="NMeAla"

(xi) SEQUENCE DESCRIPTION: SEQ ID NO: 184:

Lys Thr Ala Thr Cys Xaa
1               5

(2) INFORMATION FOR SEQ ID NO: 185:

(i) SEQUENCE CHARACTERISTICS:
        (A) LENGTH: 12 amino acids
        (B) TYPE: amino acid
        (C) STRANDEDNESS:
        (D) TOPOLOGY: linear (ii) MOLECULE TYPE: peptide (iii) HYPOTHETICAL: YES (iv) ANTI-SENSE: NO (v) FRAGMENT TYPE: N-terminal (ix) FEATURE:
        (A) NAME/KEY: Modified-site
        (B) LOCATION:5
        (D) OTHER INFORMATION:/product="Cys(Trt)"

(xi) SEQUENCE DESCRIPTION: SEQ ID NO: 185:

Lys Thr Ala Asp Cys Pro Arg Asn Pro His Lys Gly ( 2 ) INFORMATION FOR SEQ ID NO: 186:

( i ) SEQUENCE CHARACTERISTICS:
        ( A ) LENGTH: 12 amino acids
        ( B ) TYPE: amino acid
        ( C ) STRANDEDNESS:
        ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
        ( A ) NAME/KEY: Modified-site
        ( B ) LOCATION:5
        ( D ) OTHER INFORMATION:/product="Cys(Trt)"

( x i ) SEQUENCE DESCRIPTION: SEQ ID NO: 186:

Lys Thr Ala Asp Cys Pro Arg Asn Pro His Lys Gly
1               5                   10

( 2 ) INFORMATION FOR SEQ ID NO: 187:

( i ) SEQUENCE CHARACTERISTICS:
        ( A ) LENGTH: 12 amino acids
        ( B ) TYPE: amino acid
        ( C ) STRANDEDNESS:
        ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
        ( A ) NAME/KEY: Modified-site
        ( B ) LOCATION:5
        ( D ) OTHER INFORMATION:/product="Cys(Me)"

( x i ) SEQUENCE DESCRIPTION: SEQ ID NO: 187:

Lys Thr Ala Asp Cys Pro Arg Asn Pro His Lys Gly
1               5                   10

( 2 ) INFORMATION FOR SEQ ID NO: 188:

( i ) SEQUENCE CHARACTERISTICS:
        ( A ) LENGTH: 12 amino acids
        ( B ) TYPE: amino acid
        ( C ) STRANDEDNESS:
        ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
        ( A ) NAME/KEY: Modified-site
        ( B ) LOCATION:5
        ( D ) OTHER INFORMATION:/product="Cys(Et)"

( x i ) SEQUENCE DESCRIPTION: SEQ ID NO: 188:

```
Lys  Thr  Ala  Asp  Cys  Pro  Arg  Asn  Pro  His  Lys  Gly
1                   5                        10
```

( 2 ) INFORMATION FOR SEQ ID NO: 189:

( i ) SEQUENCE CHARACTERISTICS:
        ( A ) LENGTH: 12 amino acids
        ( B ) TYPE: amino acid
        ( C ) STRANDEDNESS:
        ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
        ( A ) NAME/KEY: Modified-site
        ( B ) LOCATION:5
        ( D ) OTHER INFORMATION:/product="Cys(Bzl)"

( x i ) SEQUENCE DESCRIPTION: SEQ ID NO: 189:

```
Lys  Thr  Ala  Asp  Cys  Pro  Arg  Asn  Pro  His  Lys  Gly
1                   5                        10
```

( 2 ) INFORMATION FOR SEQ ID NO: 190:

( i ) SEQUENCE CHARACTERISTICS:
        ( A ) LENGTH: 12 amino acids
        ( B ) TYPE: amino acid
        ( C ) STRANDEDNESS:
        ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
        ( A ) NAME/KEY: Modified-site
        ( B ) LOCATION:5
        ( D ) OTHER INFORMATION:/product="Cys(tBu)"

( x i ) SEQUENCE DESCRIPTION: SEQ ID NO: 190:

```
Lys  Thr  Ala  Asp  Cys  Pro  Arg  Asn  Pro  His  Lys  Gly
1                   5                        10
```

( 2 ) INFORMATION FOR SEQ ID NO: 191:

( i ) SEQUENCE CHARACTERISTICS:
        ( A ) LENGTH: 12 amino acids
        ( B ) TYPE: amino acid
        ( C ) STRANDEDNESS:
        ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
        ( A ) NAME/KEY: Modified-site
        ( B ) LOCATION:5
        ( D ) OTHER INFORMATION:/product="Cys(Dpm)"

( x i ) SEQUENCE DESCRIPTION: SEQ ID NO: 191:

Lys Thr Ala Asp Cys Pro Arg Asn Pro His Lys Gly
1               5                   10

( 2 ) INFORMATION FOR SEQ ID NO: 192:

( i ) SEQUENCE CHARACTERISTICS:
    ( A ) LENGTH: 4 amino acids
    ( B ) TYPE: amino acid
    ( C ) STRANDEDNESS:
    ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
    ( A ) NAME/KEY: Modified-site
    ( B ) LOCATION: 2
    ( D ) OTHER INFORMATION:/product="Cys(Trt)"

( i x ) FEATURE:
    ( A ) NAME/KEY: Modified-site
    ( B ) LOCATION: 4
    ( D ) OTHER INFORMATION:/product="Cys(R1)"
         / note="R1 as defined"

( x i ) SEQUENCE DESCRIPTION: SEQ ID NO: 192:

Gly Lys Thr Cys
1

( 2 ) INFORMATION FOR SEQ ID NO: 193:

( i ) SEQUENCE CHARACTERISTICS:
    ( A ) LENGTH: 5 amino acids
    ( B ) TYPE: amino acid
    ( C ) STRANDEDNESS:
    ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
    ( A ) NAME/KEY: Modified-site
    ( B ) LOCATION: 1
    ( D ) OTHER INFORMATION:/product="X is A"
         / note="A is as defined"

( i x ) FEATURE:
    ( A ) NAME/KEY: Modified-site
    ( B ) LOCATION: 2
    ( D ) OTHER INFORMATION:/product="Cys(R1)"
         / note="R1 is as defined"

( x i ) SEQUENCE DESCRIPTION: SEQ ID NO: 193:

Xaa Cys Pro Arg Asn
1               5

( 2 ) INFORMATION FOR SEQ ID NO: 194:

( i ) SEQUENCE CHARACTERISTICS:
    ( A ) LENGTH: 6 amino acids
    ( B ) TYPE: amino acid
    ( C ) STRANDEDNESS:
    ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
    ( A ) NAME/KEY: Modified-site
    ( B ) LOCATION:1
    ( D ) OTHER INFORMATION:/product="X is A"
        / note="A is as defined"

( i x ) FEATURE:
    ( A ) NAME/KEY: Modified-site
    ( B ) LOCATION:2
    ( D ) OTHER INFORMATION:/product="Cys(R1)"
        / note="R1 is as defined"

( x i ) SEQUENCE DESCRIPTION: SEQ ID NO: 194:

Xaa Cys Pro Arg Asn Pro
1                 5

( 2 ) INFORMATION FOR SEQ ID NO: 195:

( i ) SEQUENCE CHARACTERISTICS:
        ( A ) LENGTH: 7 amino acids
        ( B ) TYPE: amino acid
        ( C ) STRANDEDNESS:
        ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
    ( A ) NAME/KEY: Modified-site
    ( B ) LOCATION:1
    ( D ) OTHER INFORMATION:/product="X is A"
        / note="A is as defined"

( i x ) FEATURE:
    ( A ) NAME/KEY: Modified-site
    ( B ) LOCATION:2
    ( D ) OTHER INFORMATION:/product="Cys(R1)"
        / note="R1 is as defined"

( x i ) SEQUENCE DESCRIPTION: SEQ ID NO: 195:

Xaa Cys Pro Arg Asn Pro His
1                 5

( 2 ) INFORMATION FOR SEQ ID NO: 196:

( i ) SEQUENCE CHARACTERISTICS:
        ( A ) LENGTH: 8 amino acids
        ( B ) TYPE: amino acid
        ( C ) STRANDEDNESS:
        ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
    ( A ) NAME/KEY: Modified-site
    ( B ) LOCATION:1
    ( D ) OTHER INFORMATION:/product="X is A"

/ note="A is as defined"

( i x ) FEATURE:
            ( A ) NAME/KEY: Modified-site
            ( B ) LOCATION:2
            ( D ) OTHER INFORMATION:/product="Cys(R1)"
                 / note="R1 is as defined"

( x i ) SEQUENCE DESCRIPTION: SEQ ID NO: 196:

Xaa  Cys  Pro  Arg  Asn  Pro  His  Lys
    1                   5

( 2 ) INFORMATION FOR SEQ ID NO: 197:

( i ) SEQUENCE CHARACTERISTICS:
            ( A ) LENGTH: 9 amino acids
            ( B ) TYPE: amino acid
            ( C ) STRANDEDNESS:
            ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
            ( A ) NAME/KEY: Modified-site
            ( B ) LOCATION:1
            ( D ) OTHER INFORMATION:/product="X is A"
                 / note="A is as defined"

( i x ) FEATURE:
            ( A ) NAME/KEY: Modified-site
            ( B ) LOCATION:2
            ( D ) OTHER INFORMATION:/product="Cys(R1)"
                 / note="R1 is as defined"

( x i ) SEQUENCE DESCRIPTION: SEQ ID NO: 197:

Xaa  Cys  Pro  Arg  Asn  Pro  His  Lys  Gly
    1                   5

( 2 ) INFORMATION FOR SEQ ID NO: 198:

( i ) SEQUENCE CHARACTERISTICS:
            ( A ) LENGTH: 10 amino acids
            ( B ) TYPE: amino acid
            ( C ) STRANDEDNESS:
            ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
            ( A ) NAME/KEY: Modified-site
            ( B ) LOCATION:1
            ( D ) OTHER INFORMATION:/product="X is A"
                 / note="A is as defined"

( i x ) FEATURE:
            ( A ) NAME/KEY: Modified-site
            ( B ) LOCATION:2
            ( D ) OTHER INFORMATION:/product="Cys(R1)"
                 / note="R1 is as defined"

( x i ) SEQUENCE DESCRIPTION: SEQ ID NO: 198:

Xaa  Cys  Pro  Arg  Asn  Pro  His  Lys  Gly  Pro
    1                   5                        10

( 2 ) INFORMATION FOR SEQ ID NO: 199:

( i ) SEQUENCE CHARACTERISTICS:
      ( A ) LENGTH: 11 amino acids
      ( B ) TYPE: amino acid
      ( C ) STRANDEDNESS:
      ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
      ( A ) NAME/KEY: Modified-site
      ( B ) LOCATION:1
      ( D ) OTHER INFORMATION:/product="X is A"
         / note="A is as defined"

( i x ) FEATURE:
      ( A ) NAME/KEY: Modified-site
      ( B ) LOCATION:2
      ( D ) OTHER INFORMATION:/product="Cys(R1)"
         / note="R1 is as defined"

( x i ) SEQUENCE DESCRIPTION: SEQ ID NO: 199:

Xaa  Cys  Pro  Arg  Asn  Pro  His  Lys  Gly  Pro  Ala
   1                   5                        10

( 2 ) INFORMATION FOR SEQ ID NO: 200:

( i ) SEQUENCE CHARACTERISTICS:
      ( A ) LENGTH: 5 amino acids
      ( B ) TYPE: amino acid
      ( C ) STRANDEDNESS:
      ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
      ( A ) NAME/KEY: Modified-site
      ( B ) LOCATION:4
      ( D ) OTHER INFORMATION:/product="Cys(R1)"
         / note="R1 is as defined"

( i x ) FEATURE:
      ( A ) NAME/KEY: Modified-site
      ( B ) LOCATION:5
      ( D ) OTHER INFORMATION:/product="X is B"
         / note="B is as defined"

( x i ) SEQUENCE DESCRIPTION: SEQ ID NO: 200:

Thr  Ala  Asp  Cys  Xaa
   1                   5

( 2 ) INFORMATION FOR SEQ ID NO: 201:

( i ) SEQUENCE CHARACTERISTICS:
      ( A ) LENGTH: 6 amino acids
      ( B ) TYPE: amino acid
      ( C ) STRANDEDNESS:
      ( D ) TOPOLOGY: linear ( i i ) MOLECULE TYPE: peptide (iii) HYPOTHETICAL: YES (iv) ANTI-SENSE: NO (v) FRAGMENT TYPE: N-terminal (ix) FEATURE:
    (A) NAME/KEY: Modified-site
    (B) LOCATION:5
    (D) OTHER INFORMATION:/product="Cys(R1)"
    / note="R1 is as defined"

(ix) FEATURE:
    (A) NAME/KEY: Modified-site
    (B) LOCATION:6
    (D) OTHER INFORMATION:/product="X is B"
    / note="B is as defined"

(xi) SEQUENCE DESCRIPTION: SEQ ID NO: 201:

Lys Thr Ala Asp Cys Xaa
1               5

(2) INFORMATION FOR SEQ ID NO: 202:

(i) SEQUENCE CHARACTERISTICS:
    (A) LENGTH: 7 amino acids
    (B) TYPE: amino acid
    (C) STRANDEDNESS:
    (D) TOPOLOGY: linear (ii) MOLECULE TYPE: peptide (iii) HYPOTHETICAL: YES (iv) ANTI-SENSE: NO (v) FRAGMENT TYPE: N-terminal (ix) FEATURE:
    (A) NAME/KEY: Modified-site
    (B) LOCATION:6
    (D) OTHER INFORMATION:/product="Cys(R1)"
    / note="R1 is as defined"

(ix) FEATURE:
    (A) NAME/KEY: Modified-site
    (B) LOCATION:7
    (D) OTHER INFORMATION:/product="X is B"
    / note="B is as defined"

(xi) SEQUENCE DESCRIPTION: SEQ ID NO: 202:

Gly Lys Thr Ala Asp Cys Xaa
1                   5

(2) INFORMATION FOR SEQ ID NO: 203:

(i) SEQUENCE CHARACTERISTICS:
    (A) LENGTH: 8 amino acids
    (B) TYPE: amino acid
    (C) STRANDEDNESS:
    (D) TOPOLOGY: linear (ii) MOLECULE TYPE: peptide (iii) HYPOTHETICAL: YES (iv) ANTI-SENSE: NO (v) FRAGMENT TYPE: N-terminal (ix) FEATURE:
    (A) NAME/KEY: Modified-site
    (B) LOCATION:7
    (D) OTHER INFORMATION:/product="Cys(R1)"
    / note="R1 is as defined"

( i x ) FEATURE:
    ( A ) NAME/KEY: Modified-site
    ( B ) LOCATION:8
    ( D ) OTHER INFORMATION:/product="X is B"
        / note="B is as defined"

( x i ) SEQUENCE DESCRIPTION: SEQ ID NO: 203:

Asn Gly Lys Thr Ala Asp Cys Xaa
1                  5

( 2 ) INFORMATION FOR SEQ ID NO: 204:

( i ) SEQUENCE CHARACTERISTICS:
    ( A ) LENGTH: 5 amino acids
    ( B ) TYPE: amino acid
    ( C ) STRANDEDNESS:
    ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
    ( A ) NAME/KEY: Modified-site
    ( B ) LOCATION:4
    ( D ) OTHER INFORMATION:/product="Cys(R1)"
        / note="R1 is as defined"

( i x ) FEATURE:
    ( A ) NAME/KEY: Modified-site
    ( B ) LOCATION:5
    ( D ) OTHER INFORMATION:/product="X is B"
        / note="B is as defined"

( x i ) SEQUENCE DESCRIPTION: SEQ ID NO: 204:

Thr Ala Asn Cys Xaa
1            5

( 2 ) INFORMATION FOR SEQ ID NO: 205:

( i ) SEQUENCE CHARACTERISTICS:
    ( A ) LENGTH: 9 amino acids
    ( B ) TYPE: amino acid
    ( C ) STRANDEDNESS:
    ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
    ( A ) NAME/KEY: Modified-site
    ( B ) LOCATION:8
    ( D ) OTHER INFORMATION:/product="Cys(R1)"
        / note="R1 is as defined"

( i x ) FEATURE:
    ( A ) NAME/KEY: Modified-site
    ( B ) LOCATION:9
    ( D ) OTHER INFORMATION:/product="X is B"
        / note="B is as defined"

( x i ) SEQUENCE DESCRIPTION: SEQ ID NO: 205:

Cys Asn Gly Lys Thr Ala Asp Cys Xaa
1                  5

( 2 ) INFORMATION FOR SEQ ID NO: 206:

( i ) SEQUENCE CHARACTERISTICS:
        ( A ) LENGTH: 5 amino acids
        ( B ) TYPE: amino acid
        ( C ) STRANDEDNESS:
        ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
        ( A ) NAME/KEY: Modified-site
        ( B ) LOCATION:4
        ( D ) OTHER INFORMATION:/product="Cys(R1)"
            / note="R1 is as defined"

( i x ) FEATURE:
        ( A ) NAME/KEY: Modified-site
        ( B ) LOCATION:5
        ( D ) OTHER INFORMATION:/product="X is B"
            / note="B is as defined"

( x i ) SEQUENCE DESCRIPTION: SEQ ID NO: 206:

Ala   Ala   Asp   Cys   Xaa
    1                                5

( 2 ) INFORMATION FOR SEQ ID NO: 207:

( i ) SEQUENCE CHARACTERISTICS:
        ( A ) LENGTH: 5 amino acids
        ( B ) TYPE: amino acid
        ( C ) STRANDEDNESS:
        ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
        ( A ) NAME/KEY: Modified-site
        ( B ) LOCATION:4
        ( D ) OTHER INFORMATION:/product="Cys(R1)"
            / note="R1 is as defined"

( i x ) FEATURE:
        ( A ) NAME/KEY: Modified-site
        ( B ) LOCATION:5
        ( D ) OTHER INFORMATION:/product="X is B"
            / note="B is as defined"

( x i ) SEQUENCE DESCRIPTION: SEQ ID NO: 207:

Ser   Ala   Asp   Cys   Xaa
    1                                5

( 2 ) INFORMATION FOR SEQ ID NO: 208:

( i ) SEQUENCE CHARACTERISTICS:
        ( A ) LENGTH: 10 amino acids
        ( B ) TYPE: amino acid
        ( C ) STRANDEDNESS:
        ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
    ( A ) NAME/KEY: Modified-site
    ( B ) LOCATION:9
    ( D ) OTHER INFORMATION:/product="Cys(R1)"
       / note="R1 is as defined"

( i x ) FEATURE:
    ( A ) NAME/KEY: Modified-site
    ( B ) LOCATION:10
    ( D ) OTHER INFORMATION:/product="X is B"
       / note="B is as defined"

( x i ) SEQUENCE DESCRIPTION: SEQ ID NO: 208:

```
Tyr  Cys  Asn  Gly  Lys  Thr  Ala  Asp  Cys  Xaa
 1             5                             10
```

( 2 ) INFORMATION FOR SEQ ID NO: 209:

( i ) SEQUENCE CHARACTERISTICS:
    ( A ) LENGTH: 5 amino acids
    ( B ) TYPE: amino acid
    ( C ) STRANDEDNESS:
    ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
    ( A ) NAME/KEY: Modified-site
    ( B ) LOCATION:4
    ( D ) OTHER INFORMATION:/product="Cys(R1)"
       / note="R1 is as defined"

( i x ) FEATURE:
    ( A ) NAME/KEY: Modified-site
    ( B ) LOCATION:5
    ( D ) OTHER INFORMATION:/product="X is B"
       / note="B is as defined"

( x i ) SEQUENCE DESCRIPTION: SEQ ID NO: 209:

```
Ser  Ala  Gly  Cys  Xaa
 1                   5
```

( 2 ) INFORMATION FOR SEQ ID NO: 210:

( i ) SEQUENCE CHARACTERISTICS:
    ( A ) LENGTH: 5 amino acids
    ( B ) TYPE: amino acid
    ( C ) STRANDEDNESS:
    ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
    ( A ) NAME/KEY: Modified-site
    ( B ) LOCATION:2
    ( D ) OTHER INFORMATION:/product="Cys(Trt)"

( i x ) FEATURE:
    ( A ) NAME/KEY: Modified-site
    ( B ) LOCATION:4

(D) OTHER INFORMATION:/product="Cys(R1)"
                        /note="R1 is as defined"

(ix) FEATURE:
                    (A) NAME/KEY: Modified-site
                    (B) LOCATION:5
                    (D) OTHER INFORMATION:/product="X is B"
                        /note="B is as defined"

(xi) SEQUENCE DESCRIPTION: SEQ ID NO: 210:

Thr Cys Asp Cys Xaa
    1               5

(2) INFORMATION FOR SEQ ID NO: 211:

(i) SEQUENCE CHARACTERISTICS:
                    (A) LENGTH: 6 amino acids
                    (B) TYPE: amino acid
                    (C) STRANDEDNESS:
                    (D) TOPOLOGY: linear (ii) MOLECULE TYPE: peptide (iii) HYPOTHETICAL: YES (iv) ANTI-SENSE: NO (v) FRAGMENT TYPE: N-terminal (ix) FEATURE:
                    (A) NAME/KEY: Modified-site
                    (B) LOCATION:3
                    (D) OTHER INFORMATION:/product="Cys(Trt)"

(ix) FEATURE:
                    (A) NAME/KEY: Modified-site
                    (B) LOCATION:5
                    (D) OTHER INFORMATION:/product="Cys(R1)"
                        /note="R1 is as defined"

(ix) FEATURE:
                    (A) NAME/KEY: Modified-site
                    (B) LOCATION:6
                    (D) OTHER INFORMATION:/product="X is B"
                        /note="B is as defined"

(xi) SEQUENCE DESCRIPTION: SEQ ID NO: 211:

Lys Thr Cys Asp Cys Xaa
    1               5

(2) INFORMATION FOR SEQ ID NO: 212:

(i) SEQUENCE CHARACTERISTICS:
                    (A) LENGTH: 11 amino acids
                    (B) TYPE: amino acid
                    (C) STRANDEDNESS:
                    (D) TOPOLOGY: linear (ii) MOLECULE TYPE: peptide (iii) HYPOTHETICAL: YES (iv) ANTI-SENSE: NO (v) FRAGMENT TYPE: N-terminal (ix) FEATURE:
                    (A) NAME/KEY: Modified-site
                    (B) LOCATION:10
                    (D) OTHER INFORMATION:/product="Cys(Trt)"

(ix) FEATURE:
                    (A) NAME/KEY: Modified-site
                    (B) LOCATION:11
                    (D) OTHER INFORMATION:/product="X is B"
                        /note="B is as defined"

( x i ) SEQUENCE DESCRIPTION: SEQ ID NO: 212:

Asp Tyr Cys Asn Gly Lys Thr Ala Asp Cys Xaa
1               5                   10

( 2 ) INFORMATION FOR SEQ ID NO: 213:

( i ) SEQUENCE CHARACTERISTICS:
    ( A ) LENGTH: 12 amino acids
    ( B ) TYPE: amino acid
    ( C ) STRANDEDNESS:
    ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
    ( A ) NAME/KEY: Modified-site
    ( B ) LOCATION:11
    ( D ) OTHER INFORMATION:/product="Cys(Trt)"

( i x ) FEATURE:
    ( A ) NAME/KEY: Modified-site
    ( B ) LOCATION:12
    ( D ) OTHER INFORMATION:/product="X is B"
        / note="B is as defined"

( x i ) SEQUENCE DESCRIPTION: SEQ ID NO: 213:

Asp Asp Tyr Cys Asn Gly Lys Thr Ala Asp Cys Xaa
1                   5                       10

( 2 ) INFORMATION FOR SEQ ID NO: 214:

( i ) SEQUENCE CHARACTERISTICS:
    ( A ) LENGTH: 13 amino acids
    ( B ) TYPE: amino acid
    ( C ) STRANDEDNESS:
    ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
    ( A ) NAME/KEY: Modified-site
    ( B ) LOCATION:12
    ( D ) OTHER INFORMATION:/product="Cys(Trt)"

( i x ) FEATURE:
    ( A ) NAME/KEY: Modified-site
    ( B ) LOCATION:13
    ( D ) OTHER INFORMATION:/product="X is B"
        / note="B is as defined"

( x i ) SEQUENCE DESCRIPTION: SEQ ID NO: 214:

Met Asp Asp Tyr Cys Asn Gly Lys Thr Ala Asp Cys Xaa
1                       5                       10

( 2 ) INFORMATION FOR SEQ ID NO: 215:

( i ) SEQUENCE CHARACTERISTICS:
    ( A ) LENGTH: 10 amino acids
    ( B ) TYPE: amino acid
    ( C ) STRANDEDNESS:
    ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
    ( A ) NAME/KEY: Modified-site
    ( B ) LOCATION:5
    ( D ) OTHER INFORMATION:/product="Cys(Trt)"

( x i ) SEQUENCE DESCRIPTION: SEQ ID NO: 215:

```
Lys Thr Ala Asp Cys Pro Arg Asn Pro His
1               5                   10
```

( 2 ) INFORMATION FOR SEQ ID NO: 216:

( i ) SEQUENCE CHARACTERISTICS:
    ( A ) LENGTH: 6 amino acids
    ( B ) TYPE: amino acid
    ( C ) STRANDEDNESS:
    ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
    ( A ) NAME/KEY: Modified-site
    ( B ) LOCATION:2
    ( D ) OTHER INFORMATION:/product="Arg(Mtr)"

( i x ) FEATURE:
    ( A ) NAME/KEY: Modified-site
    ( B ) LOCATION:3
    ( D ) OTHER INFORMATION:/product="Asn(Trt)"

( i x ) FEATURE:
    ( A ) NAME/KEY: Modified-site
    ( B ) LOCATION:5
    ( D ) OTHER INFORMATION:/product="His(Trt)"

( i x ) FEATURE:
    ( A ) NAME/KEY: Modified-site
    ( B ) LOCATION:6
    ( D ) OTHER INFORMATION:/product="Lys(Boc)"

( x i ) SEQUENCE DESCRIPTION: SEQ ID NO: 216:

```
Pro Arg Asn Pro His Lys
1               5
```

( 2 ) INFORMATION FOR SEQ ID NO: 217:

( i ) SEQUENCE CHARACTERISTICS:
    ( A ) LENGTH: 7 amino acids
    ( B ) TYPE: amino acid
    ( C ) STRANDEDNESS:
    ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
    ( A ) NAME/KEY: Modified-site ( B ) LOCATION:1
                    ( D ) OTHER INFORMATION:/product="Cys(Trt)"

( i x ) FEATURE:
                    ( A ) NAME/KEY: Modified-site
                    ( B ) LOCATION:7
                    ( D ) OTHER INFORMATION:/product="Lys(Boc)"

( x i ) SEQUENCE DESCRIPTION: SEQ ID NO: 217:

Cys  Pro  Arg  Asn  Pro  His  Lys
    1                    5

( 2 ) INFORMATION FOR SEQ ID NO: 218:

( i ) SEQUENCE CHARACTERISTICS:
                    ( A ) LENGTH: 6 amino acids
                    ( B ) TYPE: amino acid
                    ( C ) STRANDEDNESS:
                    ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
                    ( A ) NAME/KEY: Modified-site
                    ( B ) LOCATION:1
                    ( D ) OTHER INFORMATION:/product="Fmoc-Lys(Boc)"

( i x ) FEATURE:
                    ( A ) NAME/KEY: Modified-site
                    ( B ) LOCATION:2
                    ( D ) OTHER INFORMATION:/product="Thr(But)"

( i x ) FEATURE:
                    ( A ) NAME/KEY: Modified-site
                    ( B ) LOCATION:4
                    ( D ) OTHER INFORMATION:/product="Asp(OBut)"

( i x ) FEATURE:
                    ( A ) NAME/KEY: Modified-site
                    ( B ) LOCATION:5
                    ( D ) OTHER INFORMATION:/product="Cys(Trt)"

( x i ) SEQUENCE DESCRIPTION: SEQ ID NO: 218:

Lys  Thr  Ala  Asp  Cys  Pro
    1                    5

( 2 ) INFORMATION FOR SEQ ID NO: 219:

( i ) SEQUENCE CHARACTERISTICS:
                    ( A ) LENGTH: 6 amino acids
                    ( B ) TYPE: amino acid
                    ( C ) STRANDEDNESS:
                    ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
                    ( A ) NAME/KEY: Modified-site
                    ( B ) LOCATION:2
                    ( D ) OTHER INFORMATION:/product="Thr(But)"

( i x ) FEATURE:
                    ( A ) NAME/KEY: Modified-site
                    ( B ) LOCATION:4

-continued ( D ) OTHER INFORMATION:/product="Asp(OBut)"

( i x ) FEATURE:
    ( A ) NAME/KEY: Modified-site
    ( B ) LOCATION:5
    ( D ) OTHER INFORMATION:/product="Cys(Trt)"

( i x ) FEATURE:
    ( A ) NAME/KEY: Modified-site
    ( B ) LOCATION:1
    ( D ) OTHER INFORMATION:/product="Lys(Boc)"
      / label=n ( x i ) SEQUENCE DESCRIPTION: SEQ ID NO: 219:

Lys Thr Ala Asp Cys Pro
 1        5

( 2 ) INFORMATION FOR SEQ ID NO: 220:

( i ) SEQUENCE CHARACTERISTICS:
    ( A ) LENGTH: 12 amino acids
    ( B ) TYPE: amino acid
    ( C ) STRANDEDNESS:
    ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
    ( A ) NAME/KEY: Modified-site
    ( B ) LOCATION:1
    ( D ) OTHER INFORMATION:/product="Ac-Lys"

( i x ) FEATURE:
    ( A ) NAME/KEY: Modified-site
    ( B ) LOCATION:5
    ( D ) OTHER INFORMATION:/product="Cys(Trt)"

( i x ) FEATURE:
    ( A ) NAME/KEY: Modified-site
    ( B ) LOCATION:12
    ( D ) OTHER INFORMATION:/product="Gly-NH2"

( x i ) SEQUENCE DESCRIPTION: SEQ ID NO: 220:

Lys Thr Ala Asp Cys Pro Arg Asn Pro His Lys Gly
 1        5              10

( 2 ) INFORMATION FOR SEQ ID NO: 221:

( i ) SEQUENCE CHARACTERISTICS:
    ( A ) LENGTH: 5 amino acids
    ( B ) TYPE: amino acid
    ( C ) STRANDEDNESS:
    ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
    ( A ) NAME/KEY: Modified-site
    ( B ) LOCATION:4
    ( D ) OTHER INFORMATION:/product="Cys(R1)"
      / note="R1 is as defined"

( i x ) FEATURE:
    ( A ) NAME/KEY: Modified-site (B) LOCATION:5
(D) OTHER INFORMATION:/product="X is B"
    /note="B is as defined"

(x i) SEQUENCE DESCRIPTION: SEQ ID NO: 221:

Thr Gly Asp Cys Xaa
1               5

(2) INFORMATION FOR SEQ ID NO: 222:

(i) SEQUENCE CHARACTERISTICS:
    (A) LENGTH: 4 amino acids
    (B) TYPE: amino acid
    (C) STRANDEDNESS:
    (D) TOPOLOGY: linear (i i) MOLECULE TYPE: peptide (i i i) HYPOTHETICAL: YES (i v) ANTI-SENSE: NO (v) FRAGMENT TYPE: N-terminal (x i) SEQUENCE DESCRIPTION: SEQ ID NO: 222:

Gly Ser Ala Asp
1

(2) INFORMATION FOR SEQ ID NO: 223:

(i) SEQUENCE CHARACTERISTICS:
    (A) LENGTH: 6 amino acids
    (B) TYPE: amino acid
    (C) STRANDEDNESS:
    (D) TOPOLOGY: linear (i i) MOLECULE TYPE: peptide (i i i) HYPOTHETICAL: YES (i v) ANTI-SENSE: NO (v) FRAGMENT TYPE: N-terminal (i x) FEATURE:
    (A) NAME/KEY: Modified-site
    (B) LOCATION:1
    (D) OTHER INFORMATION:/product="Fmoc-Lys(Boc)"

(i x) FEATURE:
    (A) NAME/KEY: Modified-site
    (B) LOCATION:2
    (D) OTHER INFORMATION:/product="Thr(But)"

(i x) FEATURE:
    (A) NAME/KEY: Modified-site
    (B) LOCATION:4
    (D) OTHER INFORMATION:/product="Asn(Trt)"

(i x) FEATURE:
    (A) NAME/KEY: Modified-site
    (B) LOCATION:5
    (D) OTHER INFORMATION:/product="Cys(Trt)"

(x i) SEQUENCE DESCRIPTION: SEQ ID NO: 223:

Lys Thr Ala Asn Cys Pro
1               5

(2) INFORMATION FOR SEQ ID NO: 224:

(i) SEQUENCE CHARACTERISTICS:
    (A) LENGTH: 4 amino acids
    (B) TYPE: amino acid
    (C) STRANDEDNESS:

(D) TOPOLOGY: linear (i i) MOLECULE TYPE: peptide (i i i) HYPOTHETICAL: YES (i v) ANTI-SENSE: NO (v) FRAGMENT TYPE: N-terminal (i x) FEATURE:
    (A) NAME/KEY: Modified-site
    (B) LOCATION:1
    (D) OTHER INFORMATION:/product="Fmoc-X"
    / note="X is Glp (Glp is as defined)"

(i x) FEATURE:
    (A) NAME/KEY: Modified-site
    (B) LOCATION:2
    (D) OTHER INFORMATION:/product="Ser(But)"

(i x) FEATURE:
    (A) NAME/KEY: Modified-site
    (B) LOCATION:4
    (D) OTHER INFORMATION:/product="Asp(Trt)"

(x i) SEQUENCE DESCRIPTION: SEQ ID NO: 224:

Xaa Ser Ala Asp
1

(2) INFORMATION FOR SEQ ID NO: 225:

(i) SEQUENCE CHARACTERISTICS:
    (A) LENGTH: 4 amino acids
    (B) TYPE: amino acid
    (C) STRANDEDNESS:
    (D) TOPOLOGY: linear (i i) MOLECULE TYPE: peptide (i i i) HYPOTHETICAL: YES (i v) ANTI-SENSE: NO (v) FRAGMENT TYPE: N-terminal (i x) FEATURE:
    (A) NAME/KEY: Modified-site
    (B) LOCATION:1
    (D) OTHER INFORMATION:/product="Fmoc-Ile"

(i x) FEATURE:
    (A) NAME/KEY: Modified-site
    (B) LOCATION:2
    (D) OTHER INFORMATION:/product="Ser(But)"

(x i) SEQUENCE DESCRIPTION: SEQ ID NO: 225:

Ile Ser Ala Gly
1

(2) INFORMATION FOR SEQ ID NO: 226:

(i) SEQUENCE CHARACTERISTICS:
    (A) LENGTH: 4 amino acids
    (B) TYPE: amino acid
    (C) STRANDEDNESS:
    (D) TOPOLOGY: linear (i i) MOLECULE TYPE: peptide (i i i) HYPOTHETICAL: YES (i v) ANTI-SENSE: NO (v) FRAGMENT TYPE: N-terminal ( i x ) FEATURE:
   ( A ) NAME/KEY: Modified-site
   ( B ) LOCATION:1
   ( D ) OTHER INFORMATION:/product="Fmoc-Arg(Mtr)"

( i x ) FEATURE:
   ( A ) NAME/KEY: Modified-site
   ( B ) LOCATION:2
   ( D ) OTHER INFORMATION:/product="Ser(But)"

( x i ) SEQUENCE DESCRIPTION: SEQ ID NO: 226:

Arg Ser Ala Gly
1

( 2 ) INFORMATION FOR SEQ ID NO: 227:

( i ) SEQUENCE CHARACTERISTICS:
      ( A ) LENGTH: 4 amino acids
      ( B ) TYPE: amino acid
      ( C ) STRANDEDNESS:
      ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
      ( A ) NAME/KEY: Modified-site
      ( B ) LOCATION:1
      ( D ) OTHER INFORMATION:/product="Fmoc-Lys(Boc)"

( i x ) FEATURE:
      ( A ) NAME/KEY: Modified-site
      ( B ) LOCATION:4
      ( D ) OTHER INFORMATION:/product="Asp(Trt)"

( x i ) SEQUENCE DESCRIPTION: SEQ ID NO: 227:

Lys Gly Gly Asp
1

( 2 ) INFORMATION FOR SEQ ID NO: 228:

( i ) SEQUENCE CHARACTERISTICS:
      ( A ) LENGTH: 8 amino acids
      ( B ) TYPE: amino acid
      ( C ) STRANDEDNESS:
      ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( i x ) FEATURE:
      ( A ) NAME/KEY: Modified-site
      ( B ) LOCATION:1
      ( D ) OTHER INFORMATION:/product="Boc-Lys(Boc)"

( i x ) FEATURE:
      ( A ) NAME/KEY: Modified-site
      ( B ) LOCATION:2
      ( D ) OTHER INFORMATION:/product="Thr(But)"

( i x ) FEATURE:
      ( A ) NAME/KEY: Modified-site
      ( B ) LOCATION:4
      ( D ) OTHER INFORMATION:/product="Asp(OBut)"

( i x ) FEATURE:

(A) NAME/KEY: Modified-site
(B) LOCATION:5
(D) OTHER INFORMATION:/product="Cys(Trt)"

(ix) FEATURE:
(A) NAME/KEY: Modified-site
(B) LOCATION:7
(D) OTHER INFORMATION:/product="Arg(Mtr)"

(ix) FEATURE:
(A) NAME/KEY: Modified-site
(B) LOCATION:8
(D) OTHER INFORMATION:/product="Asn(Trt)"

(xi) SEQUENCE DESCRIPTION: SEQ ID NO: 228:

Lys Thr Ala Asp Cys Pro Arg Asn
1               5